US 6,940,296 B2

(12) United States Patent
Yamada

(10) Patent No.: US 6,940,296 B2
(45) Date of Patent: *Sep. 6, 2005

(54) CONTACT HOLE STANDARD TEST DEVICE, METHOD OF FORMING THE SAME, METHOD OF TESTING CONTACT HOLE, METHOD AND APPARATUS FOR MEASURING A THICKNESS OF A FILM, AND METHOD OF TESTING A WAFER

(75) Inventor: Keizo Yamada, Tokyo (JP)

(73) Assignee: Fab Solutions, Inc., Kanagawa (JP)

(*) Notice: Subject to any disclaimer, the term of this patent is extended or adjusted under 35 U.S.C. 154(b) by 0 days.

This patent is subject to a terminal disclaimer.

(21) Appl. No.: 10/843,158

(22) Filed: May 11, 2004

(65) Prior Publication Data

US 2004/0212373 A1 Oct. 28, 2004

Related U.S. Application Data

(62) Division of application No. 09/451,440, filed on Nov. 30, 1999.

(30) Foreign Application Priority Data

Nov. 30, 1998 (JP) .......................................... 10-340636
Dec. 8, 1998 (JP) .......................................... 10-348988
Dec. 10, 1998 (JP) .......................................... 10-351928

(51) Int. Cl.$^7$ .......................................... G01R 31/304
(52) U.S. Cl. .................. 324/751; 324/752; 324/501
(58) Field of Search .................. 324/750, 751, 324/752, 753, 765, 158.1, 72.5, 501; 250/310, 311; 382/149; 438/14, 17; 356/364

(56) References Cited

U.S. PATENT DOCUMENTS 3,614,608 A   10/1971   Giedd et al.
4,949,162 A   8/1990    Tamaki et al.
4,980,639 A   12/1990   Yoshizawa et al.

(Continued)

FOREIGN PATENT DOCUMENTS

JP   50-63990    5/1975
JP   57-06310    1/1982
JP   62-19707    1/1987

(Continued)

OTHER PUBLICATIONS

"An In–Line Contact and Via Hole Inspection Method Using Electron Beam Compensation Current", Yamada et al., IEEE 1999, available from http://www.fabsol.com/us/images/library/21.pdf.

Primary Examiner—Vinh Nguyen
Assistant Examiner—Jimmy Nguyen
(74) Attorney, Agent, or Firm—Neil A. Steinberg

(57) ABSTRACT

The present invention provides a standard test device used for testing a hole of a semiconductor device. The standard test device has a structure which comprises: at least a dummy film on a base surface; at least an insulating layer which has at least one opening penetrating through the insulating layer, so that a part of a top surface of the at least dummy film is shown through the at least one opening, wherein the at least dummy film has a predetermined constant thickness at least around the at least one opening. The standard test device makes it easily possible to determine or measure a thickness of a residual film on a bottom of the contact hole.

36 Claims, 54 Drawing Sheets

U.S. PATENT DOCUMENTS

| | | |
|---|---|---|
| 4,988,877 A | 1/1991 | Stokowksi et al. |
| 5,001,536 A | 3/1991 | Fukuzawa et al. |
| 5,089,774 A | 2/1992 | Nakano |
| 5,132,507 A | 7/1992 | Nakano |
| 5,280,176 A | 1/1994 | Jach et al. |
| 5,327,012 A | 7/1994 | Yano et al. |
| 5,365,034 A | 11/1994 | Kawamura et al. |
| 5,412,210 A | 5/1995 | Todokoro et al. |
| 5,453,994 A | 9/1995 | Kawamoto et al. |
| 5,493,236 A | 2/1996 | Ishii et al. |
| 5,614,833 A | 3/1997 | Golladay |
| 5,637,186 A | 6/1997 | Liu et al. |
| 5,757,198 A | 5/1998 | Shida et al. |
| 5,780,870 A | 7/1998 | Maeda et al. |
| 5,781,017 A * | 7/1998 | Cole et al. ................. 324/751 |
| 5,801,540 A | 9/1998 | Sakaguchi |
| 5,815,002 A | 9/1998 | Nikawa |
| 5,900,645 A | 5/1999 | Yamada |
| 5,989,919 A | 11/1999 | Aoki |
| 6,037,588 A | 3/2000 | Liu et al. |
| 6,091,249 A * | 7/2000 | Talbot et al. ............... 324/751 |
| 6,127,193 A | 10/2000 | Bang et al. |
| 6,294,919 B1 | 9/2001 | Baumgart |
| 6,317,514 B1 | 11/2001 | Reinhorn et al. |
| 6,504,393 B1 * | 1/2003 | Lo et al. ..................... 324/765 |

FOREIGN PATENT DOCUMENTS

| | | |
|---|---|---|
| JP | 63-009807 | 1/1988 |
| JP | 3-205573 | 9/1991 |
| JP | 4-62857 | 2/1992 |
| JP | 05-045147 | 2/1993 |
| JP | 06-273297 | 6/1994 |
| JP | 07-066172 | 3/1995 |
| JP | 08-005528 | 1/1996 |
| JP | 08-313244 | 11/1996 |
| JP | 09-061142 | 3/1997 |
| JP | 10-281746 | 10/1998 |
| JP | 10-300450 | 11/1998 |
| JP | 11-26343 | 1/1999 |
| JP | 2000-124276 | 4/2000 |
| JP | 2000-164715 | 6/2000 |
| JP | 2000-174077 | 6/2000 |
| JP | 2000-180143 | 6/2000 |

* cited by examiner

| Current (PA) | Number |
|---|---|
| 56 | 24 |
| 55 | 14 |
| 55 | 23 |
| 55 | 25 |
| 55 | 34 |
| 54 | 13 |
| 54 | 15 |
| 54 | 22 |
| 54 | 26 |
| 54 | 33 |
| 54 | 35 |
| 53 | 03 |
| 53 | 12 |
| 53 | 16 |

FIGURE 39

| Current PA | No. |
|---|---|
| 12 | 55 |
| 12 | 54 |
| 12 | 53 |
| 12 | 52 |
| 12 | 51 |
| 12 | 45 |
| 12 | 35 |
| 12 | 34 |
| 12 | 33 |
| 12 | 25 |
| 12 | 24 |
| 12 | 23 |
| 12 | 22 |
| 12 | 15 |
| 12 | 14 |
| 12 | 13 |
| 12 | 12 |
| 12 | 44 |
| 11 | 43 |
| 11 | 42 |
| 11 | 41 |
| 11 | 32 |
| 11 | 31 |
| 10 | 21 |
| 10 | 11 |

FIGURE 42

| Block | Beam Current (PA) |
|---|---|
| A | 10 |
| B | 50 |
| C | 100 |

FIGURE 45

CONTACT HOLE STANDARD TEST DEVICE, METHOD OF FORMING THE SAME, METHOD OF TESTING CONTACT HOLE, METHOD AND APPARATUS FOR MEASURING A THICKNESS OF A FILM, AND METHOD OF TESTING A WAFER

RELATED APPLICATIONS

This application is a divisional application of Application Ser. No. 09/451,440 (still pending), filed Nov. 30, 1999, which claims the benefit of priority, under 35 USC § 119, to Japanese Patent Application Nos. 10-340636, 10-348988, and 10-351928 filed on Nov. 30, 1998, Dec. 8, 1998, and Dec. 10, 1998, respectively.

BACKGROUND OF THE INVENTION

The present invention relates to a contact hole standard test device to be used for not only determining whether or not a residual film resides on a bottom of a contact hole but also measuring a thickness of the residual film on the basis of contrast of secondary electron image and/or beam pass current upon irradiation of an electron beam on the residual film, and further relates to a method of forming the contact hole standard test device.

The present invention also relates to a method and an apparatus for measuring a thin film on the basis of beam pass current upon irradiation of an electron beam on the thin film.

The present invention also relates to a method of testing a wafer to detect defective contact holes in a shortened time period without testing all of the contact holes.

SUMMARY OF THE INVENTION

Accordingly, it is an object of the present invention to provide a novel contact hole standard test device to be used for not only determining whether or not a residual film resides on a bottom of a contact hole but also measuring a thickness of the residual film on the basis of contrast of secondary electron image and/or beam pass current upon irradiation of an electron beam on the residual film.

It is a further object of the present invention to provide a novel a method of forming the contact hole standard test device.

It is a still further object of the present invention to provide a novel method for measuring a thin film on the basis of beam pass current upon irradiation of an electron beam on the thin film.

It is yet a further object of the present invention to provide a novel apparatus for measuring a thin film on the basis of beam pass current upon irradiation of an electron beam on the thin film.

It is a further more object of the present invention to provide a novel a method of testing a wafer to detect defective contact holes in a shortened time period without testing all of the contact holes.

The present invention provides a standard test device used for testing a hole of a semiconductor device. The standard test device has a structure which comprises: at least a dummy film on a base surface; at least an insulating layer which has at least one opening penetrating through the insulating layer, so that a part of a top surface of the at least dummy film is shown through the at least one opening, wherein the at least dummy film has a predetermined constant thickness at least around the at least one opening. The standard test device makes it easily possible to determine or measure a thickness of a residual film on a bottom of the contact hole.

The above and other objects, features and advantages of the present invention will be apparent from the following descriptions.

BRIEF DESCRIPTION OF THE DRAWINGS

Preferred embodiments according to the present invention will be described in detail with reference to the accompanying drawings.

FIG. 39 is a table on which the measured beam pass current values and the identification numbers allocated to the corresponding blocks in order of magnitude of the measured beam pass current value on the basis of FIG. 38.

FIG. 42 is a table on which the measured beam pass current values and the identification numbers allocated to the corresponding sub-blocks in order of magnitude of the measured beam pass current value on the basis of FIG. 41 in a twenty second embodiment in accordance with the present invention.

FIG. 45 is a table on which the blocks and irradiation electron beam current values of the individual blocks are shown when the electron beam irradiator system of FIG. 44 is used in this twenty fourth embodiment in accordance with the present invention.

DISCLOSURE OF THE INVENTION

Figure 1:
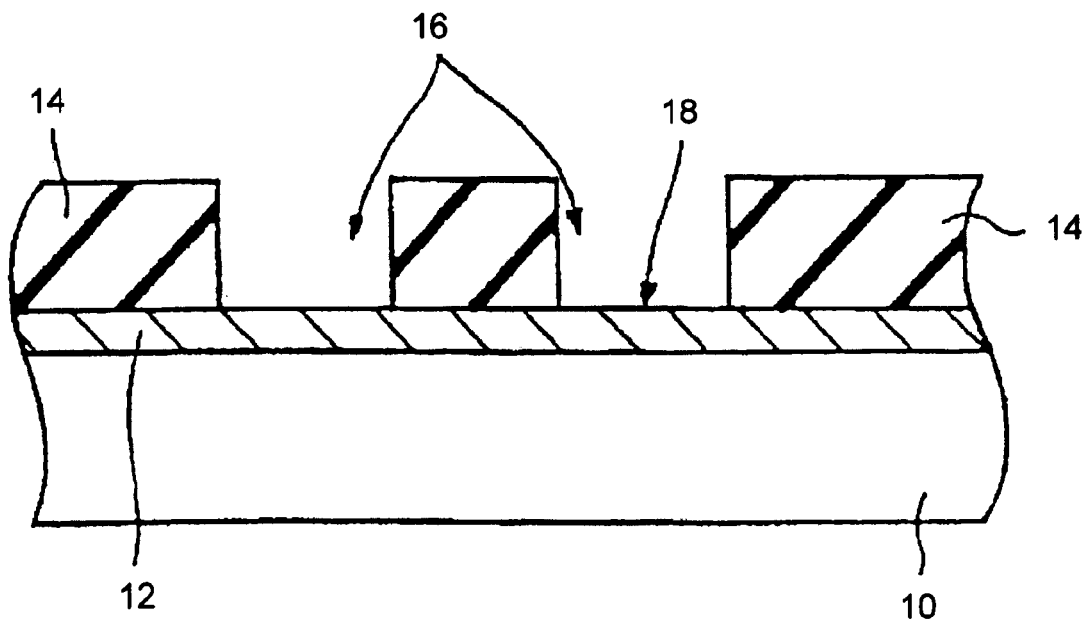
FIG. 1 is a fragmentary cross sectional elevation view illustrative of a novel standard test device of a first embodiment in accordance with the present invention.

The first present invention provides a standard test device used for testing a hole of a semiconductor device. The standard test device has a structure which comprises: at least a dummy film on a base surface; at least an insulating layer which has at least one opening penetrating through the insulating layer, so that a part of a top surface of the at least dummy film is shown through the at least one opening, wherein the at least dummy film has a predetermined constant thickness at least around the at least one opening. The standard test device makes it easily possible to determine or measure a thickness of a residual film on a bottom of the contact hole.

The present inventor could found out the fact that the contrast of the secondary electron image of the bottom of the hole such as the contact hole depends upon the thickness of the residual film on the bottom of the hole such as the contact hole. The present inventor thus conceived that it is possible to measure or determine the thickness of the residual film on the bottom of the hole such as the contact hole by comparing the contrast of the secondary electron image of the bottom of the contact hole to a reference contrast of the standard test device which has the dummy film having the constant thickness previously known, wherein the dummy film corresponds to the residual film on the bottom of the hole such as the contact hole of the semiconductor device.

The actual residual film is extremely thin and a thickness thereof is in the range of a few angstroms to several tens of angstroms. For this reason, it is difficult to control etching process to have the residual film have a highly accurate thickness if the residual film of the standard test device is formed by etching process. Thus, it is difficult to form the standard test device having the residual film formed by the etching process.

In accordance with the present invention, however, the dummy film is formed which corresponds to the residual film, wherein the dummy film is deposited to have a highly accurate controlled thickness because the dummy film is not formed by the etching process. The standard test device has this dummy film.

The standard test device has the opening positioned over the dummy film, wherein the opening corresponds to the hole such as the contact hole. A current of the secondary electrons obtained by irradiation of an electron beam onto the hole depends not only on the thickness of the residual film on the bottom of the hole such as the contact hole but also on the existence of the hole such as the contact hole. For example, secondary electrons emitted from the bottom of the hole such as the contact hole may be absorbed into side walls of the contact hole. The secondary electrons are further influenced by an electric field in the hole such as the contact hole. The contrast of the secondary electron image depends not only upon the thickness of the residual film but also upon the presence of the contact hole over the residual film. For this reason, the standard test device has the opening over the dummy film, wherein the opening corresponds to the hole such as the contact hole and the dummy film corresponds to the residual film. The standard test device having both the dummy film and the opening is capable of obtaining the same reference contrast of the secondary electron image as the actual contrast of the secondary electron image of the actual hole such as the contact hole.

The dummy film corresponding to the residual film is provided on the base surface such as the surface of the substrate. The insulating film having the opening which corresponds to the hole such as the contact hole is provided on the dummy film, thereby forming the same structure as that the residual film having the known thickness resides on the bottom of the hole such as the contact hole.

Accordingly, the use of the standard test device having the dummy film and the opening makes it possible to determine or measure a highly accurate value of the thickness of the residual film on the bottom of the hole such as the contact hole by comparing the reference contrast of the secondary electron image of the opening of the standard test device to the actual contrast of the secondary electron image of the hole such as the contact hole.

Further, in place of the above comparison in the contact of the secondary electron image, the use of the standard test device having the dummy film and the opening makes it possible to determine or measure a highly accurate value of the thickness of the residual film on the bottom of the hole such as the contact hole by comparing a reference beam pass current having passed from the bottom of the opening through the dummy film of the standard test device to the actual beam pass current having passed from the bottom of the hole through the residual film.

The insulating film having the opening may be made of a resin such as a resin having any one of sensitivity to an ultraviolet ray, an X-ray end an electron beam. If the insulating film is made of such photo-sensitive resin, then the opening may be formed by patterning the photo-sensitive resin film without providing any substantive damage to the dummy film underlying the photo-sensitive resin film, even if the dummy film is extremely thin such a a few angstroms.

The limitation of the plane size of the opening in the photo-sensitive resin depends upon the limitation of the lithography such as photo-lithography, X-ray lithography or electron beam lithography. Even if the size of the contact hole is extremely small, then the opening size may be adopted to be identical with the contact hole.

It is preferable that the at least dummy film has the predetermined constant thickness throughout an entire region thereof.

It is also preferable that the at least dummy film is made of the same material as a film in which the hole of the semiconductor device is formed. Namely, the residual film is a part of the film in which the hole such as the contact hole. Thus, the dummy film is made of the same material as the residual film, so that the reference contrast of the secondary electron image of the opening and the reference beam pass current of the standard test device are made closer to the actual contrast of the secondary electron image of the hole such as the contact hole and the actual reference beam pass current. An accuracy in evaluation or measurement to thickness of the residual film by use of the standard test device is improved.

It is preferable that the at least one opening has the same plane size and aspect ratio as the hole of the semiconductor device. The contrast of the secondary electron image and the beam pass current depend on the aspect ratio of the hole such as the contact hole. The reference contrast of the secondary electron image of the opening and the reference beam pass current of the standard test device are made closer to the actual contrast of the secondary electron image of the hole such as the contact hole and the actual reference beam pass current. An accuracy in evaluation or measurement to thickness of the residual film by use of the standard test device is also improved.

It is also preferable that the at least insulating layer has the same dielectric constant as the film in which the hole of the semiconductor device is formed. The contrast of the secondary electron image and the beam pass current depend upon electric properties as the dielectric constant of the film in which the hole such as the contact hole is formed, wherein the residual film is a part of the film in which the hole such as the contact hole is formed and thus the material of the residual film is the same as the film having the hole such as the contact hole. The contrast of the secondary electron image and the beam pass current also depend upon electric properties as the dielectric constant of the insulating film having the opening of the standard test device. Therefore, the insulating layer having the opening of the standard test device has the same dielectric constant as the film in which the hole such as of the semiconductor device is formed, so that the reference contrast of the secondary electron image of the opening and the reference beam pass current of the standard test device are made closer to the actual contrast of the secondary electron image of the hole such as the contact hole and the actual reference beam pass current. An accuracy in evaluation or measurement to thickness of the residual film by use of the standard test device is also improved.

It is possible that the base surface of the standard test device comprises a surface of a substrate. This substrate may be any kinds of the substrates such as semiconductor substrates and insulating substrates. This standard test device is applicable to when the hole such as the contact hole is formed on the substrate surface, so that the reference contrast of the secondary electron image of the opening and the reference beam pass current of the standard test device are made closer to the actual contrast of the secondary electron image of the hole such as the contact hole and the actual reference beam pass current. An accuracy in evaluation or measurement to thickness of the residual film by use of the standard test device is also improved.

It is possible that the base surface of the standard test device comprises a surface of a diffusion region having the same kind of impurity and impurity concentration as a diffusion region on which the hole of the semiconductor device is formed. The contrast of the secondary electron image and the beam pass current also depend upon the presence of the diffusion region on which the contact hole is formed. This standard test device is applicable to when the hole such as the contact hole is formed on the surface of the diffusion region over the substrate, so that the reference contrast of the secondary electron image of the opening and the reference beam pass current of the standard test device are made closer to the actual contrast of the secondary electron image of the hole such as the contact hole and the actual reference beam pass current. An accuracy in evaluation or measurement to thickness of the residual film by use of the standard test device is also improved.

It is possible that the base surface of the standard test device comprises a surface of a well region having the same kind of impurity and impurity concentration as a diffusion region on which the hole of the semiconductor device is formed. The contrast of the secondary electron image and the beam pass current also, depend upon the presence of the well region on which the contact hole is formed. This standard test device is applicable to when the hole such as the contact hole is formed on the surface of the well region over the substrate, so that the reference contrast of the secondary electron image of the opening and the reference beam pass current of the standard test device are made closer to the actual contrast of the secondary electron image of the hole such as the contact hole and the actual reference beam pass current. An accuracy in evaluation or measurement to thickness of the residual film by use of the standard test device is also improved.

It is possible that the base surface of the standard test device comprises a surface of an active region which is the same as an active region on which the hole of the semiconductor device is formed. The contrast of the secondary electron image and the beam pass current also depend upon the presence of the active region on which the contact hole is formed. This standard test device is applicable to when the hole such as the contact hole is formed on the surface of the active region over the substrate, so that the reference contrast of the secondary electron image of the opening and the reference beam pass current of the standard test device are made closer to the actual contrast of the secondary electron image of the hole such as the contact hole and the actual reference beam pass current. An accuracy in evaluation or measurement to thickness of the residual film by use of the standard test device is also improved.

It is also possible that the base surface of the standard test device comprises a surface of a silicon-on-insulator substrate which is the same as a silicon-on-insulator substrate on which the hole of the semiconductor device is formed. The contrast of the secondary electron image and the beam pass current also depend upon the presence of the single crystal silicon layer over an insulator over the semiconductor substrate. This standard test device is applicable to when the hole such as the contact hole is formed on the surface of the single crystal silicon layer of the silicon-on-insulator substrate, so that the reference contrast of the secondary electron image of the opening and the reference beam pass current of the standard test device are made closer to the actual contrast of the secondary electron image of the hole such as the contact hole and the actual reference beam pass current. An accuracy in evaluation or measurement to thickness of the residual film by use of the standard test device is also improved.

It is possible that the base surface of the standard test device comprises a top surface of a substrate having a bottom surface on which an insulating layer is provided. The contrast of the secondary electron image and the beam pass current also depend upon the presence of the insulating layer on the bottom of the substrate. This standard test device is applicable to when the hole such as the contact hole is formed on the top surface of the substrate having the bottom surface on which the insulating layer is provided, so that the reference contrast of the secondary electron image of the opening and the reference beam pass current of the standard test device are made closer to the actual contrast of the secondary electron image of the hole such as the contact hole and the actual reference beam pass current. An accuracy in evaluation or measurement to thickness of the residual film by use of the standard test device is also improved.

It is possible that the base surface of the standard test device comprises a top surface of an electrically conductive film such as a metal interconnection formed on a substrate. The contrast of the secondary electron image and the beam pass current also depend upon the presence of the electrically conductive film formed on the substrate. This standard test device is applicable to when the hole such as the contact hole is formed on the top surface of the electrically conductive film formed on the substrate. The hole such as the contact hole or the via hole is formed on the metal interconnection. The reference contrast of the secondary electron image of the opening and the reference beam pass current of the standard test device are made closer to the actual contrast of the secondary electron image of the hole such as the contact hole and the actual reference beam pass current. An accuracy in evaluation or measurement to thickness of the residual film by use of the standard test device is also improved.

It is also possible to further comprise: a fluoro-carbon film sandwiched between the insulating film and the dummy film. If the hole such as the contact hole is formed by the reactive ion etching, fluoro-carbon may be adhered on the bottom and side wall of the contact hole. The adhered fluoro-carbon provides an influence to the etching property. In order to determine optimum etching conditions, it is also important to determine or measure a thickness of the adhered fluoro-carbon film on the bottom and side wall of the contact hole. The use of the standard test device having the fluoro-carbon film having the known thickness makes it possible to evaluate or measure the thickness of the adhered fluoro-carbon film on the bottom and side wall of the contact hole.

It is possible that the at least insulating film of the standard test device has a plurality of the openings. The following descriptions will be made when the plurality of the openings are formed.

It is possible that the at least dummy film extends on a selected region of the base surface, whilst the insulating film extends over the at least dummy film and an unselected region of the base surface, and that at least first one of the plural openings is provided over the dummy film and at least second one of the plural openings is provided over the unselected region of the base surface. The first one of the openings corresponds to the contact hole having the bottom on which the residual film resides. The second one of the openings corresponds to the contact hole having the bottom on which no residual film resides. The use of the standard test device may obtain both reference contrasts of the secondary electron images of the opening having the dummy film and the opening free of dummy film, whereby it is possible to obtain the reference contrasts of the secondary electron images to be compared with the contact hole free of any residual film and the defective contact hole having the residual film.

It is possible that the first one and second one of the plural openings have the same plane size and are different in depth and aspect ratio from each other. The contrast of the secondary electron image and the beam pass current depend on the aspect ratio of the hole such as the contact hole. This standard test device has the openings having various aspect ratios. Thus, the standard test device is applicable to various contact holes having the various aspect ratios. The contrast of the secondary electron image and the beam pass current of the opening having the same or closest aspect ratio are used as optimum ones. The reference contrast of the secondary electron image of the optimum opening having the same or closest aspect ratio and the reference beam pass current of the standard test device are made closer to the actual contrast of the secondary electron image of the hole such as the contact hole and the actual reference beam pass current. An accuracy in evaluation or measurement to thickness of the residual film by use of the standard test device is also improved.

It is possible that a plurality of the dummy films are provided so that an upper one of the plural dummy films is laminated on a selected region of a lower one of the plural dummy films, and that at least first one of the plural openings is provided over an uppermost one of the plural dummy films, and at least other one of the plural openings is provided over an unselected region of each of lower ones of the plural dummy films than the uppermost one. The standard test device has the openings different in aspect ratio from each other. The contrast of the secondary electron image and the beam pass current depend on the aspect ratio of the hole such as the contact hole. This standard test device has the openings having various aspect ratios. Thus, the standard test device is applicable to various contact holes having the various aspect ratios. The contrast of the secondary electron image and the beam pass current of the opening having the same or closest aspect ratio are used as optimum ones. The reference contrast of the secondary electron image of the optimum opening having the same or closest aspect ratio and the reference beam pass current of the standard test device are made closer to the actual contrast of the secondary electron image of the hole such as the contact hole and the actual reference beam pass current. An accuracy in evaluation or measurement to thickness of the residual film by use of the standard test device is also improved.

It is further possible that a plurality of the dummy films are provided so that an upper one of the plural dummy films is laminated on a selected region of a lower one of the plural dummy films, and that at least first one of the plural openings is provided over an uppermost one of the plural dummy films, and at least other one of the plural openings is provided over an unselected region of each of lower ones of the plural dummy films than the uppermost one, and further that the first other ones of the plural openings have the same plane size and are different in depth and aspect ratio from each other. The standard test device has the openings different in aspect ratio from each other. The contrast of the secondary electron image and the beam pass current depend on the aspect ratio of the hole such as the contact hole. This standard test device has the openings having various aspect ratios. Thus, the standard test device is applicable to various contact holes having the various aspect ratios. The contrast of the secondary electron image and the beam pass current of the opening having the same or closest aspect ratio are used as optimum ones. The reference contrast of the secondary electron image of the optimum opening having the same or closest aspect ratio and the reference beam pass current of the standard test device are made closer to the actual contrast of the secondary electron image of the hole such as the contact hole and the actual reference beam pass current. An accuracy in evaluation or measurement to thickness of the residual film by use of the standard test device is also improved.

It is possible that a plurality of the dummy films are provided so that an upper one of the plural dummy films is laminated on a selected region of a lower one of the plural dummy films, and that at least first one of the plural openings is provided over an uppermost one of the plural dummy films, and at least other one of the plural openings is provided over an unselected region of each of lower ones of the plural dummy films than the uppermost one, and further that a lowest one of the plural dummy films extends on an entire region of the base surface. The standard test device has the openings different in aspect ratio from each other. The contrast of the secondary electron image and the beam pass current depend on the aspect ratio of the hole such as the contact hole. This standard test device has the openings having various aspect ratios. Thus, the standard test device is applicable to various contact holes having the various aspect ratios. The contrast of the secondary electron image and the beam pass current of the opening having the same or closest aspect ratio are used as optimum ones. The reference contrast of the secondary electron image of the optimum opening having the same or closest aspect ratio and the reference beam pass current of the standard test device are made closer to the actual contrast of the secondary electron image of the hole such as the contact hole and the actual reference beam pass current. An accuracy in evaluation or measurement to thickness of the residual film by use of the standard test device is also improved.

It is possible that a plurality of the dummy films are provided so that an upper one of the plural dummy films is laminated on a selected region of a lower one of the plural dummy films, and that at least first one of the plural openings is provided over an uppermost one of the plural dummy films, and at least other one of the plural openings is provided over an unselected region of each of lower ones of the plural dummy films than the uppermost one, and further that a lowest one of the plural dummy films extends on a selected region of the base surface so that the at least first one of the plural openings is provided over the uppermost one of the plural dummy films, and at least a second one of the plural openings is provided over the unselected region of the base surface, and further the at least other one of the plural openings is provided over the unselected region of each of the lower ones of the plural dummy films than the uppermost one. The use of the standard test device may obtain both reference contrasts of the secondary electron images of the opening having the dummy film and the opening free of dummy film, whereby it is possible to obtain the reference contrasts of the secondary electron images to be compared with the contact hole free of any residual film and the defective contact hole having the residual film. The standard test device has the openings different in aspect ratio from each other. The contrast of the secondary electron image and the beam pass current depend on the aspect ratio of the hole such as the contact hole. This standard test device has the openings having various aspect ratios. Thus, the standard test device is applicable to various contact holes having the various aspect ratios. The contrast of the secondary electron image and the beam pass current of the opening having the same or closest aspect ratio are used as optimum ones. The reference contrast of the secondary electron image of the optimum opening having the same or closest aspect ratio and the reference beam pass current of the standard test device are made closer to the actual contrast of the secondary electron image of the hole such as the contact hole and the actual reference beam pass current. An accuracy in evaluation or measurement to thickness of the residual film by use of the standard test device is also improved.

It is possible that the at least dummy film has an individually predetermined constant thickness at least around each of the plural openings. In this case, it is possible that the individually predetermined constant thickness is the same for all of the plural openings. In this case, it is also possible that the at least dummy film has the predetermined constant thickness throughout an entire region thereof.

It is also possible that the at least dummy film comprises a plurality of subordinate regions which are made of different materials from each other, and at least one of the plural openings is provided on each of the plural subordinate regions. The openings are formed on different material base surfaces, so that the standard test device is applicable to various cases when the hole such as the contact hole is formed on the various kinds base surfaces such as the semiconductor substrate, the insulating substrate, the diffusion region, the well region, and the silicon-on-insulator substrate. The contrast of the secondary electron image and the beam pass current also depend upon the material of the base surface, such as the semiconductor substrate, the insulating substrate, the diffusion region, the well region, and the silicon-on-insulator substrate. This standard test device is applicable to when the hole such as the contact hole is formed on the surface of the various materials, so that the reference contrast of the secondary electron image of the opening and the reference beam pass current of the standard test device are made closer to the actual contrast of the secondary electron image of the hole such as the contact hole and the actual reference beam pass current. An accuracy in evaluation or measurement to thickness of the residual film by use of the standard test device is also improved.

It is possible that the plural openings are distributed so uniformly that a plane distribution density of the plural openings varies over position. In the actual semiconductor devices, the contact holes are provided at various distances and the density of the contact holes varies over position of the semiconductor device. The contrast of the secondary electron image and the beam pass current also depend upon the distribution of the contact holes. This standard test device is applicable to when the hole such as the contact hole is formed at various density of distribution. The opening formed at the same or closet density of distribution to the actual distribution density of the hole such as the contact hole is selected, so that the reference contrast of the secondary electron image of the opening and the reference beam pass current of the standard test device are made closer to the actual contrast of the secondary electron image of the hole such as the contact hole and the actual reference beam pass current. An accuracy in evaluation or measurement to thickness of the residual film by use of the standard test device is also improved.

It is also possible that the insulating layer of the standard test device comprises a plurality of subordinate parts which are different in thickness from each other, and at least one of the plural openings is provided in each of the plural subordinate parts. The standard test device has the openings different in aspect ratio from each other. The contrast of the secondary electron image and the beam pass current depend on the aspect ratio of the hole such as the contact hole. This standard test device has the openings having various aspect ratios. Thus, the standard test device is applicable to various contact holes having the various aspect ratios. The contrast of the secondary electron image and the beam pass current of the opening having the same or closest aspect ratio are used as optimum ones. The reference contrast of the secondary electron image of the optimum opening having the same or closest aspect ratio and the reference beam pass current of the standard test device are made closer to the actual contrast of the secondary electron image of the hole such as the contact hole and the actual reference beam pass current. An accuracy in evaluation or measurement to thickness of the residual film by use of the standard test device is also improved. In this case, it is possible that the plural openings have the same plane size and are different in depth and aspect ratio from each other.

It is also possible that a plurality of the standard test devices makes a set, and the plural standard test devices are different in thickness of the insulating film.

It is possible that the insulating film of the standard test device comprises a resin film having a sensitivity to an ultraviolet ray, and the resin film has been subjected to a selective hardening process. The insulating film having the opening may be made of a resin such as a resin having a sensitivity to an ultraviolet ray. If the insulating film is made of such photo-sensitive resin, then the opening may be formed by patterning the photo-sensitive resin film without providing any substantive damage to the dummy film underlying the photo-sensitive resin film, even the dummy film is extremely thin such as a few angstroms. The limitation of the plane size of the opening in the photo-sensitive resin depends upon the limitation of the lithography such as photo-lithography. Even if the size of the contact hole is extremely small, then the opening size may be adopted to be identical with the contact hole.

It is possible that the insulating film comprises a resin film having a sensitivity to an X-ray, and the resin film has been subjected to a selective hardening process. The insulating film having the opening may be made of a resin such as a resin having a sensitivity to an X-ray. If the insulating film is made of such photo-sensitive resin, then the opening may be formed by patterning the photo-sensitive resin firm without providing any substantive damage to the dummy film underlying the photo-sensitive resin film, even the dummy film is extremely thin such as a few angstroms. The limitation of the plane size of the opening in the photo-sensitive resin depends upon the limitation of the lithography such as X-ray lithography. Even if the size of the contact hole is extremely small, then the opening size may be adopted to be identical with the contact hole.

It is possible that the insulating film of the standard test device comprises a resin film having a sensitivity to an electron beam, and the resin film has been subjected to a selective hardening process. The insulating film having the opening may be made of a resin such as a resin having a sensitivity to an electron beam. If the insulating film is made of such photo-sensitive resin, then the opening may be formed by patterning the photo-sensitive resin film without providing any substantive damage to the dummy film underlying the photo-sensitive resin film, even the dummy film is extremely thin such as a few angstroms. The limitation of the plane size of the opening in the photo-sensitive resin depends upon the limitation of the lithography such as electron beam lithography. Even if the size of the contact hole is extremely small, then the opening size may be adopted to be identical with the contact hole.

It is possible that the dummy film comprises one insulating material of selected from the group consisting of SiO2, SiN, TiN, TaN, ONO, SiON, spin-on-glass (SOG), silica based inorganic substances, silica based organic substances, and ferromagnetic substances It is possible that the dummy film comprises one material of selected from the group consisting of Ti, W, Mo, Al, Au, Pt, Co, Ir, metal oxides, silicides, oxides of the silicides, intermetallic compounds, organic materials, oxide superconductance materials.

The second present invention provides a method of testing a hole of a semiconductor device by use of the standard test device of the first present invention described above, wherein the method comprising the steps of: irradiating an electron beam onto the hole; measuring at least any one of a value of a secondary electron current emitted from the hole and a value of a beam pass current passing from a bottom of the hole through a residual film residing on a bottom of the hole of the semiconductor device; referring to a reference table on the basis of the measured value to evaluate a thickness of the residual film, wherein the reference table shows correspondences between a thickness of the dummy film of the standard test device and at least any one of a value of a secondary electron current emitted from the at least one opening of the standard test device upon irradiation of an electron beam onto the at least one opening and a value of a beam pass current passing from a bottom of the at least one opening through the base surface of the standard test device.

The third present invention provides a method of testing a hole of a semiconductor device by use of the standard test device of the first present invention described above, wherein the method comprising the steps of: irradiating an electron beam onto the hole to obtaining a secondary electron image of the hole; and comparing a first contrast of the secondary electron image of the hole to a second contrast of a secondary electron image of the at least one opening of the standard test device, which has been already obtained by having irradiated an electron beam onto the at least one opening, in order to determine a thickness of a residual film residing on a bottom of the hole of the semiconductor device.

The fourth present invention provides a method of testing a hole of a semiconductor device by use of the standard test device of the first present invention described above, wherein the method comprises the steps of: irradiating an electron beam onto the hole to obtaining a beam pass current passing from a bottom of the hole through a residual film residing on a bottom of the hole of the semiconductor device; and comparing a first value of a beam pass current of the hole to a second value of a beam pass current of the at least one opening of the standard test device, which has been already obtained by having irradiated an electron beam onto the at least one opening, in order to determine a thickness of the residual film.

The fifth present invention provides a system for testing a hole of a semiconductor device by use of the standard test device of the first present invention described above, wherein the system includes: an electron beam irradiator for irradiating an electron beam onto the hole; a measuring device for measuring at least any one of a value of a secondary electron current emitted from the hole and a value of a beam pass current passing from a bottom of the hole through a residual film residing on a bottom of the hole of the semiconductor device; and a reference unit having a reference table to be referred on the basis of the measured value to evaluate a thickness of the residual film, wherein the reference table shows correspondences between a thickness of the dummy film of the standard test device and at least any one of a value of a secondary electron current emitted from the at least one opening of the standard test device upon irradiation of an electron beam onto the at least one opening and a value of a beam pass current passing from a bottom of the at least one opening through the base surface of the standard test device.

The sixth present invention provides a system for testing a hole of a semiconductor device by use of the standard test device of the first present invention described above, wherein the system includes: an electron beam irradiator for irradiating an electron beam onto the hole to obtaining a secondary electron image of the hole; a memory device for storing data about a secondary electron image of the at least one opening of the standard test device; a comparing unit for comparing a first contrast of the secondary electron image of the hole to the second contrast of the secondary electron image of the at least one opening of the standard test device, in order to determine a thickness of a residual film residing on a bottom of the hole of the semiconductor device.

The seventh present invention provides a system for testing a hole of a semiconductor device by use of the standard test device of the first present invention described above, wherein the system includes: an electron beam irradiator for irradiating an electron beam onto the hole to obtaining a beam pass current passing from a bottom of the hole through a residual film residing on a bottom of the hole of the semiconductor device; a memory device for storing data about a beam pass current of the at least one opening of the standard test device; and a comparing unit for comparing a first value of a beam pass current of the hole to a second value of a beam pass: current of the at least one opening of the standard test device, in order to determine a thickness of the residual film.

The eighth present invention provides a method of forming a standard test device. The method comprises the steps of: forming at least a dummy film having at least one thickness uniform region having a predetermined constant thickness on a base surface; applying a resin film having any one of sensitivities to an ultraviolet ray, an X-ray and an electron beam on the at least a dummy film; and subjecting the resin film to a first selective hardening process to form at least an opening in the resin film.

It is possible that the first selective hardening process includes the following steps of: carrying out a pre-baking to the resin film; exposing the resin film to any one of an ultraviolet ray, an X-ray and an electron beam on the at least a dummy film; and carrying out a development to the resin film to form the at least an opening.

It is further possible that the first selective hardening process further includes the following step of: carrying out a post-baking to the resin film after the development has been carried out.

The ninth present invention provides a system of measuring a thickness of a film over a substrate. The system comprises: an electron beam irradiator for irradiating an electron beam onto the film to cause a beam path current; a detecting device for detecting a beam pass current having passed through the film; a first memory device for storing inter-relating data between a reference thickness and a reference beam pass current obtained by having irradiated an electron beam onto a dummy film of a standard test device; and a converting device for converting the detected beam pass current into a thickness of the film with reference to the stored inter-relating data.

It is possible that the detecting device comprises an electrode provided in contact with the substrate for capturing the beam pass current from the substrate; and a detector connected to the electrode for detecting the beam pass current.

It is also possible that the detector has an amplifier for amplifying the detected beam pass current.

It is also possible that the detector has a differential amplifier for eliminating an off-set voltage due to a leakage of current other than the beam pass current.

It is also possible that the electron beam irradiator has an electron beam scanner for scanning the electron beam over the film, and the system further comprises a second memory device connected to the electron beam scanner and the detecting device for storing relationships of a scanning position of the electron beam scanner and the detected beam pass current.

It is also possible to further comprise a secondary electron current detector for detecting a secondary electron current emitted from the film on which the electron beam has been irradiated by the electron beam irradiator.

The tenth present invention provides a method of measuring a thickness of a film over a substrate. The method comprises the steps of: irradiating an electron beam onto the film to cause a beam pass current; detecting the beam pass current having passed through the film; and converting the detected beam pass current into a thickness of the film with reference to inter-relating data between a reference thickness and a reference beam pass current obtained by having irradiated an electron beam onto a dummy film of a standard test device.

It is possible that the beam pass current is captured from the substrate by an electrode provided in contact with the substrate, and then detected by a detector connected to the electrode.

It is further possible that the beam pass current is further amplified by an amplifier.

It is also possible that an off-set voltage due to a leakage of current is eliminated from the beam pass current by a differential amplifier.

It is also possible that the electron beam is scanned over the film by an electron beam scanner, and relationships of a scanning position of the electron beam scanner and the detected beam pass current are used to obtain a distribution in thickness of the film.

The eleventh present invention provides a method of testing a semiconductor wafer having a plurality of primary divided regions, each primary divided region having a plurality of contact holes. The method comprises the steps of: irradiating an electron beam onto each of the plurality of primary divided regions to cause beam pass currents having passed through each of the primary divided regions; measuring the beam pass currents; and comparing the measured beam pass currents to a threshold value to estimate a ratio of defective contact holes to a sub-total number of the contact holes in each of the primary divided regions.

It is further possible that each of the primary divided regions has a similar size to as a semiconductor chip. It is further more possible that each of the primary divided regions has a similar size to a semiconductor device integrated on a semiconductor chip. It is also possible that the primary divided regions are allocated with primary identification numbers to identify each of the primary divided regions.

It is also possible that the primary divided regions are ordered in order of measured values of the beam pass currents, so that the contact holes are tested one by one for the ordered primary divided regions in the order.

It is also possible that the electron beams are irradiated onto separated ones selected from the primary divided regions to cause beam pass currents having passed through each of the separated ones for measuring the beam pass currents and subsequently comparing the measured beam pass currents to a threshold value to estimate a ratio of defective contact holes to a total number of the contact holes in each of the separated ones.

It is also possible that a dose of the electron beam varies depending upon the number of the contact holes in each of the primary divided regions.

It is further possible that the number of the contact holes is confirmed by recognizing each of the primary divided regions with reference to an electron beam irradiation position, a semiconductor wafer position, and an information about layouts of semiconductor integrated circuits of the semiconductor wafer.

It is also possible that the contact holes are tested for the primary divided regions in order of the height of the estimated ratio of defective contact holes to a total number of the contact holes.

It is also possible that testing orders of the primary divided regions are given with different weights so that closer one of the primary divided regions to a center position of the semiconductor wafer is given with a larger weight, whilst closer one of the primary divided regions to a peripheral position of the semiconductor wafer is given with a smaller weight.

It is also possible that testing orders of the primary divided regions are given with different weights so that closer one of the primary divided regions to a contact position contacting with a wafer carrier is given with a larger weight.

It is also possible to further comprise the step of obtaining a bit map in correspondence with the beam pass currents having passed through the primary divided regions.

It is also possible that if the estimated ratio of the defective contact holes to the sub-total number of the contact holes in each of the primary divided regions is above a threshold value, then the number of the contact holes is counted and testing of the contact holes is discontinued for currently tested one of the primary divided regions.

It is also possible to further comprise the steps of: obtaining a distribution of the beam pass currents having passed through the primary divided regions; calculating both an average and a standard deviation of the beam pass currents on the basis of the distribution for detecting variation in manufacturing process of the semiconductor wafer.

It is further possible that if the variation in manufacturing process is above a threshold value, an alert signal is generated for giving a notice of appearance of abnormal state in the manufacturing process.

It is also possible that the method comprises the steps of: irradiating an electron beam onto each of the plurality of secondary divided regions to cause beam pass currents having passed through each of the secondary divided regions; measuring the beam pass currents; and comparing the measured beam pass currents to a threshold value to estimate a ratio of defective contact holes to a sub-total number of the contact holes in each of the secondary divided regions.

It is further possible that the secondary divided regions are allocated with secondary identification numbers to identify each of the secondary divided regions.

It is also possible that the secondary divided regions are ordered in order of measured values of the beam pass currents, so that the contact holes are tested one by one for the ordered secondary divided regions in the order.

It is also possible that the contact holes are tested for the secondary divided regions in order of the height of the estimated ratio of defective contact holes to a total number of the contact holes.

It is also possible that if the estimated ratio of the defective contact holes to the sub-total number of the contact holes in each of the secondary divided regions is above a threshold value, then the number of the contact holes is counted and testing of the contact holes is discontinued for currently tested one of the secondary divided regions.

It is also possible to further comprise the steps of: obtaining a distribution of the beam pass currents having passed through the secondary divided regions; calculating both an average and a standard deviation of the beam pass currents on the basis of the distribution for detecting variation in manufacturing process.

It is also possible that if the variation in manufacturing process is above a threshold value, an alert signal is generated for giving a notice of appearance of abnormal state in the manufacturing process.

PREFERRED EMBODIMENT

First Embodiment:

A first embodiment according to the present invention will be described in detail with reference to the drawings. FIG. 1 is a fragmentary cross sectional elevation view illustrative of a novel standard test device of a first embodiment in accordance with the present invention. The novel standard test device has a supporting substrate 10. A dummy film 12 is provided on a top surface of the supporting substrate 10. A photo-sensitive resin layer 14 having openings 16 is provided on the dummy film 12. Bottoms 18 of the openings 16 comprise parts of the top surface of the dummy film 12. The dummy film 12 of the standard test device corresponds to a residual film of a contact hole of a semiconductor device. The openings 16 of the standard test device correspond to the contact holes of the semiconductor device. The dummy film 12 has an accurately controlled thickness.

The supporting substrate 10 of the standard test device is preferably made of the same material as the supporting substrate of the semiconductor device. In this embodiment, the supporting substrate 10 is made of a single crystal silicon. Notwithstanding, polysilicon, glass and quartz and sapphire may be used for the supporting substrate 10.

The dummy film 12 of the standard test device is preferably made of the same material as the residual film on the bottom of the contact hole of the semiconductor device. In this embodiment, the dummy film 12 is made of silicon oxide.

The resin layer 14 has a thickness which corresponds to the depth of the contact hole of the semiconductor device. The thickness of the resin layer 14 may be, for example, in the range of a few micrometers to 1000 micrometers. The aerial size of the openings 16 preferably the sums as the contact hole. The aspect ratio of the openings 16 is also preferably the same as the contact hole. The diameter of the opening 16 may be in the range of 0.1 micrometer to 0.5 micrometers.

Figure 2A:
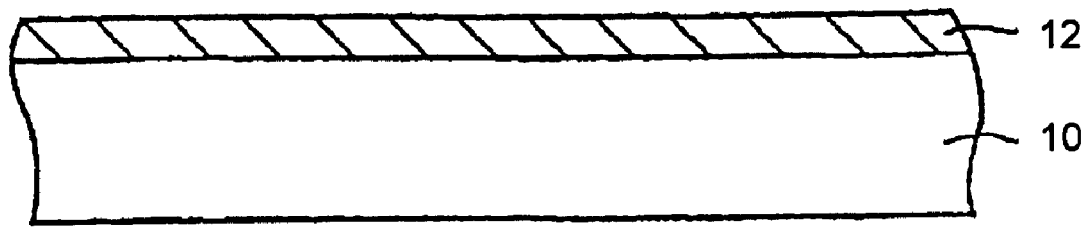
FIGS. 2A through 2C are fragmentary cross sectional elevation views illustrative of a novel method of forming a novel standard test device of FIG. 1 in a first embodiment in accordance with the present invention.
Figure 2B:
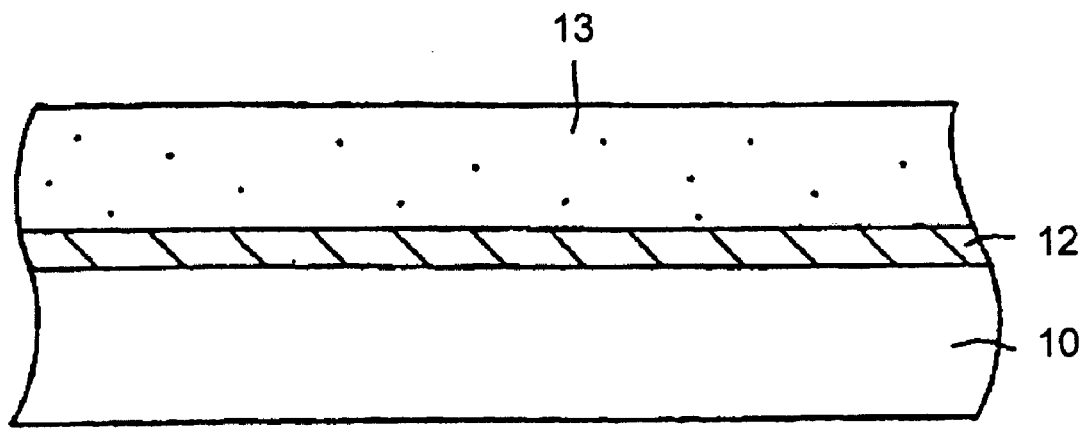
Figure 2C:
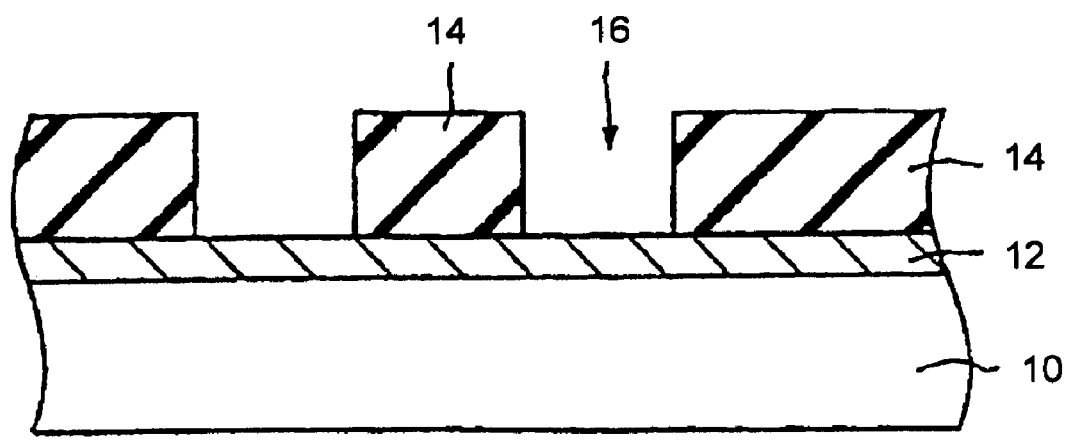

The novel standard test device shown in FIG. 1 may be formed as follows. FIGS. 2A through 2C are fragmentary cross sectional elevation views illustrative of a novel method of forming a novel standard test device of FIG. 1 in a first embodiment in accordance with the present invention.

With reference to FIG. 2A, a cleaning is made to the surface of the supporting substrate 10. The dummy film 12 of silicon oxide is formed on the surface of the supporting substrate 10. This silicon oxide film may be formed by a thermal oxidation method, wherein a dry oxygen as introduced into an electric furnace for oxidation of silicon. The electric furnace is maintained at a temperature in the rang of 800–850.degree. C., for heating the supporting substrate 10 form time period of a few minutes to several tens of minutes, whereby a silicon oxide film is formed on the supporting substrate 10. The silicon oxide film has a thickness in the range of a few angstroms to several tens of angstroms. The accuracy in thickness of the silicon oxide film is of angstrom order. It is easy to make contact through a thickness of not more than about 80 angstroms which corresponds to an escape distance. The thickness of the silicon oxide film is measured in angstroms order accuracy by a highly accurate thickness measuring device such as ellipsometry.

Alternatively, it is also possible that the supporting substrate 10 is dipped into a mixture liquid of ammonium hydroxide and either hydrogen peroxide or hydrochloric acid so as to case a chemical reaction of hydrogen peroxide with silicon of the surface of the supporting substrate 10 thereby forming a silicon oxide film. The temperature of the formation of the silicon oxide film is much lower than the above thermal oxidation method, for which reason it is possible to form the oxide film uniformly over the entire region of the wafer at a high accuracy in thickness in the range of ±1 angstrom.

With reference to FIG. 2B, the photo-sensitive resin film 13 is applied on the dummy film 12 of silicon oxide. The photo-sensitive resin film 13 has an accurately controlled thickness. The photo-sensitive resin film 13 may be applied by a spin coating method.

As the photo-sensitive resin material for the photo-sensitive resin film 13, there are available novolak resins, chemical sensitizing resists, acrylic resins, rubber resins, aliphatic conjugate diene, carboxylic acid containing polyamide resins, polyvinyl phenol resins, polyhydroxy styrene resins, bis-phenol A bromide epoxy resins, polycarbonate diol denaturation dicarboxylic acid resins, $\alpha$, $\beta$-unsaturated carboxyl group containing monomer resins, co-polymers consisting of vinyl pyrolidone and vinyl acetate, polybenzooxazole resins, polytetramethyleneglycol denaturation dicarboxylic acid resins, photo-sensitive diazoquinone compound resins, polyamic acid compound resins, and imide resins.

With reference to FIG. 2C, selected parts of the applied resin film 13 are subjected to a selective hardening process to form the openings 16 which penetrate the resin films 14. The hardening process is carried out as follows. The applied resin 13 is pre-baked by an oven at a temperature of 80° C., wherein nitrogen is purged. The pre-baked resin 13 is then exposed to an ultraviolet ray. A development to the exposed resin is then carried out.

In place of the ultraviolet ray, the X-ray exposure or electron beam exposure may also be available.

It is further preferable to form an anti-reflecting film on each of the top and bottom surfaces of the resin film.

It is important that the resin 14 has a high dimensional stability to obtain a high dimensional stability of the openings 16. It is therefore to use a specific developing solution which has a small swelling to the photo-resistive resin 13. There are available, for example, a tetra-methyl amine hydroxide solution, ternary or quaternary amine compounds such as choline, naphthoquinone diazide, 1-methoxy-2-propanol, or surfactants if any.

After the development has been carried out, the developing liquid is rinsed with the following rinsing solution. As the rinsing solution, there are available dichloromethane, tetrahydrofuran, n-pentane, isohexane, a mixture of 3-methylpentane and neohexane, 2,3-dimethylbutane, acetone, ethyl ether, methyl lactate. After the rinsing process, a post-bake process is carried out at a temperature of not less than 120° C. for hardening the resin thereby forming the resin 14 which has a high dimensional stability.

It is also possible to carry out optionally an UV hardening by irradiating a high energy ultraviolet ray having a wavelength of not more than 300 nanometers or a short time plasma treatment for baking the surface of the resin 14.

The standard test devices are formed on the wafer concurrently. If any, it is possible to dice the wafer to divide the same into plural chips so as to place the standard test device chips near the test semiconductor devices.

A set of the standard test devices that differ in thickness of the dummy film is prepared, wherein the thickness of the dummy film is varied in the range from a few angstroms to several hundreds angstroms in increment of several tens of angstroms step.

An electron beam is irradiated onto the opening 16 of the standard test device to cause a secondary electron current to be emitted from the opening 16. The current value of the emitted secondary electron is measured to prepare a reference table which shows correspondences between the secondary electron current and the thickness of the dummy film. The above measuring process is carried out for every standard test devices different in thickness of the dummy film to determine inter-relation between various thicknesses and corresponding secondary electron currents.

The electron beam is also irradiated onto the contact hole of the semiconductor device under the same condition as the electron beam irradiation onto the opening to cause a secondary electron current to be emitted from the contact hole. The current value of the emitted secondary electron is measured. With reference to the reference table, the thickness of the residual film on the bottom of the contact hole is determined.

If, for example, the measured secondary electron current of the contact hole is the same as the measured secondary electron current of the opening of the standard test device having the dummy film having the thickness of 10 angstroms, then the thickness of the residual film on the bottom of the contact hole is presumed to be 10 angstroms. If the residual film is an insulator, then the beam pass current having passed through the residual film is decreased in proportion to the increase in thickness of the residual film.

The above measurement and comparison or reference processes are required to be carried out at high speed, for which reason it is preferable to use a computer, where the computer reads out the corresponding thickness of the residual film to the secondary electron current of the standard test device on the basis of the reference table. It is also possible that the computer operates to judge whether or not the contact hole is defective with reference to the estimated thickness of the residual film.

The standard test devices are stored for calibration to variations of the semiconductor devices. Since the contrast of the secondary electron image largely depends upon the surface state of the standard test device, it is preferable to store the standard test device in vacuum at a low temperature in order to prevent deterioration of the photo-sensitive resin and the dummy film.

The above novel standard test device of this embodiment provides the following effects. In prior art, the actually available method to measure the thickness of the residual film on the bottom of the contact hole is only a sectioned image of the residual film by use of the transmission electron microscope (TEM). In accordance with the present invention, however, in order to evaluate or estimate the thickness of the residual film on the bottom of the contact hole, the standard test device is used which has the dummy film having the accurately controlled thickness and the openings, wherein the dummy film corresponds to the residual film and the openings correspond to the contact holes. The necessary time for measurement of the thickness of the residual film is shortened by use of the standard test device as compared to the conventional method of using the TEM observation.

When the sample semiconductor device is prepared, the accurate thickness of the residual film on the bottom of the contact hole may be measured to determine whether or nor the contact hole is defective, whereby it is possible to determine whether or nor the semiconductor device is defective.

The standard test device makes it possible to judge a large number of the contact holes with a shorten time by quick measurement to the residual films on the bottoms of the contact holes. A sequential measurement is possible to the thickness of the residual films on the bottoms of the contact holes, for which reason it is possible to check variation in manufacturing process and any slight trouble with the etching system.

Figure 3:
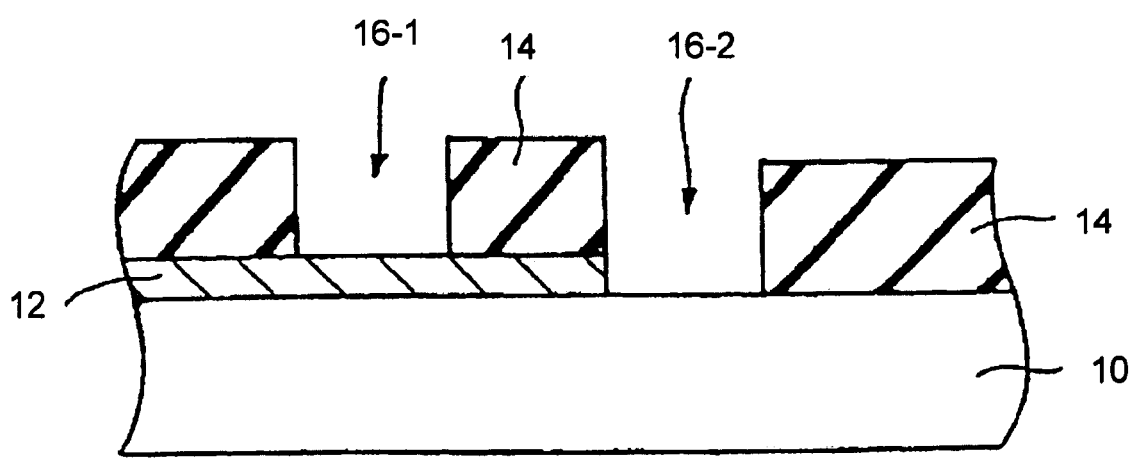
FIG. 3 is a fragmentary cross sectional elevation view illustrative of a novel standard test device of a second embodiment in accordance with the present invention.

Second Embodiment:

A second embodiment according to the present invention will be described in detail with reference to the drawings. The descriptions will focus on differences of this embodiment from the first embodiment to avoid redundancy descriptions. FIG. 3 is a fragmentary cross sectional elevation view illustrative of a novel standard test device of a second embodiment in accordance with the present invention. In the above first embodiment, the dummy film 12 extends over the entire region of the top surface of the supporting substrate 10. In this second embodiment, however, the dummy film 12 extends but only on a selected region of the top surface of the supporting substrate 10, so that the first opening is formed over the dummy film whilst the second opening is formed on the top surface of the substrate.

The novel standard test device has a supporting substrate 10. A dummy film 12 is provided on a selected region of a top surface of the supporting substrate 10. A photo-sensitive resin layer 14 having first and second openings 16-1 and 16-2 are provided on the dummy film 12 and on an unselected region of the top surface of the supporting substrate 10. A bottom of the first opening 16-1 comprises a part of the top surface of the dummy film 12. A bottom of the second opening 16-2 comprises a part of the unselected region of the top surface of the supporting substrate 10. The dummy film 12 of the standard test device corresponds to a residual film of a contact hole of a semiconductor device. The first opening 16-1 of the standard test device corresponds to the defective contact hole having the bottom on which the residual film resides. The second opening 16-2 of the standard test device corresponds to the contact hole true of any residual film of the semiconductor device. The dummy film 12 has an accurately controlled thickness.

The supporting substrate 10 of the standard test device is preferably made of the same material as the supporting substrate of the semiconductor device. In this embodiment, the supporting substrate 10 is made of a single crystal silicon. Notwithstanding, polysilicon, glass and quartz and sapphire may be used for the supporting substrate 10.

The dummy film 12 of the standard test device is preferable made of the same material as the residual film on the bottom of the contact hole of the semiconductor device. In this embodiment, the dummy film 12 is made of silicon oxide.

The resin layer 14 has a thickness which corresponds to the depth of the contact hole of the semiconductor device. The thickness of the resin layer 14 may be, for example, in the range of a few micrometers to 1000 micrometers. Plane size of the first and second openings 16-1 and 16-2 is preferably the same as the contact hole. The aspect ratio of the first and second openings 16-1 and 16-2 is also preferably the same as the contact hole. The diameter of the opening 16 may be in the range of 0.1 micrometer to 0.5 micrometers.

The above standard test device is used for both standards of the perfect contact hole free of any residual film and the imperfect or defective contact hole having the bottom on which the residual film resides. The above standard test device is capable of concurrently testing both the perfect contact hole free of any residual film and the imperfect or defective contact hole having the bottom on which the residual film resides.

The semiconductor devices are mass-produced. Some of the contact holes are perfectly etched so that no residual films reside on the bottoms of the contact holes. The other contact holes are imperfectly etched so that the residual films reside on the bottoms of the contact holes. The above standard test device is responsible for both the perfect and imperfect contact holes in the semiconductor device.

The above standard test device further provides the same effects as in the first embodiment.

Figure 4:
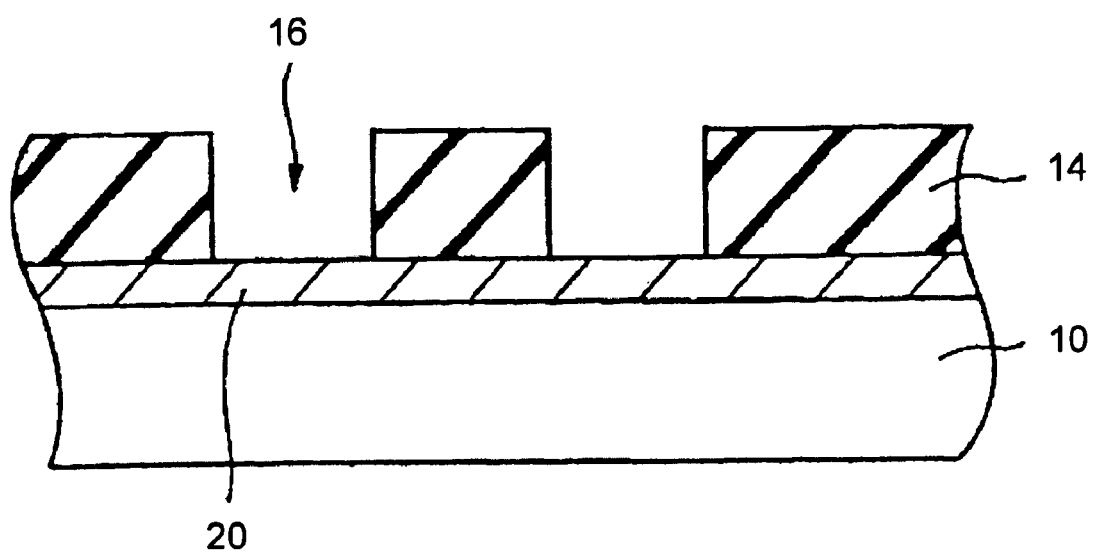
FIG. 4 is a fragmentary cross sectional elevation view illustrative of a novel standard test device of a third embodiment in accordance with the present invention.

Third Embodiment:

A third embodiment according to the present invention will be described in detail with reference to the drawings. The descriptions will focus on differences of this embodiment from the first embodiment to avoid redundancy descriptions. FIG. 4 is a fragmentary cross sectional elevation view illustrative of a novel standard test device of a third embodiment in accordance with the present invention. In the above first embodiment, the dummy film 12 is made of silicon oxide. In this embodiment, however, the dummy film 20 is made of silicon nitride.

The novel standard test device has a supporting substrate 10. A silicon nitride dummy film 20 is provided on a top surface of the supporting substrate 10. A photo-sensitive resin layer 14 having openings 16 are provided on the silicon nitride dummy film 20. Bottoms 18 of the openings 16 comprise parts of the top surface of the silicon nitride dummy film 20. The silicon nitride dummy film 20 of the standard test device corresponds to a residual film of a contact hole of a semiconductor device. The openings 16 of the standard test device correspond to the contact holes of the semiconductor device. The silicon nitride dummy film 20 has an accurately controlled thickness.

The silicon nitride film is stronger than the silicon oxide film. The silicon nitride film is also lower in hygroscopicity than the silicon oxide film. The silicon nitride film is also superior in durability than the silicon oxide film because no film growth appears by oxygen in atmosphere.

As a modification to this embodiment, the dummy film may be made of ONO for improvement in durability.

The silicon nitride film has a larger dielectric constant than the silicon oxide film, for which reason a thinner dummy film of silicon nitride is equivalent in dielectric constant to a thicker dummy film of silicon oxide. This means that the use of silicon nitride for the dummy film makes it possible to form the standard test device which provides the reference standard for equivalently thicker residual films than when the silicon oxide dummy film is used.

Figure 5:
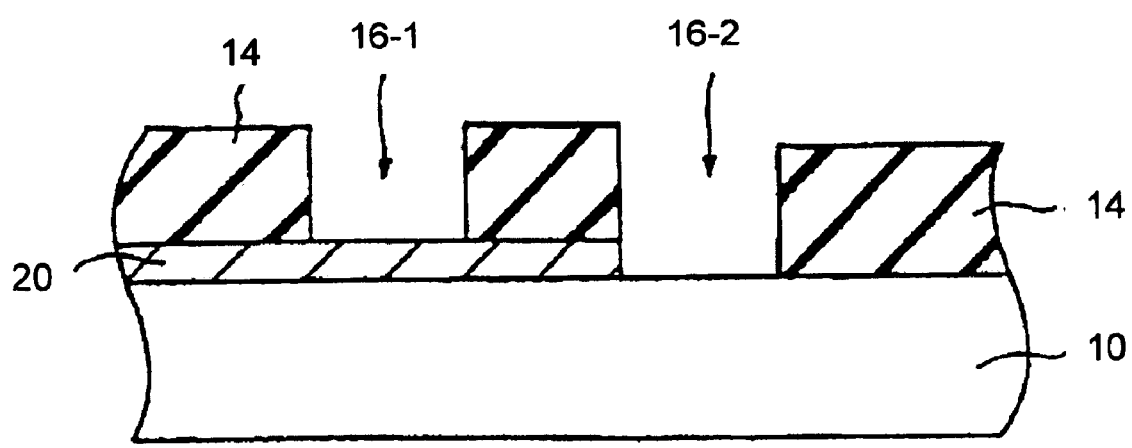
FIG. 5 is a fragmentary cross sectional elevation view illustrative of a novel standard test device of a fourth embodiment in accordance with the present invention.

Fourth Embodiment:

A fourth embodiment according to the present invention will be described in detail with reference to the drawings. The descriptions will focus on differences of this embodiment from the second embodiment to avoid redundancy descriptions. FIG. 5 is a fragmentary cross sectional elevation view illustrative of a novel standard test device of a fourth embodiment in accordance with the present invention. In the above second embodiment, the dummy film 12 is made of silicon oxide. In this embodiment, however, the dummy film 20 is made of silicon nitride.

The novel standard test device has a supporting substrate 10. A silicon nitride dummy film 20 is provided on a selected region of a top surface of the supporting substrate 10. A photo-sensitive resin layer 14 having first and second openings 16-1 and 16-2 are provided on the dummy film 12 and on an unselected region of the top surface of the supporting substrate 10. A bottom of the first opening 16-1 comprises a part of the top surface of the silicon nitride dummy film 20. A bottom of the second opening 16-2 comprises a part of the unselected region of the top surface of the supporting substrate 10. The silicon nitride dummy film 20 of the standard test device corresponds to a residual film of a contact hole of a semiconductor device. The first opening 16-1 of the standard test device corresponds to the defective contact hole having the bottom on which the residual film resides. The second opening 16-1 of the standard test device corresponds to the contact hole free of any residual film of the semiconductor device. The silicon nitride dummy film 20 has an accurately controlled thickness.

The silicon nitride film is stronger than the silicon oxide film. The silicon nitride film is also lower in hygroscopicity than the silicon oxide film. The silicon nitride film is also superior in durability than the silicon oxide film because no film growth appears by oxygen in atmosphere.

As a modification to this embodiment, the dummy film may be made of ONO for improvement in durability.

The silicon nitride film has a larger dielectric constant than the silicon oxide film, for which reason a thinner dummy film of silicon nitride is equivalent in dielectric constant to a thicker dummy film of silicon oxide. This means that the use of silicon nitride for the dummy film makes it possible to form the standard test device which provides the reference standard for equivalently thicker residual films than when the silicon oxide dummy film is used.

Further, the above standard test device is used for both standards of the perfect contact hole free of any residual film and the imperfect or defective contact hole having the bottom on which the residual film resides. The above standard test device is capable of concurrently testing both the perfect contact hole free of any residual film and the imperfect or defective contact hole having the bottom on which the residual film resides.

The semiconductor devices are mass-produced. Some of the contact holes are perfectly etched so that no residual films reside on the bottoms of the contact holes. The other contact holes are imperfectly etched so that the residual films reside on the bottoms of the contact holes. The above standard test device is responsible for both the perfect and imperfect contact holes in the semiconductor device.

The above standard test device further provides the same effects as in the first embodiment.

Figure 6:
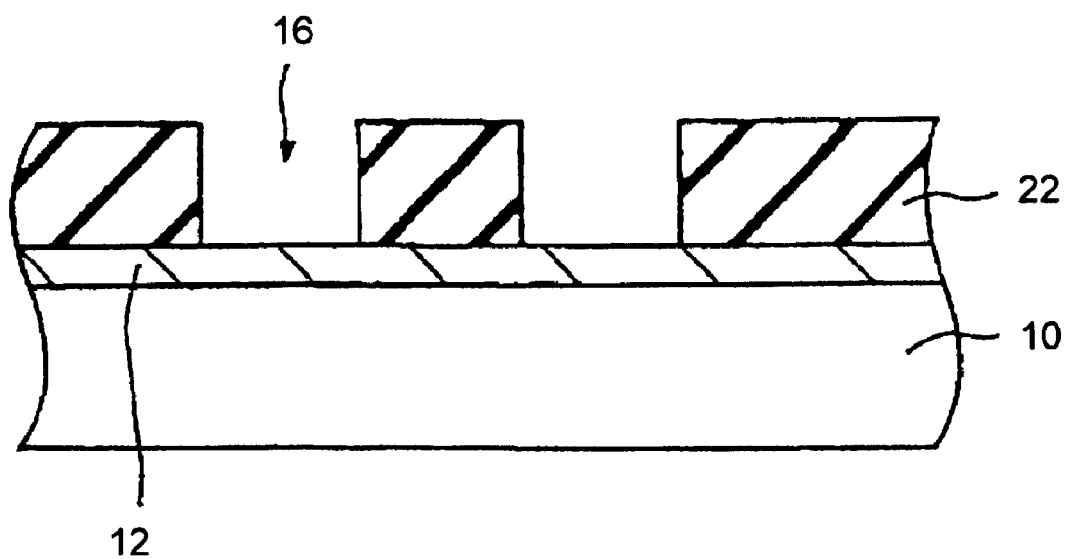
FIG. 6 is a fragmentary cross sectional elevation view illustrative of a novel standard test device of a fifth embodiment in accordance with the present invention.

Fifth Embodiment:

A fifth embodiment according to the present invention will be described in detail with reference to the drawings. The descriptions will focus on differences of this embodiment from the first embodiment to avoid redundancy descriptions. FIG. 6 is a fragmentary cross sectional elevation view illustrative of a novel standard test device of a fifth embodiment in accordance with the present invention. In this embodiment, the resin film 22 has the same dielectric constant as the film in which the contact hole is formed, and the material of the residual film on the bottom of the contact hole is the same as this film. Thus, the resin film 22 has the same dielectric constant as the residual film on the bottom of the contact hole.

The novel standard test device has a supporting substrate 10. A silicon nitride dummy film 20 is provided on a top surface of the supporting substrate 10. A photo-sensitive resin layer 22 having openings 16 are provided on the silicon nitride dummy film 20. The photo-sensitive resin layer 22 has the same dielectric constant as the residual film on the bottom of the contact hole. Bottoms 18 of the openings 16 comprise parts of the top surface of the silicon nitride dummy film 20. The silicon nitride dummy film 20 of the standard test device corresponds to a residual film of a contact hole of a semiconductor device. The openings 16 of the standard test device correspond to the contact holes of the semiconductor device. The silicon nitride dummy film 20 has an accurately controlled thickness.

The photo-sensitive resin has a dielectric constant in the range of 4–5. The contact holes are usually formed in the silicon oxide film or the silicon nitride film. The silicon oxide film and the silicon nitride film have lower dielectric constants than that of the photo-sensitive resin. The dielectric constant of the resin layer 22 is adjusted to be equal to the film in which the contact hole is formed. In order to drop the dielectric constant, it is effective to introduce fluorine containing resin or to have the photo-sensitive resin contain side chain of fluorine. It is also effective to introduce materials having lower dielectric constants such as acrylic resins and silicone resins.

It is preferable that denaturation to the resin layer is carried out to drop the dielectric constant provided that the resin layer has a photo-sensitivity.

If such a strong denaturation to the resin layer as removing the photo-sensitivity from the resin layer is necessary, then it is possible to form the openings as follows.

A secondary photo-sensitive resin film not illustrated is formed on the resin layer 22, and then the secondary photo-sensitive resin film is patterned to form a mask. The resin layer 22 is selectively etched by use of the mask thereby forming the openings. The mask is then removed.

The silicon oxide or silicon nitride residual film and the resin film are different from each other in chemical reactivity to the developer, for which reason it is easy to carry out the patterning to the resin layer.

Other method of dropping the dielectric constant of the resin layer is to form micro-spaces in the photo-sensitive resin, whereby an apparent dielectric constant of the resin layer is dropped.

The electric property of the resin layer is made closer to the electric property of the film in which the contact hole is formed. The contrast of the secondary electron image of the opening of the standard test device is made closer to the contrast of the contact hole, whereby it is possible to accurately evaluate or measure the thickness of the residual film on the bottom of the contact hole.

It is of course possible to increase the dielectric constant of the resin layer to adjust the same to the dielectric constant of the film in which the contact hole is formed.

The other electric properties effective to the contrast of the secondary electron image are secondary electron emission ratio and thermal expansion coefficient. Those factors are also preferable made closer to each other between the resin layer and the film in which the contact hole is formed.

Figure 7:
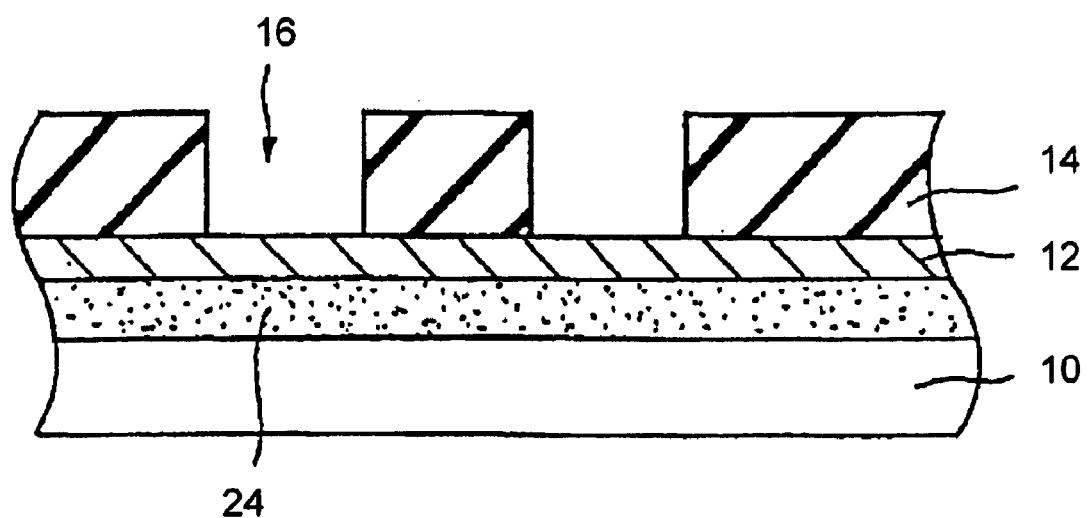
FIG. 7 is a fragmentary cross sectional elevation view illustrative of a novel standard test device of a sixth embodiment in accordance with the present invention.

Sixth Embodiment:

A sixth embodiment according to the present invention will be described in detail with reference to the drawings. The descriptions will focus on differences of this embodiment from the first embodiment to avoid redundancy descriptions. FIG. 7 is a fragmentary cross sectional elevation view illustrative of a novel standard test device of a sixth embodiment in accordance with the present invention. In the above first embodiment, the dummy film 12 is provided on the top surface of the supporting substrate 10. In this embodiment, however, the dummy film 12 is provided on a diffusion layer 24 formed over the supporting substrate 10.

The novel standard test device has a supporting substrate 10. A diffusion layer 24 is formed on the supporting substrate 10. A silicon oxide dummy film 12 is provided on a top surface of the diffusion layer 24. A photo-sensitive resin layer 14 having openings 16 are provided on the silicon oxide dummy film 12. Bottoms 18 of the openings 16 comprise parts of the top surface of the silicon oxide dummy film 12. The silicon oxide dummy film 12 of the standard test device corresponds to a residual film of a contact hole of a semiconductor device. The openings 16 of the standard test device correspond to the contact holes of the semiconductor device. The silicon oxide dummy film 12 has an accurately controlled thickness. The diffusion layer 24 has an impurity such as B, P or As. The diffusion layer 24 has a thickness in the range of a few nanometers to a few micrometers. The thickness and the impurity concentration of the diffusion layer 24 of the standard test device are adjusted to those of the actual diffusion layer of the semiconductor device. This standard test device is applicable to the semiconductor device having the diffusion layer. The contrast of the secondary electron image of the opening of the standard test device is made closer to the contrast of the secondary electron image of the contact hole, whereby it is possible to accurately evaluate or measure the thickness of the residual film on the bottom of the contact hole.

Figure 8:
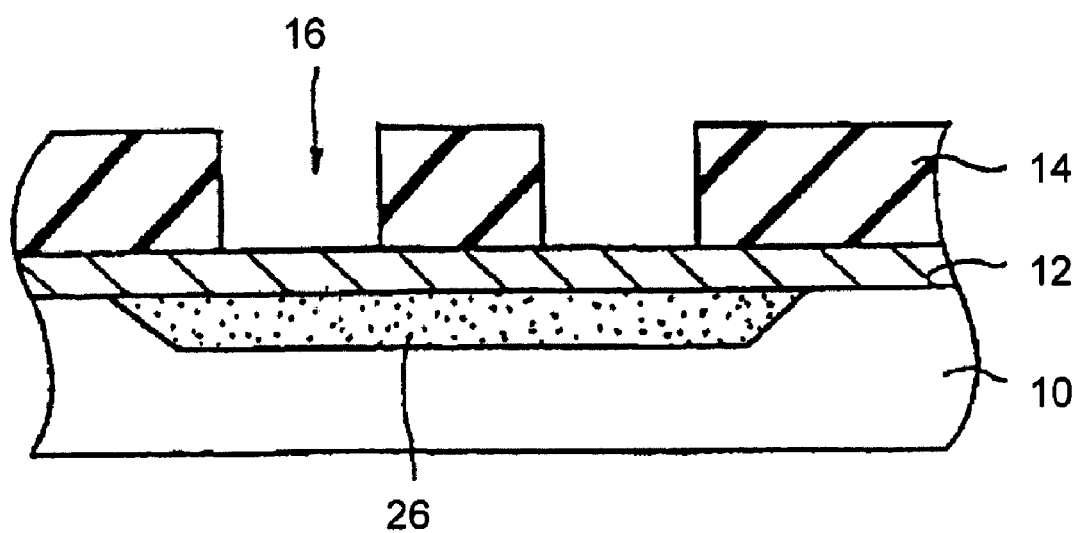
FIG. 8 is a fragmentary cross sectional elevation view illustrative of a novel standard test device of a seventh embodiment in accordance with the present invention.

Seventh Embodiment:

A seventh embodiment according to the present invention will be described in detail with reference to the drawings. The descriptions will focus on differences of this embodiment from the first embodiment to avoid redundancy descriptions. FIG. 8 is a fragmentary cross sectional elevation view illustrative of a novel standard test device of a seventh embodiment in accordance with the present invention. In the above first embodiment, the dummy film 12 is provided on the top surface of the supporting substrate 10. In this embodiment, however, the dummy film 12 is provided on a well region 26 formed over the supporting substrate 10.

The novel standard test device has a supporting substrate 10. A well region 26 is formed on the supporting substrate 10. A silicon oxide dummy film 12 is provided on a top surface of the well region 26. A photo-sensitive resin layer 14 having openings 16 are provided on the silicon oxide dummy film 12. Bottoms 18 of the openings 16 comprise parts of the top surface of the silicon oxide dummy film 12. The silicon oxide dummy film 12 of the standard test device corresponds to a residual film of a contact hole of a semiconductor device. The openings 16 of the standard test device correspond to the contact holes of the semiconductor device. The silicon oxide dummy film 12 has an accurately controlled thickness. The well region 26 has an impurity such as B, P or As. The well region 26 has a depth in the range of a few nanometers to a few micrometers. The thickness and the impurity concentration of the well region 26 of the standard test device are adjusted to those of the actual diffusion layer of the semiconductor device. This standard test device is applicable to the semiconductor device having the well region. The contrast of the secondary electron image of the opening of the standard test device is made closer to the contrast of the secondary electron image of the contact hole, whereby it is possible to accurately evaluate or measure the thickness of the residual film on the bottom of the contact hole.

Figure 9:
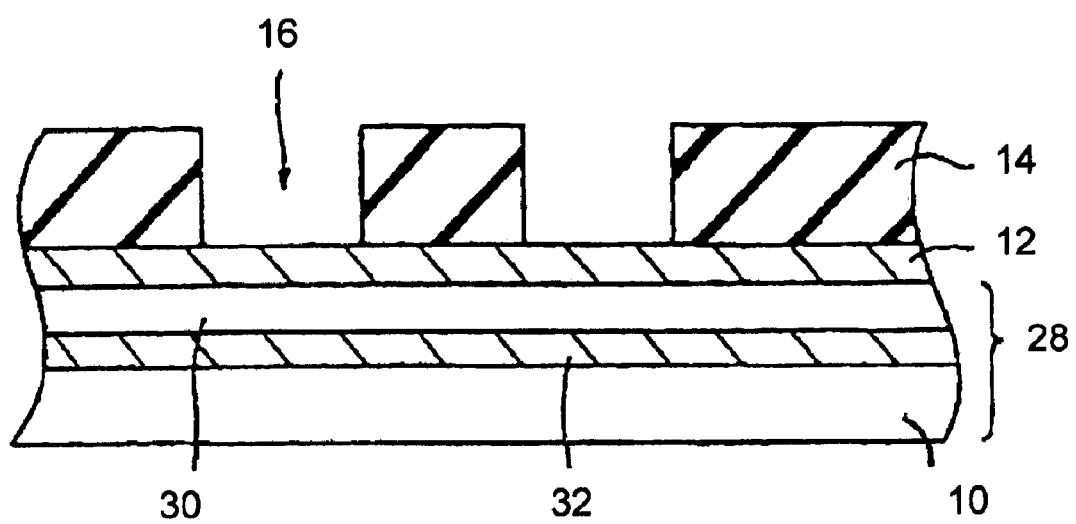
FIG. 9 is a fragmentary cross sectional elevation view illustrative of a novel standard test device of an eighth embodiment in accordance with the present invention.

Eighth Embodiment:

An eighth embodiment according to the present invention will be described in detail with reference to the drawings. The descriptions will focus on differences of this embodiment from the first embodiment to avoid redundancy descriptions. FIG. 9 is a fragmentary cross sectional elevation view illustrative of a novel standard test device of an eighth embodiment in accordance with the present invention. In the above first embodiment, the dummy film 12 is provided on the top surface of the supporting substrate 10. In this embodiment, however, the dummy film 12 is provided on a silicon-on-insulator substrate 28.

The novel standard test device has a silicon-on-insulator substrate 28. The silicon-on-insulator substrate 28 comprises a supporting substrate 10, an insulation film 32 provided on the top surface of the supporting substrate 10, and an active layer 30 of single crystal silicon provided on the insulation layer 32. A silicon oxide dummy film 12 is provided on a top surface of the active layer 30 of the silicon-on-insulator substrate 28. A photo-sensitive resin layer 14 having openings 16 are provided on the silicon oxide dummy film 12. Bottoms 18 of the openings 16 comprise parts of the top surface of the silicon oxide dummy film 12. The silicon oxide dummy film 12 of the standard test device corresponds to a residual film of a contact hole of a semiconductor device. The openings 16 of the standard test device correspond to the contact holes of the semiconductor device. The silicon oxide dummy film 12 has an accurately controlled thickness. The active region 30 has an impurity such as B, P or As. The active region 30 has a thickness in the range of a few nanometers to a few micrometers. The thickness and the impurity concentration of the active region 30 of the standard test device are adjusted to those of the actual diffusion layer of the semiconductor device. The thickness of the insulation film 32 is adjusted to that of the actual insulation film of the silicon-on-insulator substrate. The conductivity type of the supporting substrate may be either p-type or n-type. The impurity concentration of the supporting substrate 10 of the silicon-on-insulator substrate 10 of the standard test device is, for example, in the range of 1E14–1E15 atoms/cm3. The silicon-on-insulator substrate 28 of the standard test device is preferable made closer to the actual silicon-on-insulator substrate. The contrast of the secondary electron image of the opening of the standard test device is made closer to the contrast of the secondary electron image of the contact hole, whereby it is possible to accurately evaluate or measure the thickness of the residual film on the bottom of the contact hole.

Figure 10:
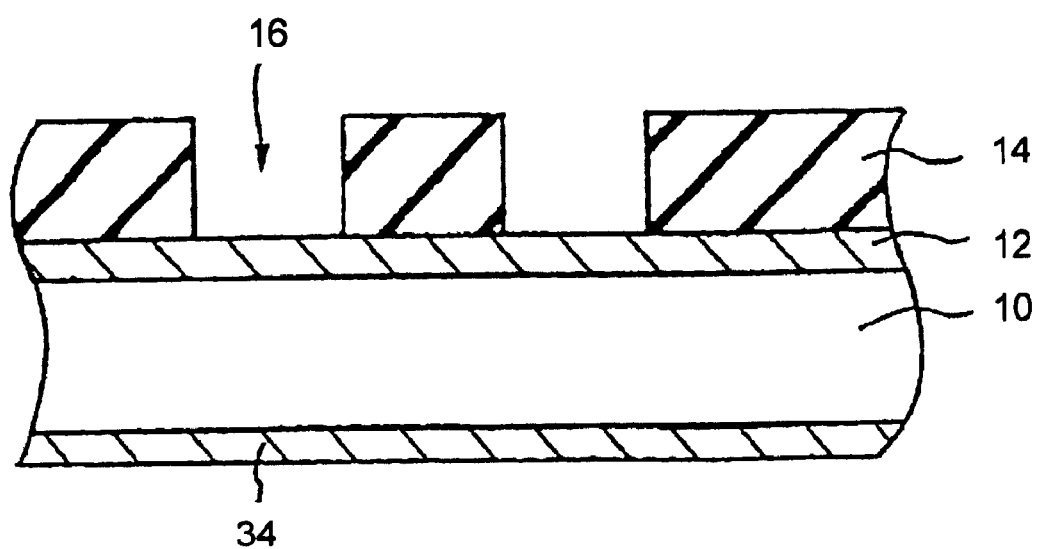
FIG. 10 is a fragmentary cross sectional elevation view illustrative of a novel standard test device of a ninth embodiment in accordance with the present invention.

Ninth Embodiment:

A ninth embodiment according to the present invention will be described in detail with reference to the drawings. The descriptions will focus on differences of this embodiment from the first embodiment to avoid redundancy descriptions. FIG. 10 is a fragmentary cross sectional elevation view illustrative of a novel standard test device of a ninth embodiment in accordance with the present invention. In the above first embodiment, the dummy film 12 is provided on the top surface of the supporting substrate 10. In this embodiment, however, the dummy film 12 is provided on the supporting substrate 10 having a bottom on which a bottom insulation layer 34 is formed.

The novel standard test device has a supporting substrate 10 having a bottom on which a bottom insulation layer 34 is formed. A silicon oxide dummy film 12 is provided on a top surface of the supporting substrate 10. A photo-sensitive resin layer 14 having openings 16 are provided on the silicon oxide dummy film 12. Bottoms 18 of the openings 16 comprise parts of the top surface of the silicon oxide dummy film 12. The silicon oxide dummy film 12 of the standard test device corresponds to a residual film of a contact hole of a semiconductor device. The openings 16 of the standard test device correspond to the contact holes of the semiconductor device. The silicon oxide dummy film 12 has an accurately controlled thickness. The electron beam is irradiated onto the openings 16 to cause secondary electron current and beam pass current which penetrates through the dummy film 12 and reaches the supporting substrate 10. However, the beam pass current could not penetrate through the bottom of the supporting substrate 10 due to the presence of the bottom insulating film 34. If the actual semiconductor device substrate has the bottom insulating layer, then this standard test device is applicable thereto. The contrast of the secondary electron image of the opening of the standard test device is made closer to the contrast of the secondary electron image of the contact hole, whereby it is possible to accurately evaluate or measure the thickness of the residual film on the bottom of the contact hole.

Figure 11A:
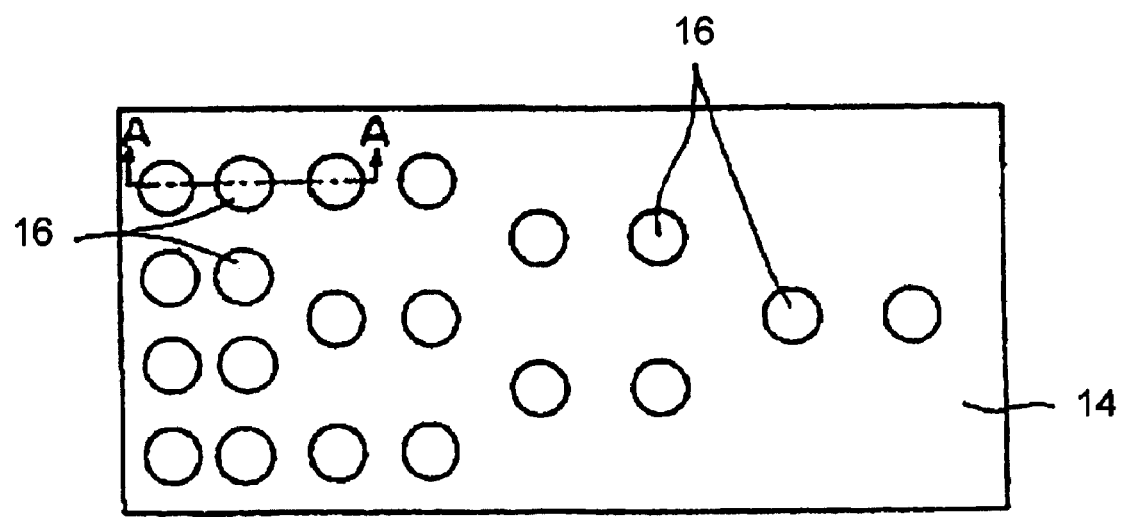
FIG. 11A is a fragmentary plane view illustrative of a novel standard test device of a tenth embodiment in accordance with the present invention.
Figure 11B:
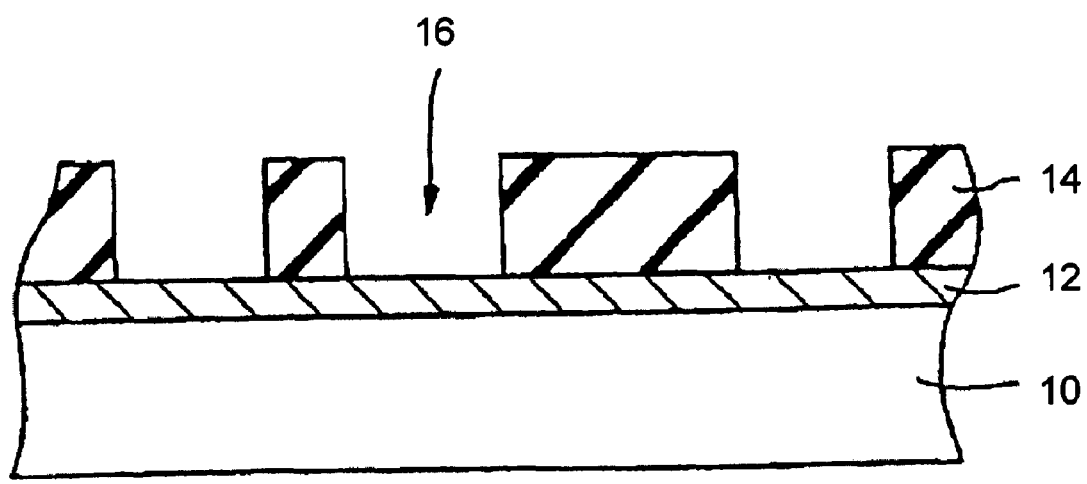
FIG. 11B is a fragmentary cross sectional elevation view illustrative of a novel standard test device of a tenth embodiment in accordance with the present invention taken along an A—A line of FIG. 11A.

Tenth Embodiment:

A tenth embodiment according to the present invention will be described in detail with reference to the drawings. The descriptions will focus on differences of this embodiment from the first embodiment to avoid redundancy descriptions. FIG. 11A is a fragmentary plane view illustrative of a novel standard test device of a tenth embodiment in accordance with the present invention. FIG. 11B is a fragmentary cross sectional elevation view illustrative of a novel standard test device of a tenth embodiment in accordance with the present invention taken along an A—A line of FIG. 11A. In the above first embodiment, the openings 16 are formed in the resin layer 14 at a constant distribution density. In this embodiment, however, the openings 16 are formed in the resin layer 14 at variable distribution densities.

The novel standard test device has a supporting substrate 10. A silicon oxide dummy film 12 is provided on a top surface of the supporting substrate 10. A photo-sensitive resin layer 14 having openings 16 are provided on the silicon oxide dummy film 12. The openings 16 are formed in the resin layer 14 at variable distribution densities. The distribution density of the openings 16 varies over position. Bottoms 18 of the openings 16 comprise parts of the top surface of the silicon oxide dummy film 12. The silicon oxide dummy film 12 of the standard test device corresponds to a residual film of a contact hole of a semiconductor device. The openings 16 of the standard test device correspond to the contact holes of the semiconductor device. The silicon oxide dummy film 12 has an accurately controlled thickness. Usually, the actual semiconductor device substrate has variation in distribution density of the contact holes, for which reason the opening at the same or closest distribution density of this standard device is used and thus receives the electron beam irradiation. The contrast of the secondary electron image and the beam pass current depend on the distribution density of the contact holes. The contrast of the secondary electron image of the opening at the same or closest distribution density of the standard test device is made closer to the contrast of the secondary electron image of the contact hole, whereby it is possible to accurately evaluate or measure the thickness of the residual film on the bottom of the contact hole.

Figure 12:
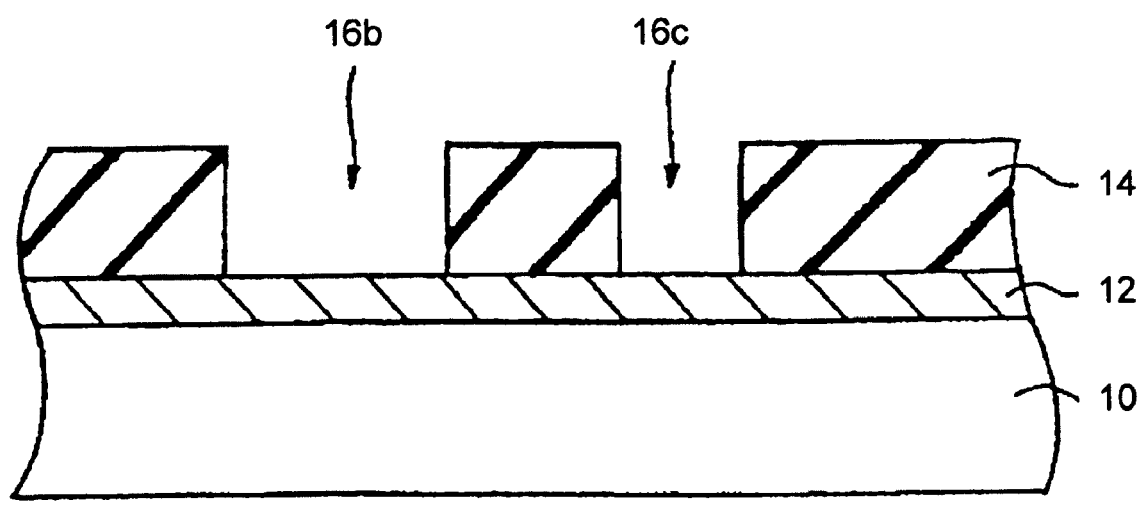
FIG. 12 is a fragmentary cross sectional elevation view illustrative of a novel standard test device of an eleventh embodiment in accordance with the present invention.

Eleventh Embodiment:

An eleventh embodiment according to the present invention will be described in detail with reference to the drawings. The descriptions will focus on differences of this embodiment from the first embodiment to avoid redundancy descriptions. FIG. 12 is a fragmentary cross sectional elevation view illustrative of a novel standard test device of an eleventh embodiment in accordance with the present invention. In the above first embodiment, the openings 16 formed in the resin layer 14 have a uniform aspect ratio. In this embodiment, however, the openings 16b and 16c formed in the resin layer 14 have different aspect ratios.

The novel standard test device has a supporting substrate 10. A silicon oxide dummy film 12 is provided on a top surface of the supporting substrate 10. A photo-sensitive resin layer 14 having first and second openings 16b and 16c are provided on the silicon oxide dummy film 12. The first and second openings 16b and 16c are formed to have different aspect ratios from each other. The first and second openings 16b and 16c have the same depth because the thickness of the resin layer 14 is uniform. However, the first and second openings 16b and 16c are different in plane size so that the first and second openings 16b and 16c are different in aspect ratio. The first opening 16b is larger in plane size than the second opening 16c so that the first opening 16b is higher in aspect ratio than the second opening 16c. The aspect ratio may be ranged from 2–20. Bottoms 18 of the first and second openings 16b and 16c comprise parts of the top surface of the silicon oxide dummy film 12. The silicon oxide dummy film 12 of the standard test device corresponds to a residual film of a contact hole of a semiconductor device. The first and second openings 16b and 16c of the standard test device correspond to the contact holes having the different aspect ratios of the semiconductor device. The silicon oxide dummy film 12 has an accurately controlled thickness. Usually, the actual semiconductor device has variation in aspect ratio of the contact holes, for which reason the opening having the same or closest aspect ratio of this standard device is used and thus receives the electron beam irradiation. The contrast of the secondary electron image and the beam pass current depend on the aspect ratio of the contact holes. The contrast of the secondary electron image of the opening having the same or closest aspect ratio of the standard test device is made closer to the contrast of the secondary electron image of the contact hole, whereby it is possible to accurately evaluate or measure the thickness of the residual film on the bottom of the contact hole.

Figure 13:
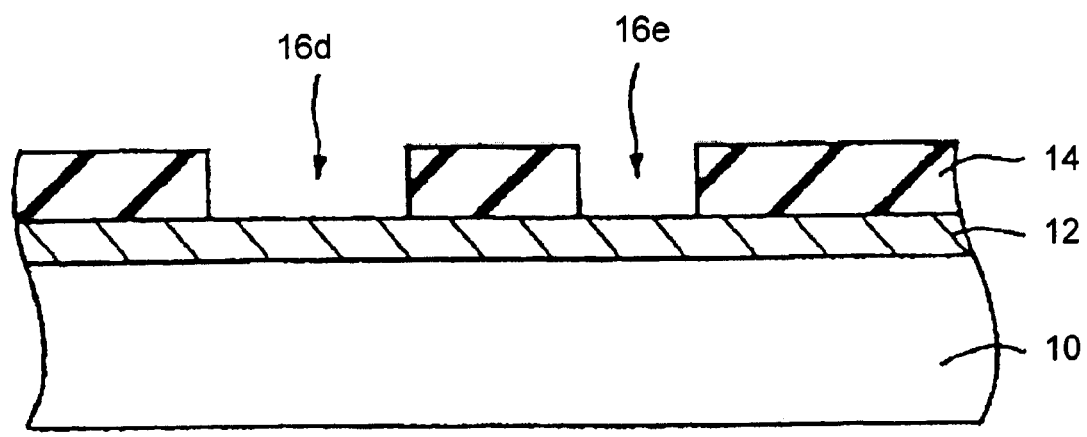
FIG. 13 is a fragmentary cross sectional elevation view illustrative of a novel standard test device of a twelfth embodiment in accordance with the present invention.

Twelfth Embodiment:

A twelfth embodiment according to the present invention will be described in detail with reference to the drawings. The descriptions will focus on differences of this embodiment from the first embodiment to avoid redundancy descriptions. FIG. 13 is a fragmentary cross sectional elevation view illustrative of a novel standard test device of a twelfth embodiment in accordance with the present invention. In the above first embodiment, the thickness of the resin layer 14 is uniform among the plural standard test devices and the depth and aspect ratio of the openings formed in the resin layer 14 are also uniform. In this embodiment, however, the thickness of the resin layer 14 is different among the plural standard test devices but each of the standard test devices has variations in plane size and aspect ratio of the openings 16d and 16e formed in the resin layer 14.

The novel standard test device has a supporting substrate 10. A silicon oxide dummy film 12 is provided on a top surface of the supporting substrate 10. A photo-sensitive resin layer 14 having first and second openings 16d and 16e are provided on the silicon oxide dummy film 12. The first and second openings 16d and 16e are formed to have different aspect ratios from each other. The first and second openings 16d and 16e have the same depth because the thickness of the resin layer 14 is uniform. However, the first and second openings 16d and 16e are different in plane size so that the first and second openings 16d and 16e are different in aspect ratio. The first opening 16d is larger in plane size than the second opening 16e so that the first opening 16d is higher in aspect ratio than the second opening 16e. The aspect ratio may be ranged from 2–20. Further, the thickness of the resin layer 14 is different among the plural standard test device. The depth of the first opening 16d is different between the plural standard test device. The aspect ratio of the first opening 16d is different between the plural standard test device. The depth of the second opening 16e is also different between the plural standard test device. The aspect ratio of the second opening 16e is different between the plural standard test device. Bottoms 18 of the first and second openings 16d and 16e comprise parts of the top surface of the silicon oxide dummy film 12. The silicon oxide dummy film 12 of the standard test device corresponds to a residual film of a contact hole of a semiconductor device. The first and second openings 16d and 16e of the standard test device correspond to the contact holes having the different aspect ratios of the semiconductor device. The silicon oxide dummy film 12 has an accurately controlled thickness. Usually, the actual semiconductor device has variation in aspect ratio of the contact holes, for which reason the opening having the same or closest aspect ratio of this standard device is used and thus receives the electron beam irradiation. The contrast of the secondary electron image and the beam pass current depend on the aspect ratio of the contact holes. The contrast of the secondary electron image of the opening having the same or closest aspect ratio of the standard test device is made closer to the contrast of the secondary electron image of the contact hole, whereby it is possible to accurately evaluate or measure the thickness of the residual film on the bottom of the contact hole.

Figure 14:
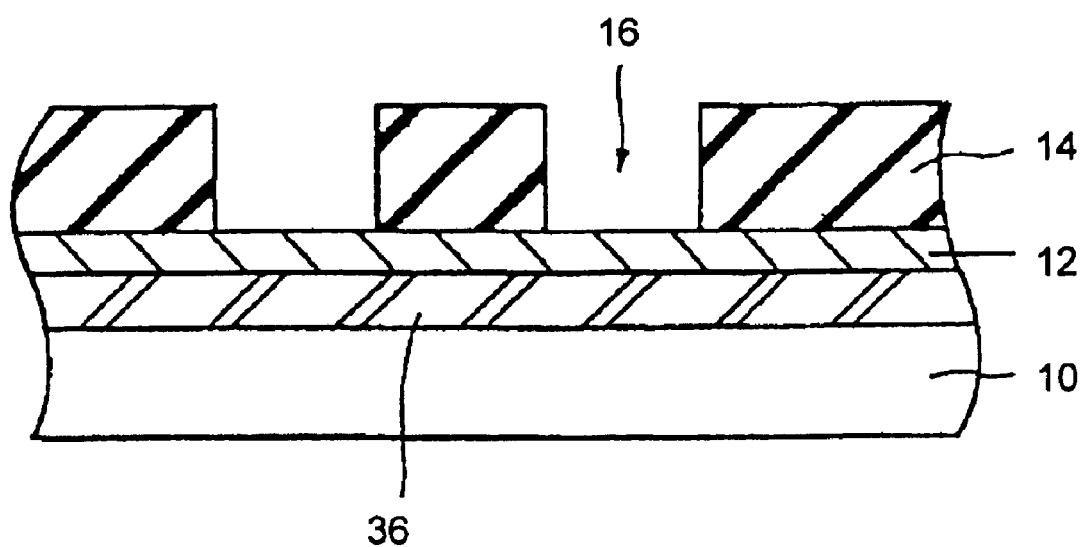
FIG. 14 is a fragmentary cross sectional elevation view illustrative of a novel standard test device of a thirteenth embodiment in accordance with the present invention.

Thirteenth Embodiment:

A thirteenth embodiment according to the present invention will be described in detail with reference to the drawings. The descriptions will focus on differences of this embodiment from the first embodiment to avoid redundancy descriptions. FIG. 14 is a fragmentary cross sectional elevation view illustrative of a novel standard test device of a thirteenth embodiment in accordance with the present invention. In the above first embodiment, the dummy film 12 is provided on the top surface of the supporting substrate 10. In this embodiment, however, the dummy film 12 is provided on a metal layer 36 formed over the supporting substrate 10.

The novel standard test device has a supporting substrate 10. A metal layer 36 is formed on the supporting substrate 10. A silicon oxide dummy film 12 is provided on a top surface of the metal layer 36. A photo-sensitive resin layer 14 having openings 16 are provided on the silicon oxide dummy film 12. Bottoms 18 of the openings 16 comprise parts of the top surface of the silicon oxide dummy film 12. The silicon oxide dummy film 12 of the standard test device corresponds to a residual film of a contact hole of a semiconductor device. The openings 16 of the standard test device correspond to the contact holes of the semiconductor device. The silicon oxide dummy film 12 has an accurately controlled thickness. The metal layer 36 has a thickness in the range of a few hundreds angstroms to a few micrometers. The thickness and the material of the metal layer 36 of the standard test device are adjusted to those of the metal layer such as the interconnection layer of the semiconductor device. This standard test device is applicable to the semiconductor device having the interconnection layer. For the metal layer 36, there are available Al, Cu, W, Mo, Co, Au, Pt, Ti and silicide or salicide such as P—Si. In place of the metal film 36, any other conductive film may be provided such as a silicon film or a polysilicon film. The contrast of the secondary electron image of the opening of the standard test device is made closer to the contrast of the secondary electron image of the contact hole, whereby it is possible to accurately evaluate or measure the thickness of the residual film on the bottom of the contact hole.

Figure 15:
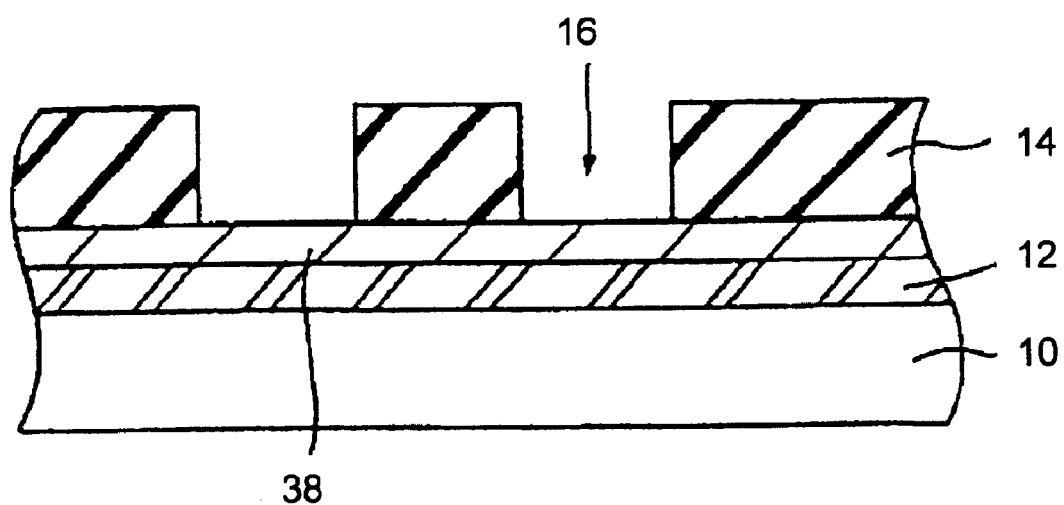
FIG. 15 is a fragmentary cross sectional elevation view illustrative of a novel standard test device of a fourteenth embodiment in accordance with the present invention.

Fourteenth Embodiment:

A fourteenth embodiment according to the present invention will be described in detail with reference to the drawings. The descriptions will focus on differences of this embodiment from the thirteenth embodiment to avoid redundancy descriptions. FIG. 15 is a fragmentary cross sectional elevation view illustrative of a novel standard test device of a fourteenth embodiment in accordance with the present invention. In the above thirteenth embodiment, the dummy film 12 is made of silicon oxide. In this embodiment, however, the dummy film 38 is made of titanium nitride.

The novel standard test device has a supporting substrate 10. A metal layer 36 is formed on the supporting substrate 10. A titanium nitride dummy film 38 is provided on a top surface of the metal layer 36. A photo-sensitive resin layer 14 having openings 16 are provided on the titanium nitride dummy film 38. Bottoms 18 of the openings 16 comprise parts of the top surface of the titanium nitride dummy film 38. The titanium nitride dummy film 38 of the standard test device corresponds to a residual film of a contact hole of a semiconductor device. The openings 16 of the standard test device correspond to the contact holes of the semiconductor device. The titanium nitride dummy film 38 has an accurately controlled thickness in the range of few hundreds angstroms to few thousands angstroms. The metal layer 36 has a thickness in the range of a few hundreds angstroms to a few micrometers. The thickness and the material of the metal layer 36 of the standard test device are adjusted to those of the metal layer such as the interconnection layer of the semiconductor device. The titanium nitride dummy film 38 corresponds to a titanium nitride film for preventing discussion and for improvement in adhesion and also for preventing halation of lithograph. This standard test device is applicable to the semiconductor device having the titanium nitride film. In place of titanium nitride, SiON is also available for the dummy film. The contrast of the secondary electron image of the opening of the standard test device is made closer to the contrast of the secondary electron image of the contact hole, whereby it is possible to accurately evaluate or measure the thickness of the residual film on the bottom of the contact hole.

Figure 16:
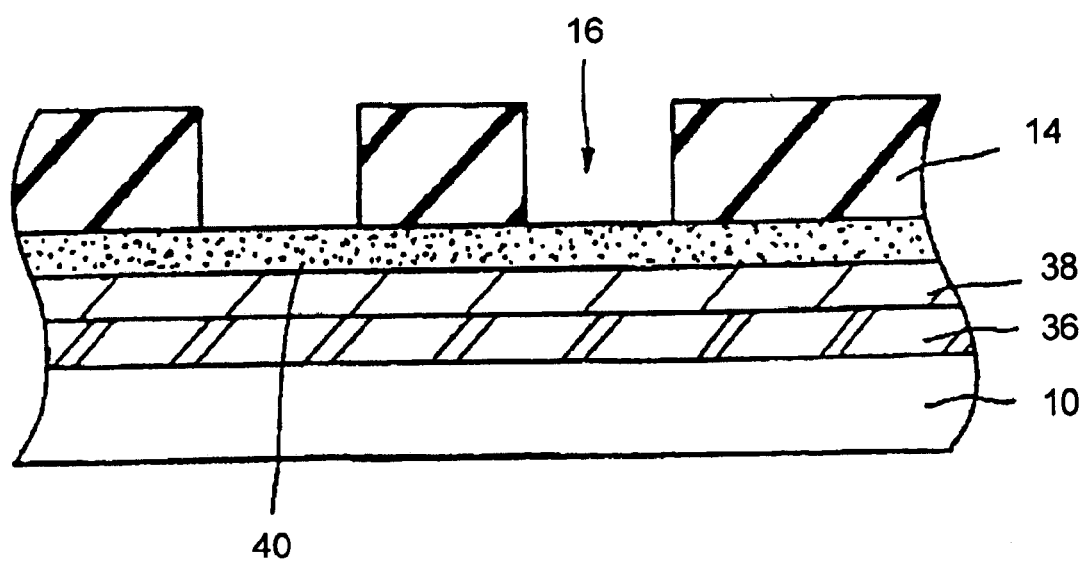
FIG. 16 is a fragmentary cross sectional elevation view illustrative of a novel standard test device of a fifteenth embodiment in accordance with the present invention.

Fifteenth Embodiment:

A fifteenth embodiment according to the present invention will be described in detail with reference to the drawings. The descriptions will focus on differences of this embodiment from the fourteenth embodiment to avoid redundancy descriptions. FIG. 16 is a fragmentary cross sectional elevation view illustrative of a novel standard test device of a fifteenth embodiment in accordance with the present invention. In the above fourteenth embodiment, the resin film 14 is provided on the titanium nitride dummy film 38. In this embodiment, however, the resin film 14 is provided on a fluoro-carbon film 40 provided on the titanium nitride dummy film 38.

The novel standard test device has a supporting substrate 10. A metal layer 36 is formed on the supporting substrate 10. A titanium nitride dummy film 38 is provided on a top surface of the metal layer 36. A fluoro-carbon film 40 is provided on the titanium nitride dummy film 38. A photo-sensitive resin layer 14 having openings 16 are provided on the fluoro-carbon film 40. Bottoms 18 of the openings 16 comprise parts of the top surface of the fluoro-carbon film 40. The titanium nitride dummy film 38 of the standard test device corresponds to a residual film of a contact hole of a semiconductor device. The openings 16 of the standard test device correspond to the contact holes of the semiconductor device. The fluoro-carbon film 40 corresponds to a deposited fluoro-carbon polymer film by a reactive ion etching carried out to have formed the contact holes. If the reactive ion etching is carried out, a fluoro-carbon polymer film is deposited on side wall and bottom of the contact hole. The etching property depends upon the thickness of the fluoro-carbon polymer film, for which reason it is important to accurately measure the thickness of the fluoro-carbon polymer film. The titanium nitride dummy film 38 has an accurately controlled thickness in the range of few hundreds angstroms to few thousands angstroms. The metal layer 36 has a thickness in the range of a few hundreds angstroms to a few micrometers. The thickness and the material of the metal layer 36 of the standard test device are adjusted to those of the metal layer such as the interconnection layer of the semiconductor device. The titanium nitride dummy film 38 corresponds to a titanium nitride film for preventing discussion and for improvement in adhesion and also for preventing halation of lithograph. This standard test device is applicable to the semiconductor device having the fluoro-carbon polymer film deposited by the reactive ion-etching. The contrast of the secondary electron image of the opening of the standard test device is made closer to the contrast of the secondary electron image of the contact hole, whereby it is possible to accurately evaluate or measure the thickness of the fluoro-carbon polymer film on the bottom of the contact hole.

It is possible that the dummy film comprises one insulating material of selected from the group consisting of SiO2, SiN, TiN, TaN, ONO, SiON, spin-on-glass (SOG), silica based inorganic substances, silica based organic substances, and ferromagnetic substances.

It is possible that the dummy film comprises one material of selected from the group consisting of Ti, W, Mo, Al, Au, Pt, Co, Ir, metal oxides, silicides, oxides of the silicides, intermetallic compounds, organic materials, oxide superconductance materials.

In the foregoing embodiments, the silicon oxide dummy film is formed by a thermal oxidation method. However, it is possible to use an anneal such as a lamp anneal to form the silicon oxide dummy film.

In the foregoing embodiments, the secondary electron current is detected to compare the contrast of the secondary electron image. In place of the contrast of the secondary electron image, it is possible to compare the beam pass current.

The materials and structures of the standard test devices may be modified from the above described materials so that the standard test device may be responsible to any various structures of the semiconductor devices. The standard test device preferably has the same structure as the semiconductor device to be tested.

Figure 17:
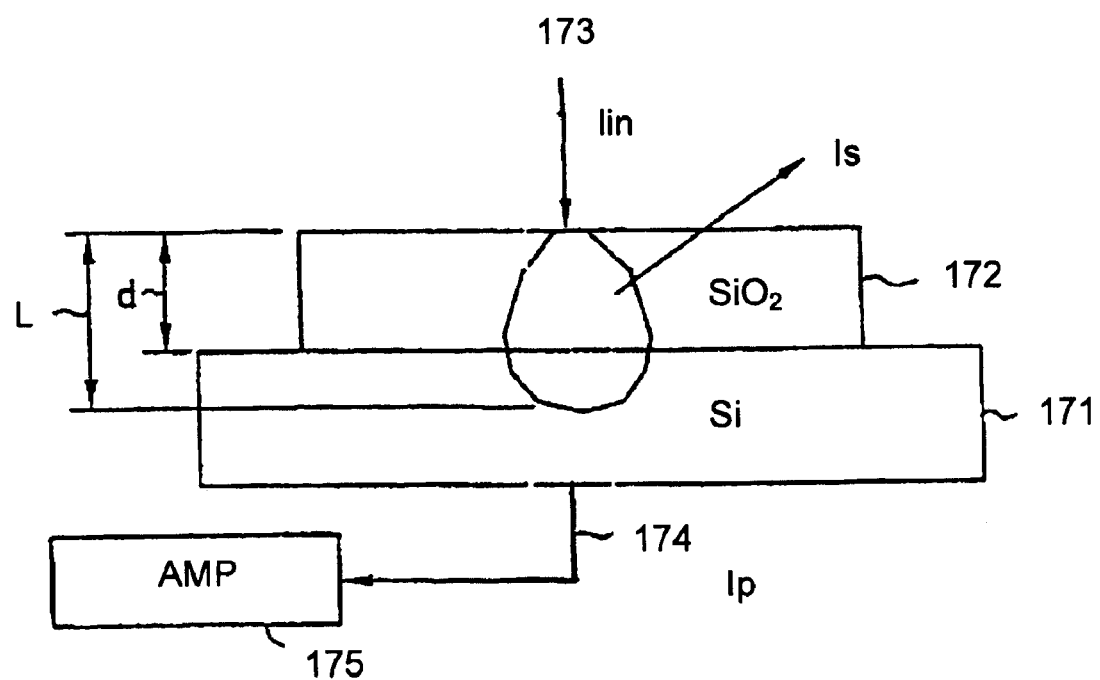
FIG. 17 is a diagram illustrative of a phenomenon of a beam pass current passing through a silicon oxide film to a silicon substrate in a novel method of measuring a beam pass current to evaluate a thickness of a residual silicon oxide film on a surface of the silicon substrate in a sixteenth embodiment in accordance with the present invention.

Sixteenth Embodiment:

A sixteenth embodiment according to the present invention will be described in detail with reference to the drawings. FIG. 17 is a diagram illustrative of a phenomenon of a beam pass current passing through a silicon oxide film to a silicon substrate in a novel method of measuring a beam pass current to evaluate a thickness of a residual silicon oxide film on a surface of the silicon substrate in a sixteenth embodiment in accordance with the present invention.

In this embodiment, the beam pass current which has passed through a silicon oxide film to a silicon substrate is measured to evaluate a thickness of a residual silicon oxide film on a surface of the silicon substrate, without measuring the secondary electron current.

If the secondary electron current is measured, it is necessary to capture secondary electrons emitted radially from a beam spot of the electron beam. The amount of electrons which passed through the silicon oxide film and reached the substrate may be given by the function of the electron beam quantity and the secondary electrons emitted from the beam spot. The perfect capturing of the secondary electrons depends upon the shape of the surface of the tested article. In contrast, the measurement of the beam pass current does not depend upon the shape of the surface of the tested article.

With reference to FIG. 17, a silicon oxide film 172 is formed on a silicon substrate 171. The silicon oxide film 172 has a thickness in the nanometer order. An electron beam 173 is irradiated onto the silicon oxide film 172. The quantity of the secondary electrons depends upon the tilting angle of the electron beam axis to the surface of the silicon oxide film. This tilting angle is kept over time period during which the electron beam irradiation is made. The electron beam 173 emitted from the electron gun to a vacuum space has an extremely high impedance. The amount of the electron beam depends on a filament voltage and an acceleration voltage but independent from an electric impedance of the tested article. The electron beam amount is measured by known available methods for every time when the control parameters of the electron guns are changed.

When the electron beam injection current is given by Iin, the secondary electron emission amount Is is given by the sum of the secondary electron Is(Si) emitted from the silicon film existing within the secondary electron escape depth and the secondary electron Is(SiO2) emitted from the silicon oxide film. If the silicon oxide film thickness is "d", then the beam pass current Ip is given by the following equation (1).

$$Ip = Iin - Is$$
$$= Iin - (Is(\text{Si}) + Is(\text{Sio2}))$$
$$= Iin\{1 - (1/L)[(L-d)\text{SEC}(\text{Si}) + d\text{SEC}(\text{SiO2})]\}$$

where L is the secondary electron escape depth, SEC(Si) is the secondary electron emission rate of silicon and dSEC (SiO2) is the secondary electron emission rate of silicon oxide.

Figure 18:
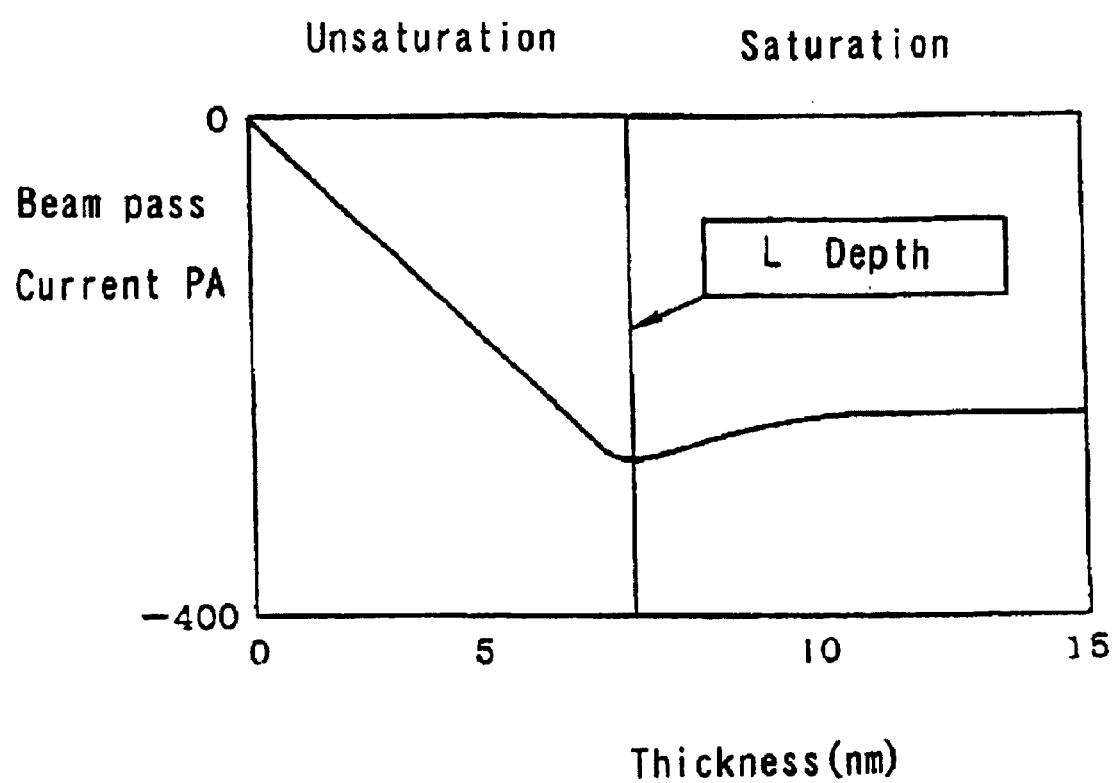
FIG. 18 is a diagram illustrative of variation in beam pass current over the silicon oxide film thickness.

FIG. 18 is a diagram illustrative of variation in beam pass current over the silicon oxide film thickness. The silicon oxide film 172 has a large secondary electron emission rate. More electrons than the injected electrons are emitted as secondary electrons from the silicon oxide film surface. If the thickness of the silicon oxide film 172 is zero, then this means that the electron beam is injected to the silicon substrate 171. As the thickness of the silicon oxide film 172 is increased up to the secondary electron escape depth L, the beam pass current is proportionally increased. This region is co called to as a proportional region. As the thickness of the silicon oxide film 172 is further increased from the secondary electron escape depth L, the beam pass current is saturated and almost remains unchanged because the beam pass current depends upon the secondary electron emission rate within the secondary electron escape depth L. If the silicon oxide film is extremely thick, the beam pass current is zero or almost zero.

If the electron beam acceleration voltage is constant, a ratio of the beam pass current to the thickness of the silicon oxide film is also constant. Therefore, the measurement of the beam pass current may estimate the thickness of the silicon oxide film. The secondary electron emission rate depends on the material of the film which thickness is intended to be measured, under the constant electron beam acceleration voltage. Measurement to the beam pass current under changing the electron beam acceleration voltage makes it possible to estimate the kinds of materials of the film.

Figure 19:
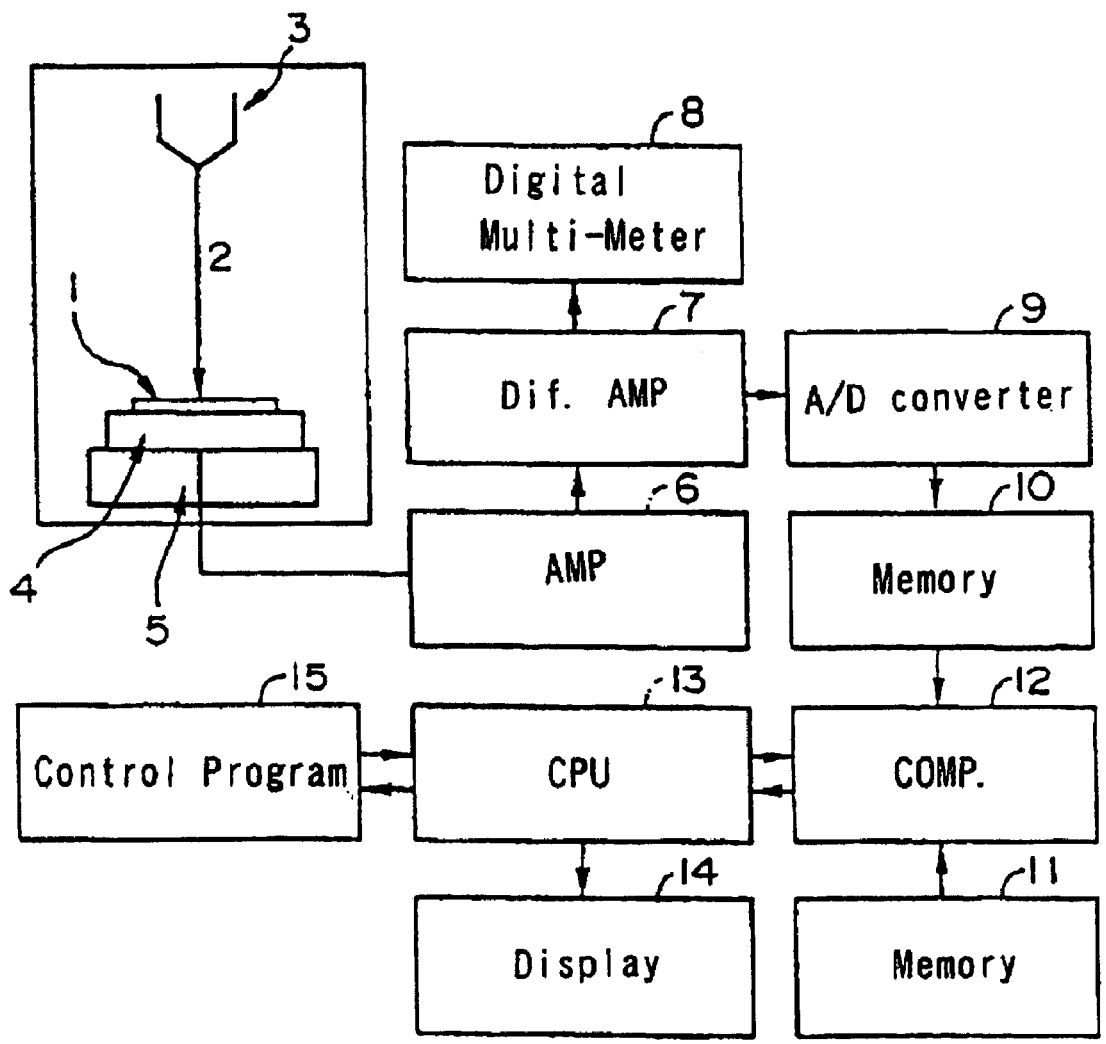
FIG. 19 is a block diagram illustrative of an apparatus for measuring a thickness of a thin film on a substrate in a sixteenth embodiment in accordance with the present invention.

FIG. 19 is a block diagram illustrative of an apparatus for measuring a thickness of a thin film on a substrate in a sixteenth embodiment in accordance with the present invention. The apparatus has an electron gun 3 which emits an electron beam 2 which is irradiated onto a thin film 1 provided on a substrate 4 which is placed on an electrode 5. The apparatus also has a current amplifier 6 connected to the electrode 5 for amplifying a beam pass current captured by the electrode 5. The apparatus also has a differential amplifier 7 connected to the current amplifier 6 for eliminating the off-set current from the amplified current value. The apparatus also has a digital multi-meter 8 connected to the differential amplifier 7 for monitoring the result. The apparatus also has an A/D converter 9 connected to the differential amplifier 7 for converting the analog signal as the output from the differential amplifier 7 to digital signals to be processed by a computer. The apparatus also has a first memory 10 connected to the A/D converter 9 for storing the digital signals from the A/D converter 9. The apparatus also has a second memory 11 for storing calibration curve data about the standard test device described in the foregoing embodiments. The apparatus also has a comparator 12 connected to the first and second memories 10 and 11 for comparing the measured digital data with the calibration curve data about the standard test device. The apparatus also has a CPU connected to the comparator 12 for controlling the operation of the comparator 12 in accordance with a control program 15, whereby the CPU calculates the estimated thickness of the thin film 1 from the comparison result from the comparator 12. The apparatus also has a display 14 connected to the CPU 13 for displaying the calculated thickness of the thin film 1. The thin film 1 is placed in a vacuum of not more than 1E10-4 mb.

Figure 20:
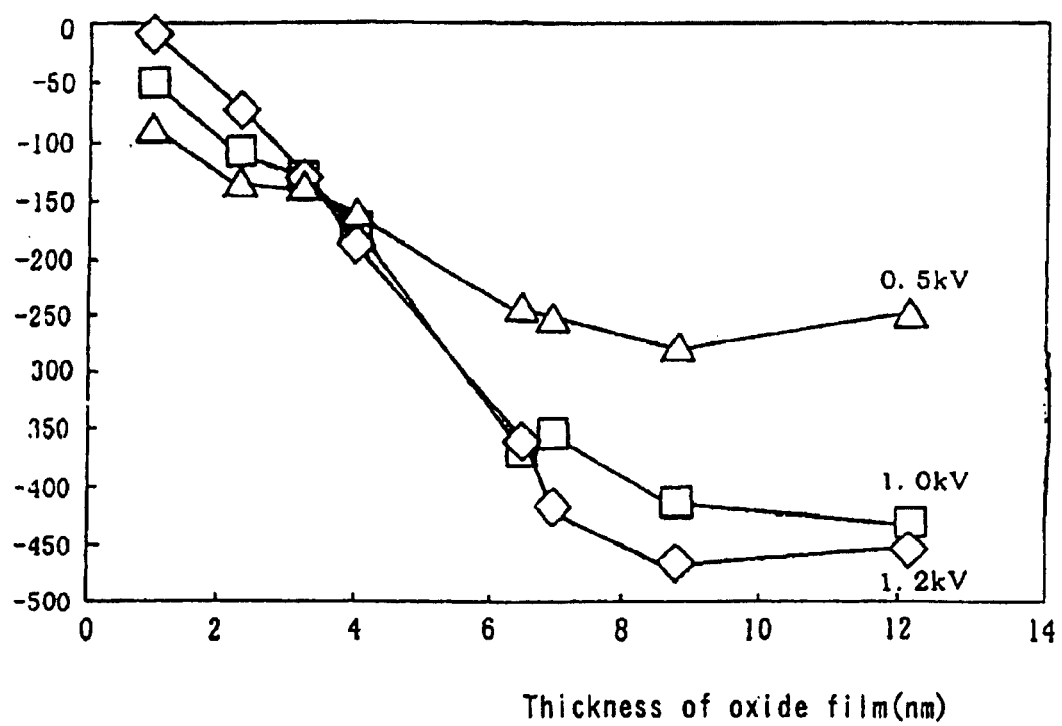
FIG. 20 is a diagram illustrative of a variation in beam pass current passing through a silicon oxide film over thickness of the silicon oxide film.

FIG. 20 is a diagram illustrative of a variation in beam pass current passing through a silicon oxide film over thickness of the silicon oxide film under three different electron beam acceleration voltages of 0.5 kV, 1.0 kV and 1.2 kV. As the thickness of the silicon oxide film is increased, then the beam pass current is also almost proportionally increased provided that the thickness of the silicon oxide film is below the secondary electron escape depth of about 10 nanometers. This region is unsaturated region. However, as the thickness of the silicon oxide film is increased from the secondary electron escape depth of about 10 nanometers, then the beam pass current almost remain unchanged. This region is the saturated region. As the electron beam acceleration voltage is high, then the variations in the beam pass current is large. This means that the increase in the electron beam acceleration voltage increases the detection sensitivity to the beam pass current. In the unsaturated region, the data of the variation in the beam pass current may be used for the calibration curve to estimate the thickness of the thin film.

Figure 21:
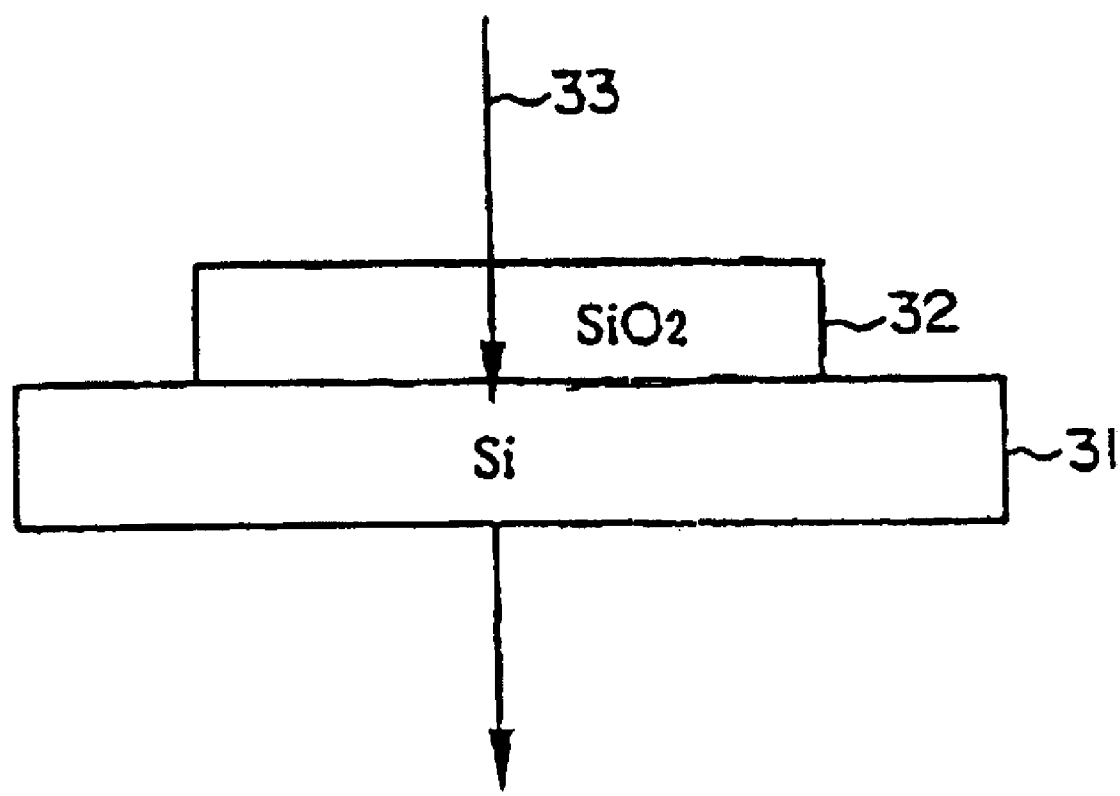
FIG. 21 is a fragmentary cross sectional elevation view illustrative of a sample to be measured in thickness by use of the thickness measuring system of FIG. 19.

FIG. 21 is a fragmentary cross sectional elevation view illustrative of a sample to be measured in thickness by use of the thickness measuring system of FIG. 19. A silicon oxide film 32 is provided on a silicon substrate 31. An electron beam 33 is irradiated onto a flat surface of the silicon oxide film 32. The silicon oxide film 32 has a thickness of not more than 1 nanometer. The beam spot area may be controlled narrowly and widely. The acceleration voltage of the electron beam may be about 1 kV. As the thickness of the silicon oxide film is increased, the secondary electron current is also increased, whereby the beam pass current is decreased. The angle of the electron beam axis to the surface of the silicon oxide film is kept constant.

Figure 22:
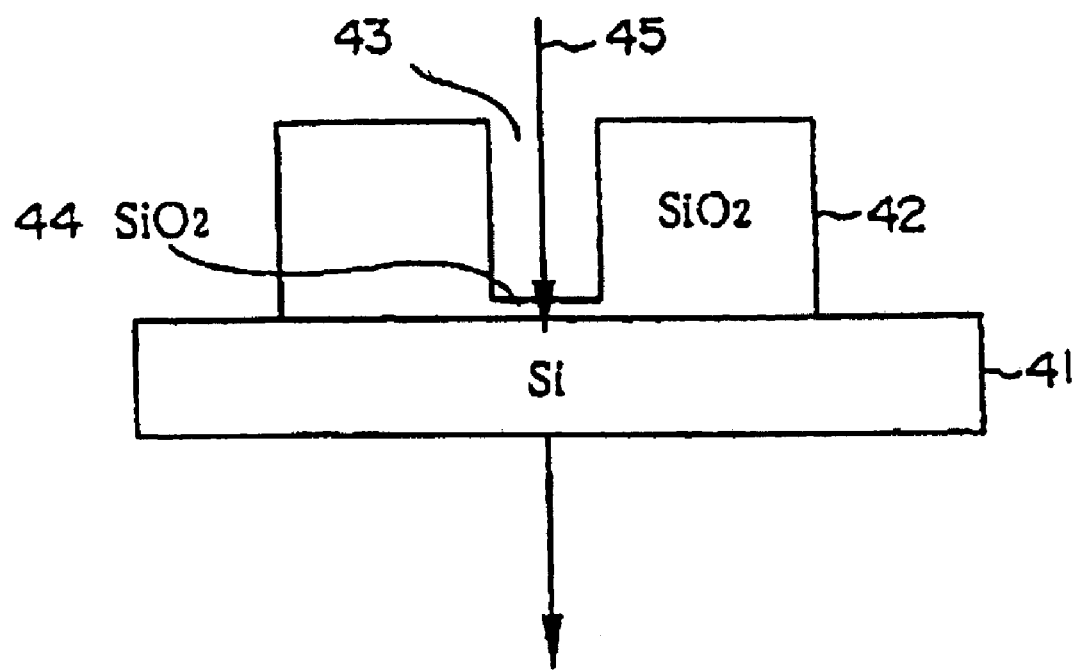
FIG. 22 is a fragmentary cross sectional elevation view illustrative of another sample to be measured in thickness by use of the thickness measuring system of FIG. 19.

FIG. 22 is a fragmentary cross sectional elevation view illustrative of another sample to be measured in thickness by use of the thickness measuring system of FIG. 19. A silicon oxide film 42 is provided on a silicon substrate 41. The silicon oxide film 42 has a hole 43 and a silicon oxide residual thin film 44 on a bottom of the hole 43. An electron beam 43 is irradiated onto the bottom of the hole 43 and on the silicon oxide residual thin film 44 to measure the thickness of the silicon oxide residual thin film 44. As the thickness of the silicon oxide film is increased, the secondary electron current is also increased, whereby the beam pass current is decreased. The angle of the electron beam axis to the surface of the silicon oxide film is kept constant.

Figure 23:
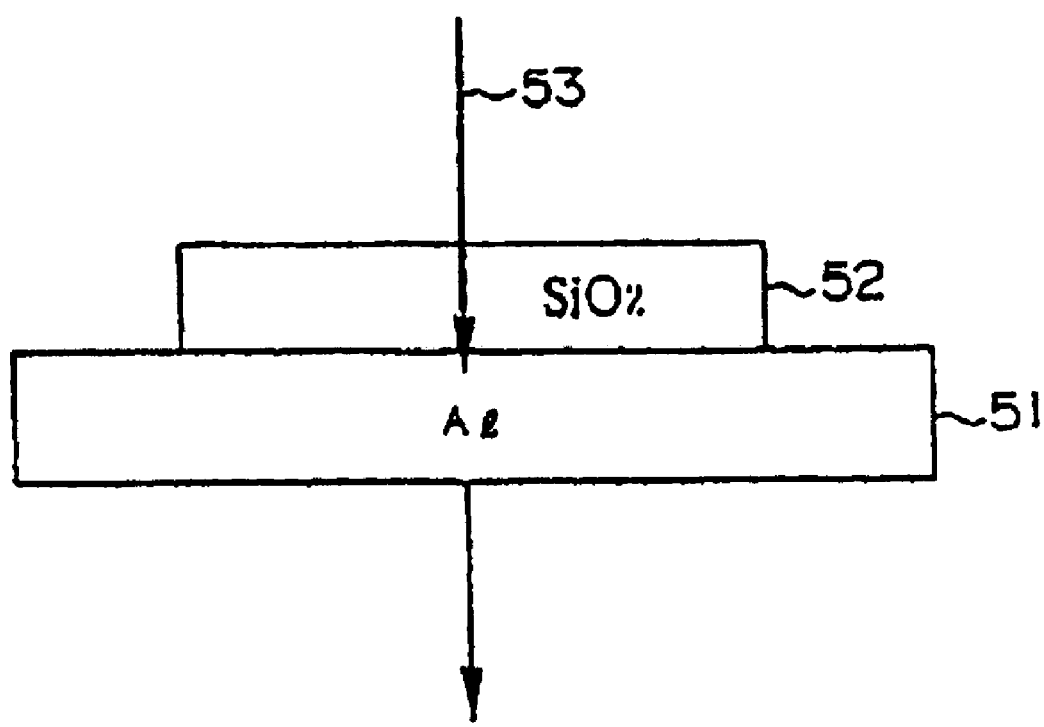
FIG. 23 is a fragmentary cross sectional elevation view illustrative of another sample to be measured in thickness by use of the thickness measuring system of FIG. 19.

FIG. 23 is a fragmentary cross sectional elevation view illustrative of another sample to be measured in thickness by use of the thickness measuring system of FIG. 19. A silicon oxide film 52 is provided on an aluminum interconnection layer 51. An electron beam 53 is irradiated onto a flat surface of the silicon oxide film 52. The silicon oxide film 52 has a thickness of not more than 1 nanometer. As the thickness of the silicon oxide film is increased, the secondary electron current is also, increased, whereby the beam pass current is decreased. The angle of the electron beam axis to the surface of the silicon oxide film is kept constant.

Figure 24:
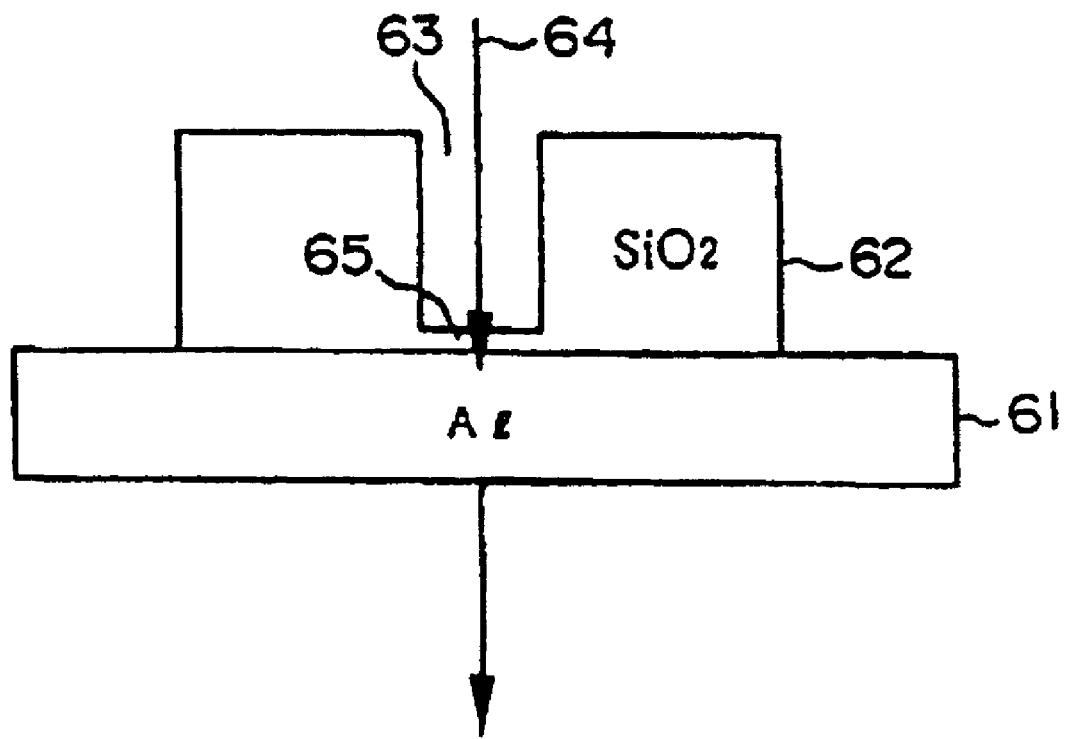
FIG. 24 is a fragmentary cross sectional elevation view illustrative of another sample to be measured in thickness by use of the thickness measuring system of FIG. 19.

FIG. 24 is a fragmentary cross sectional elevation view illustrative of another sample to be measured in thickness by use of the thickness measuring system of FIG. 19. A silicon oxide film 62 is provided on an aluminum interconnection layer 61. The silicon oxide film 62 has a hole 63 and a silicon oxide residual thin film 65 on a bottom of the hole 63. An electron beam 64 is irradiated onto the bottom of the hole 63 and on the silicon oxide residual thin film 65 to measure the thickness of the silicon oxide residual thin film 65. As the thickness of the silicon oxide film is increased, the secondary electron current is also increased, whereby the beam pass current is decreased. The angle of the electron beam axis to the surface of the silicon oxide film is kept constant.

Figure 25:
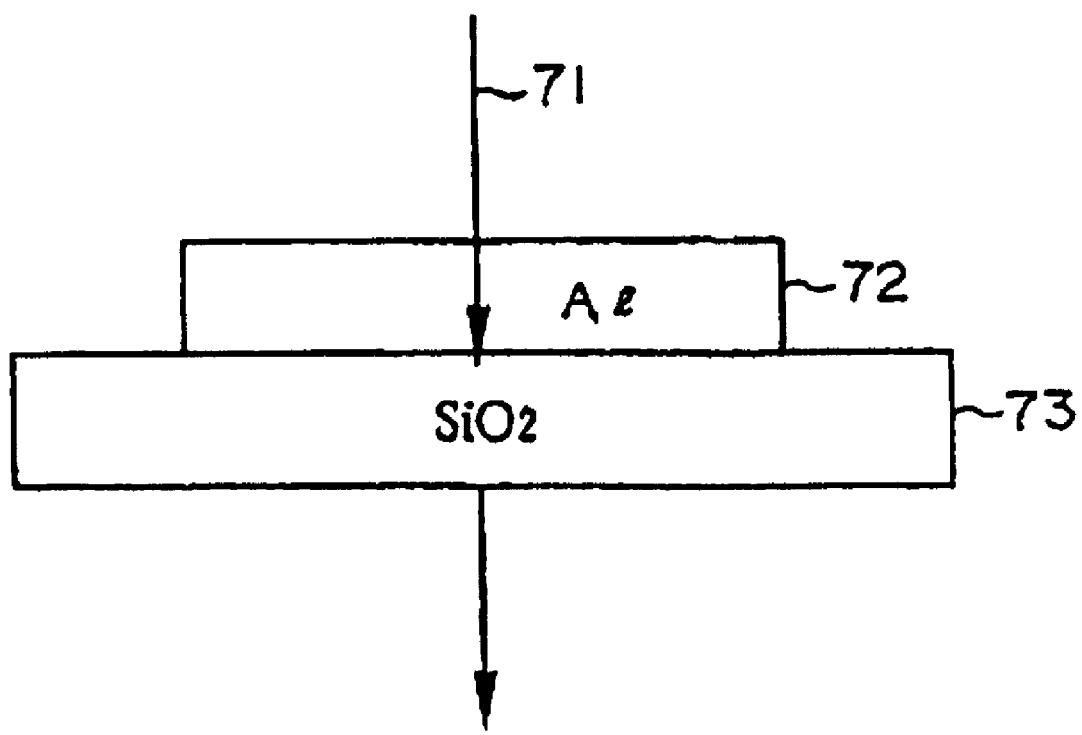
FIG. 25 is a fragmentary cross sectional elevation view illustrative of a sample to be measured in thickness by use of the thickness measuring system of FIG. 19.

FIG. 25 is a fragmentary cross sectional elevation view illustrative of a sample to be measured in thickness by use of the thickness measuring system of FIG. 19. An aluminum interconnection layer 72 is provided on a silicon oxide layer 73. An electron beam 71 is irradiated onto a flat surface of the aluminum interconnection layer 72. The aluminum interconnection layer 72 has a thickness in the order of 1 nanometer. The beam spot area may be controlled narrowly and widely. The aluminum interconnection layer 72 has a secondary electron emission rate of about 1. The silicon oxide layer 73 has a secondary electron emission rate of about 2–3. The beam pass current depends upon the thickness of the aluminum interconnection layer 72. As the thickness of the aluminum interconnection layer is increased, the beam pass current is increased. The angle of the electron beam axis to the surface of the silicon oxide film is kept constant.

Figure 26:
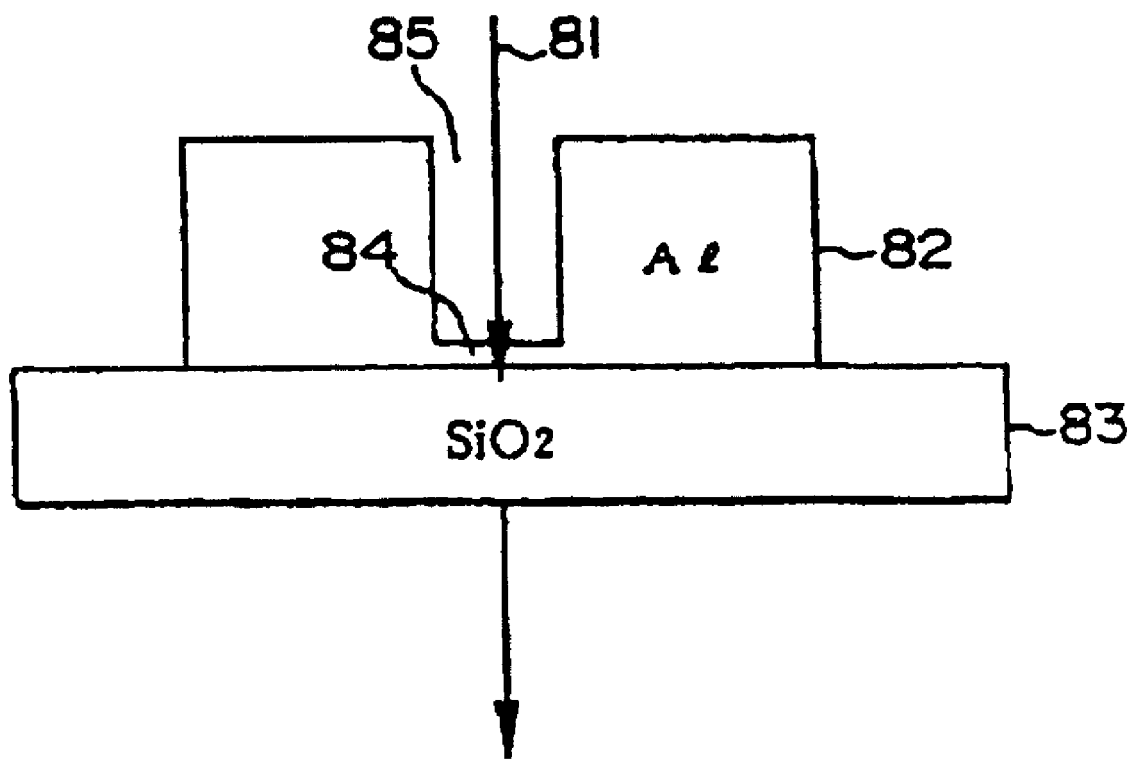
FIG. 26 is a fragmentary cross sectional elevation view illustrative of another sample to be measured in thickness by use of the thickness measuring system of FIG. 19.

FIG. 26 is a fragmentary cross sectional elevation view illustrative of another sample to be measured in thickness by use of the thickness measuring system of FIG. 19. An aluminum interconnection layer 82 is provided on a silicon oxide layer 83. The aluminum interconnection layer 82 has a hole 85 and an aluminum residual thin film 84 on a bottom of the hole 85. An electron beam 81 is irradiated onto the bottom of the hole 85 and on the aluminum residual thin film 84 to measure the thickness of the aluminum residual thin film 84. The aluminum interconnection layer 82 has a secondary electron emission rate of about 1. The silicon oxide layer 83 has a secondary electron emission rate of about 2–3. The beam pass current depends upon the thickness of the aluminum residual thin film 84. As the thickness of the aluminum residual thin film is increased, the beam pass current is increased. The angle of the electron beam axis to the surface of the silicon oxide film is kept constant.

Figure 27:
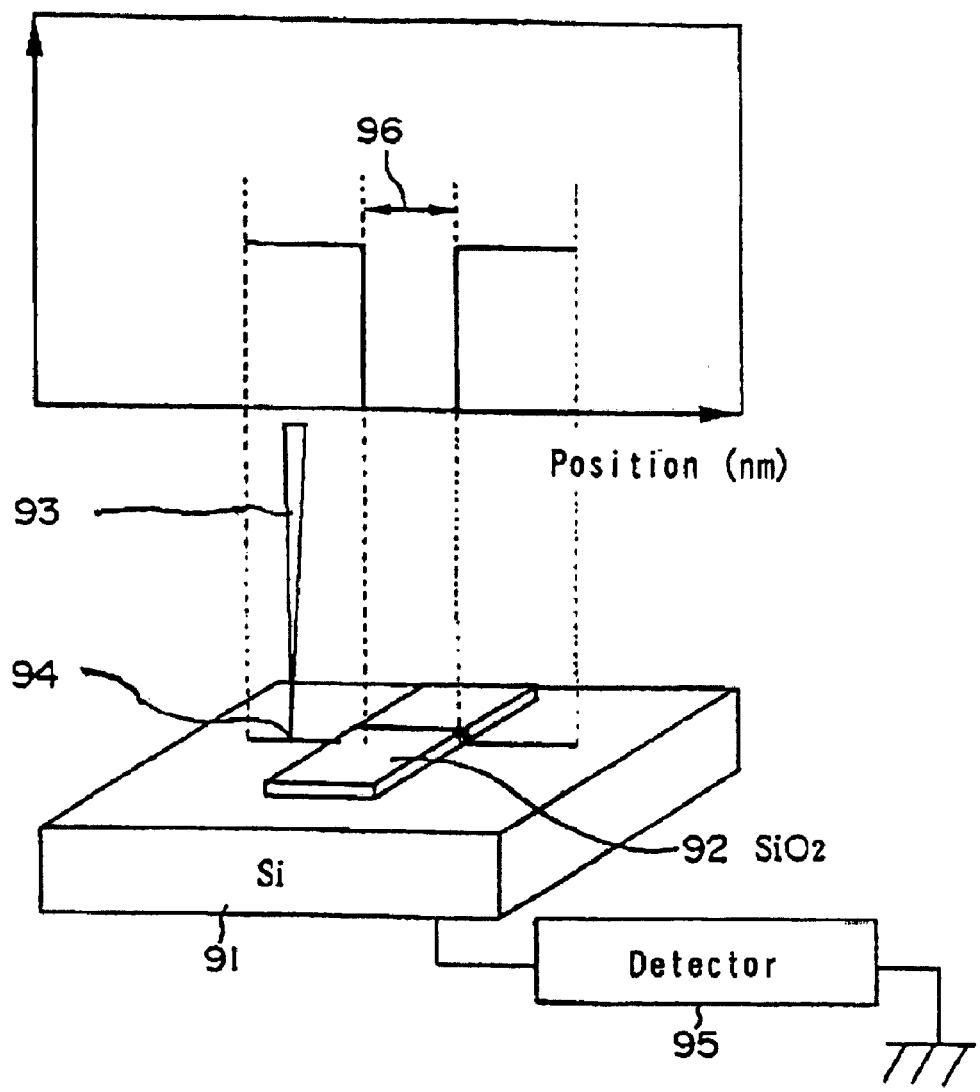
FIG. 27 is a schematic perspective view illustrative of a phenomenon of obtaining a thickness profile of a silicon oxide thin film on a silicon substrate by use of a thickness measuring system of FIG. 19 in a seventeenth embodiment in accordance with the present invention.

Seventeenth Embodiment:

A seventeenth embodiment according to the present invention will be described in detail with reference to the drawings. FIG. 27 is a schematic perspective view illustrative of a phenomenon of obtaining a thickness profile of a silicon oxide thin film on a silicon substrate by use of a thickness measuring system of FIG. 19. A silicon oxide film 92 is provided on the silicon substrate 91. An electron beam 93 is irradiated with scanning on a one-dimensional scanning line 94 which across the silicon oxide film 92 in a width direction to measure the thickness of the silicon oxide film 92. The electron gun is moved so that electron beam 93 is scanned or the substrate stage is moved so that the electron beam 93 is scanned. If the electron beam 93 is irradiated on the silicon substrate 91, then the measured thickness is zero. If the electron beam 93 is irradiated on the silicon oxide film 92, then the measured thickness is not zero and is of the silicon oxide film 92, whereby the scanning of the electron beam in the pattern width direction makes it possible to determine a pattern width 96 of the silicon oxide film 92 in addition to the thickness of the silicon oxide film 92.

Figure 28:
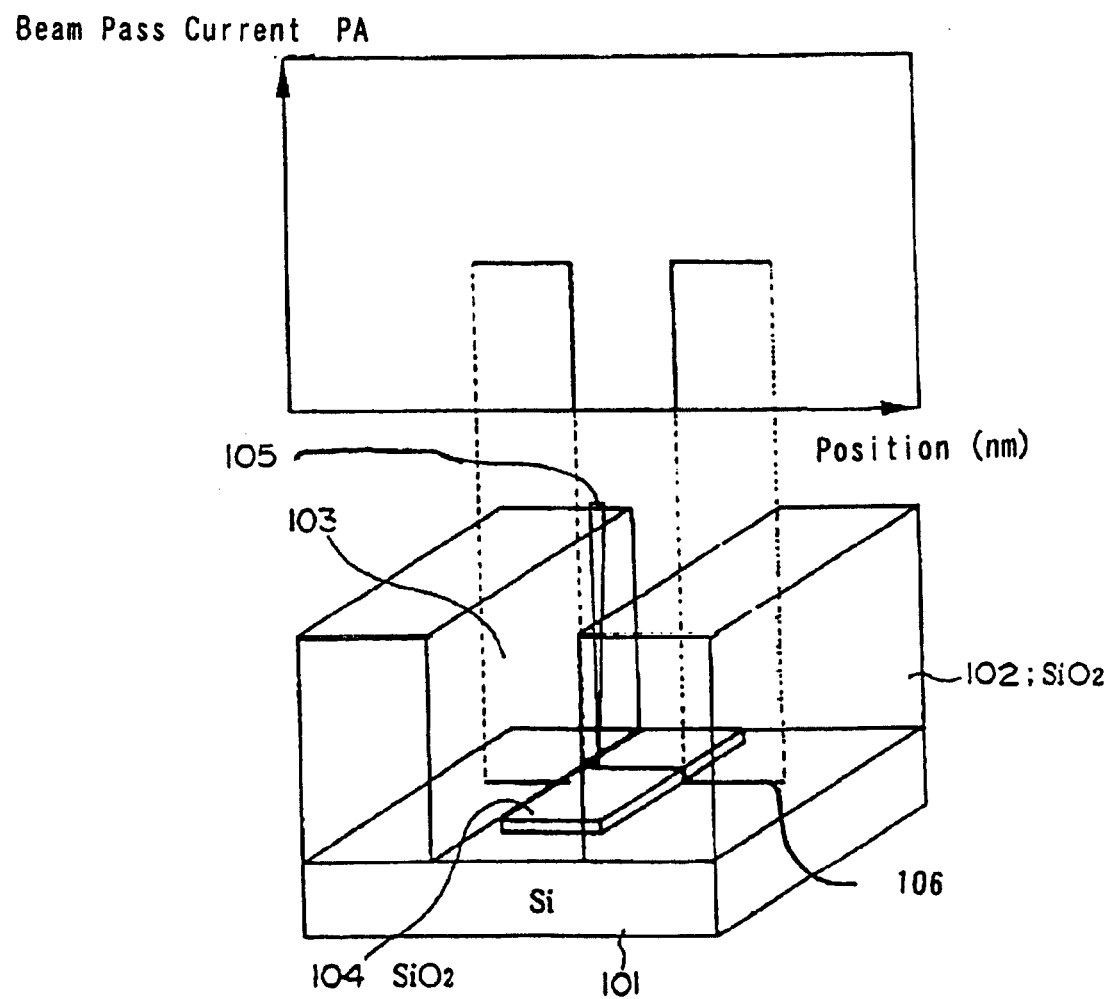
FIG. 28 is a schematic perspective view illustrative of a phenomenon of obtaining a thickness profile of a silicon oxide thin film on a silicon substrate by use of a thickness measuring system of FIG. 19 in an eighteenth embodiment in accordance with the present invention.

Eighteenth Embodiment:

An eighteenth embodiment according to the present invention will be described in detail with reference to the drawings. FIG. 28 is a schematic perspective view illustrative of a phenomenon of obtaining a thickness profile of a silicon oxide thin film on a silicon substrate by use of a thickness measuring system of FIG. 19. A thick silicon oxide film 102 is provided on the silicon substrate 101. The thick silicon oxide film 102 has a hole 103 and a thin residual silicon oxide film 104 on a bottom of the hole 103. An electron beam 105 is irradiated with scanning on a one-dimensional scanning line 106 which across the thick silicon oxide film 102 and the thin residual silicon oxide film 104 in a width direction to measure the thickness of the thin residual silicon oxide film 104. The electron gun is moved so that electron beam 105 is scanned or the substrate stage is moved so that the electron beam 105 is scanned. If the eletron beam 105 is irradiated on the thick silicon oxide film 102, then the measured thickness is such large as the thick silicon oxide film 102. If the electron beam 105 is irradiated on the thin residual silicon oxide film 104, then the measured thickness is such small as the thin residual silicon oxide film 104, whereby the scanning of the electron beam in the pattern width direction makes it possible to determine a width of the hole 103 and a width of the thin residual silicon oxide film 104 in addition to the thickness of the thin residual silicon oxide film 104.

Figure 29:
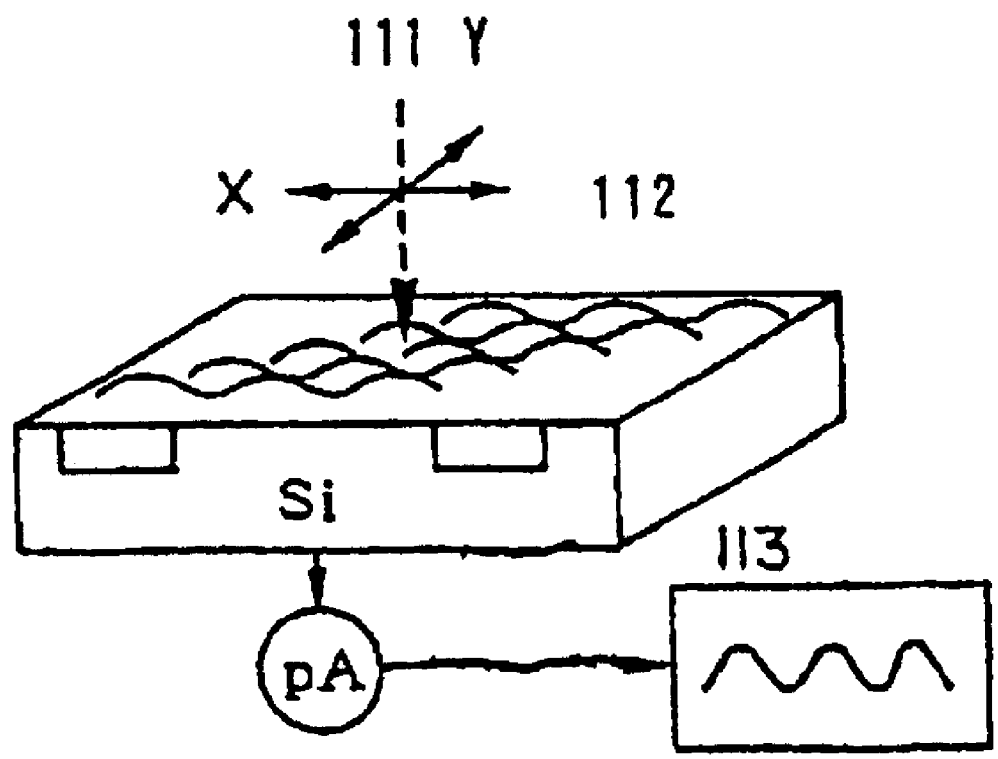
FIG. 29 is a schematic perspective view illustrative of a phenomenon of obtaining a thickness profile of a silicon oxide thin film on a silicon substrate by use of a thickness measuring system of FIG. 19 in a nineteenth embodiment in accordance with the present invention.

Nineteenth Embodiment:

A nineteenth embodiment according to the present invention will be described in detail with reference to the drawings. FIG. 29 is a schematic perspective view illustrative of a phenomenon of obtaining a thickness profile of a silicon oxide thin film on a silicon substrate by use of a thickness measuring system of FIG. 19. In this embodiment, the electron beam is irradiated onto a sample in two-dimensional scanning so as to obtain an information about two-dimensional distribution of thickness of the film over a substrate. The electron beam 111 is scanned in two-dimensional coordinate 112.

Twentieth Embodiment:

A twentieth embodiment according to the present invention will be described in detail with reference to the drawings. In this embodiment, the thickness of the thin film on the multi-layered structure over a substrate is measured by the novel thickness measuring system of FIG. 19.

Figure 30:
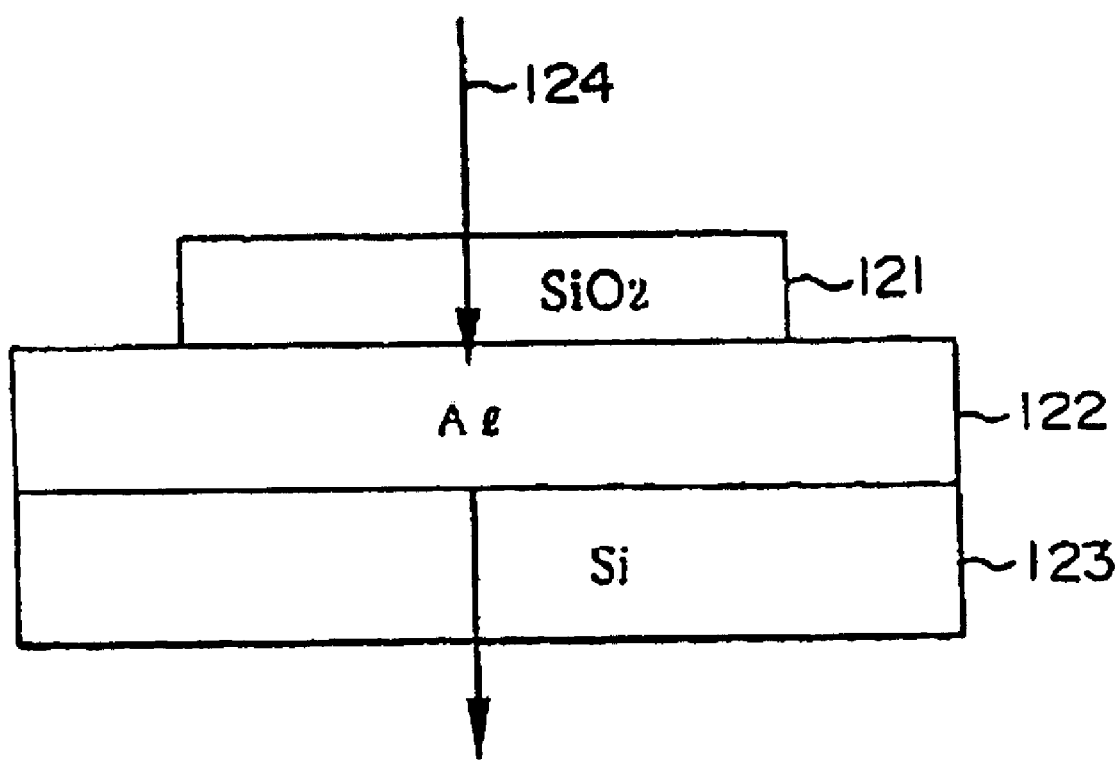
FIG. 30 is a fragmentary cross sectional elevation view illustrative of a multi-layered structure sample to be measured in thickness by use of the thickness measuring system of FIG. 19 in a twentieth embodiment in accordance with the present invention.

FIG. 30 is a fragmentary cross sectional elevation view illustrative of a multi-layered structure sample to be measured in thickness by use of the thickness measuring system of FIG. 19. An aluminum interconnection layer 122 is provided on a silicon substrate 123. A silicon oxide film 121 is provided on the aluminum interconnection layer 122. An electron beam 124 is irradiated onto a flat surface of the silicon oxide film 121. The electron beam 124 is emitted by an acceleration voltage of 1 kV so that the electron beam 124 reaches a depth of about 50 nanometers from the surface of the silicon oxide film 121. As described above, however, the beam pass current depends on the secondary electron emission rate of the materials existing within the depth of 10 nanometers from the surface. The silicon oxide film 121 and the aluminum interconnection layer 122 are different in secondary electron emission rate, for which reason the secondary electrons are emitted proportionally to the thickness of the silicon oxide film 121, whereby the beam pass current also depends on the thickness of the silicon oxide film 121. If the depth of the top surface of the silicon substrate 123 is deeper than 10 nanometers as the secondary electron escape depth, then the secondary electron emission depends on both the silicon oxide film 121 and the aluminum interconnection layer 122. The calibration data of silicon oxide and aluminum are used for determine the thickness of the silicon oxide film 121.

Figure 31:
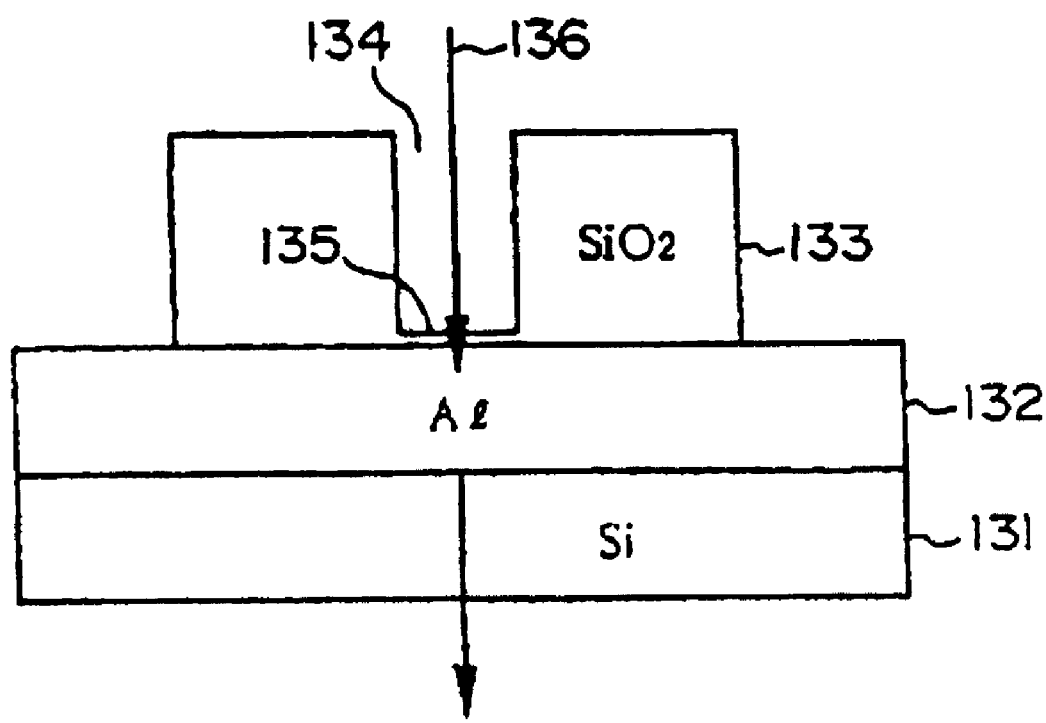
FIG. 31 is a fragmentary cross sectional elevation view illustrative of another multi-layered structure sample to be measured in thickness by use of the thickness measuring system of FIG. 19 in a twentieth embodiment in accordance with the present invention.

FIG. 31 is a fragmentary cross sectional elevation view illustrative of another multi-layered structure sample to be measured in thickness by use of the thickness measuring system of FIG. 19. An aluminum interconnection layer 132 is provided on a silicon substrate 131. A thick silicon oxide film 133 is provided on the aluminum interconnection layer 132. The thick silicon oxide film 133 has a hole 134 and a thin residual silicon oxide film 135 on a bottom of the hole 134. An electron beam 136 is irradiated onto the thin residual silicon oxide film 135 on the bottom of the hole 134. As described above, however, the beam pass current depends on the secondary electron emission rate of the materials existing within the depth of 10 nanometers from the surface. The silicon oxide and the aluminum are different in secondary electron emission rate, for which reason the secondary electrons are emitted proportionally to the thickness of the thin residual silicon oxide film 135, whereby the beam pass current also depends on the thickness of the thin residual silicon oxide film 135. If the depth of the top surface of the silicon substrate 131 is deeper than 10 nanometers as the secondary electron escape depth, then the secondary electron emission depends on both the thicknesses of the thin residual silicon oxide film 135 and the aluminum interconnection layer 122. The calibration data of silicon oxide and aluminum are used for determine the thickness of the thin residual silicon oxide film 135. If, however, the depth of the top surface of the silicon substrate 131 is shallower than 10 nanometers as the secondary electron escape depth, then the secondary electron emission depends on not only both the thin residual silicon oxide film 135 and the aluminum interconnection layer 132 but also the silicon substrate 131. The calibration data of silicon oxide, aluminum and silicon are used for determine the thickness of the thin residual silicon oxide film 135.

Figure 32:
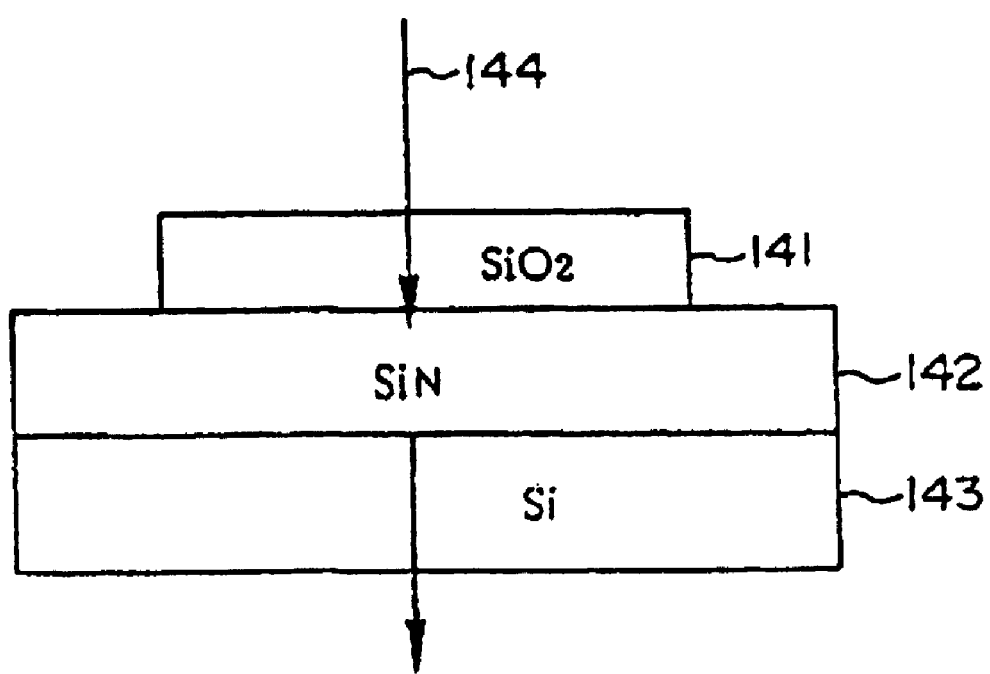
FIG. 32 is a fragmentary cross sectional elevation view illustrative of another multi-layered structure sample to be measured in thickness by use of the thickness measuring system of FIG. 19 in a twentieth embodiment in accordance with the present invention.

FIG. 32 is a fragmentary cross sectional elevation view illustrative of another multi-layered structure sample to be measured in thickness by use of the thickness measuring system of FIG. 19. A silicon nitride layer 142 is provided on a silicon substrate 143. A silicon oxide film 141 is provided on the silicon nitride layer 142. An electron beam 144 is irradiated onto a flat surface of the silicon oxide film 141. The electron beam 144 is emitted by an acceleration voltage of 1 kV so that the electron beam 144 reaches a depth of about 50 nanometers from the surface of the silicon oxide film 141. As described above, however, the beam pass current depends on the secondary electron emission rate of the materials existing within the depth of 10 nanometers from the surface. The silicon oxide film 141 and the silicon nitride layer 142 are different in secondary electron emission rate, for which reason the secondary electrons are emitted proportionally to the thickness of the silicon oxide film 141, whereby the beam pass current also depends on the thickness of the silicon oxide film 141. If the depth of the top surface of the silicon substrate 143 is deeper than 10 nanometers as the secondary electron escape depth, then the secondary electron emission depends on both the silicon oxide film 141 and the silicon nitride layer 142. The calibration data of silicon oxide and silicon nitride are used for determine the thickness of the silicon oxide film 141.

Figure 33:
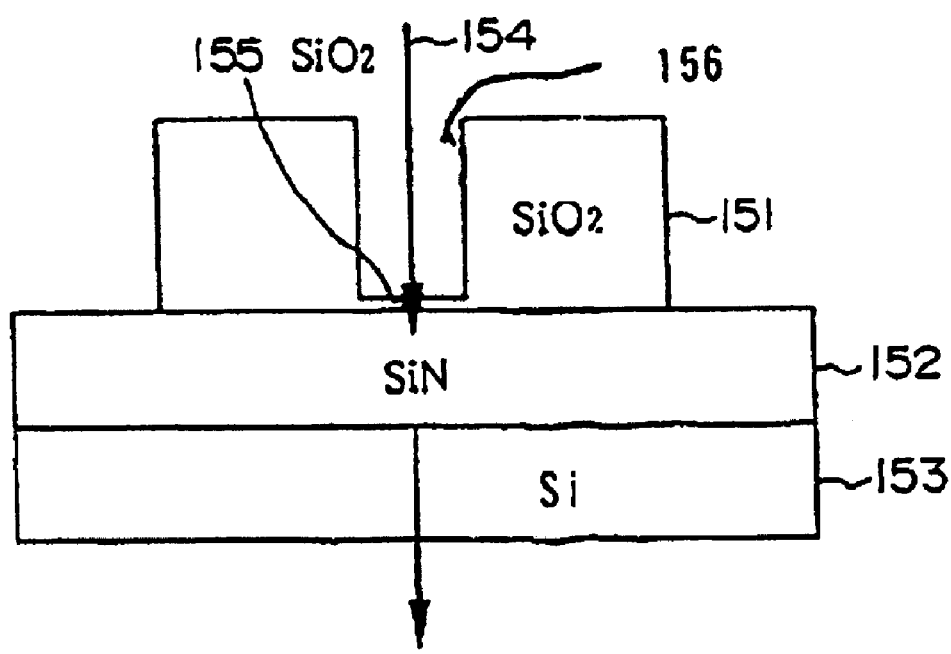
FIG. 33 is a fragmentary cross sectional elevation view illustrative of another multi-layered structure sample to be measured in thickness by use of the thickness measuring system of FIG. 19 in a twentieth embodiment in accordance with the present invention.

FIG. 33 is a fragmentary cross sectional elevation view illustrative of another multi-layered structure sample to be measured in thickness by use of the thickness measuring system of FIG. 19. A silicon nitride layer 152 is provided on a silicon substrate 153. A thick silicon oxide film 151 is provided on the silicon nitride layer 152. The thick silicon oxide film 151 has a hole 156 and a thin residual silicon oxide film 155 on a bottom of the hole 156. An electron beam 154 is irradiated onto the thin residual silicon oxide film 155 on the bottom of the hole 156. As described above, however, the beam pass current depends on the secondary electron emission rate of the materials existing within the depth of 10 nanometers from the surface. The silicon oxide and the silicon nitride are different in secondary electron emission rate, for which reason the secondary electrons are emitted proportionally to the thickness of the thin residual silicon oxide film 155, whereby the beam pass current also depends on the thickness of the thin residual silicon oxide film 155. If the depth of the top surface of the silicon substrate 153 is deeper than 10 nanometers as the secondary electron escape depth, then the secondary electron emission depends on both the thin residual silicon oxide film 155 and the silicon nitride layer 152. The calibration data of silicon oxide and silicon nitride are used for determine the thickness of the thin residual silicon oxide film 155. If, however, the depth of the top surface of the silicon substrate 153 is shallower than 10 nanometers as the secondary electron escape depth, then the secondary electron emission depends on not only both the thin residual silicon oxide film 155 and the silicon nitride layer 152 but also the silicon substrate 153. The calibration data of silicon oxide, silicon nitride and silicon are used for determine the thickness of the thin residual silicon oxide film 155.

Twenty First Embodiment:

A twenty first embodiment according to the present invention will be described in detail with reference to the drawings. In this embodiment, not only the beam pass current but also the secondary electrons are detected.

Figure 34:
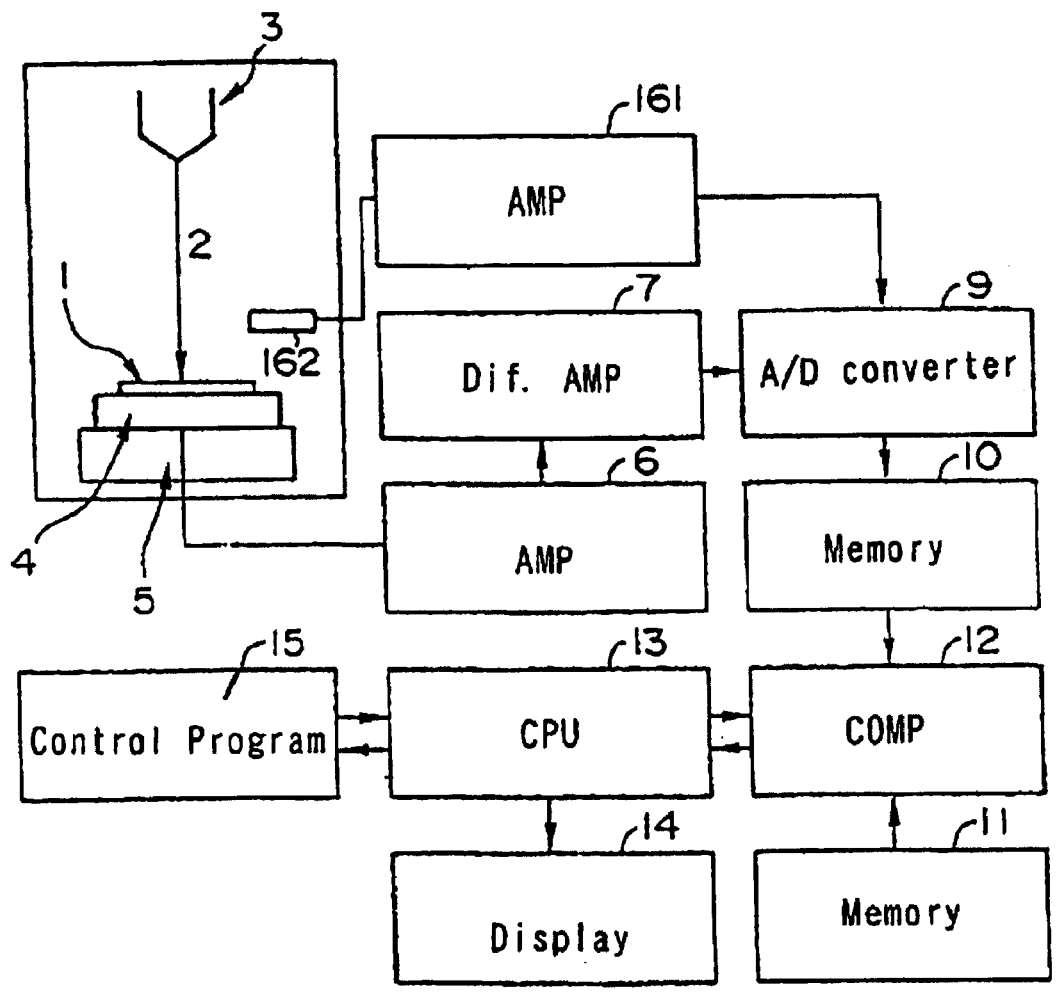
FIG. 34 is a block diagram illustrative of an apparatus for measuring a thickness of a thin film on a substrate in a twenty first embodiment in accordance with the present invention.

FIG. 34 is a block diagram illustrative of an apparatus for measuring a thickness of a thin film on a substrate in a twenty first embodiment in accordance with the present invention. The apparatus has an electron gun 3 which emits an electron beam 2 which is irradiated onto a thin film 1 provided on a substrate 4 which is placed on an electrode 5. The apparatus also has a current amplifier 6 connected to the electrode 5 for amplifying a beam pass current captured by the electrode 5. The apparatus also has a differential amplifier 7 connected to the current amplifier 6 for eliminating the off-set current from the amplified current value. The apparatus also has a secondary electron detector 162 for detecting secondary electrons emitted from the surface of the thin film. The apparatus also has a signal amplifier 161 connected to the secondary electron detector 162 for amplifying the secondary electron detected signal from the secondary electron detector 162. The apparatus also has an A/D converter 9 connected to the differential amplifier 7 for converting the analog signal as the output from the differential amplifier 7 to digital signals to be processed by a computer. The A/D converter 9 is also connected to the signal amplifier 161 for converting the secondary electron detected signal to digital signals to be processed by a computer. The apparatus also has a first memory 10 connected to the A/D converter 9 for storing the digital signals from the A/D converter 9. The apparatus also has a second memory 11 for storing calibration curve data about the standard test device described in the foregoing embodiments. The apparatus also has a comparator 12 connected to the first and second memories 10 and 11 for comparing the measured digital data with the calibration curve data about the standard test device. The apparatus also has a CPU connected to the comparator 12 for controlling the operation of the comparator 12 in accordance with a control program 15, whereby the CPU calculates the estimated thickness of the thin film 1 from the comparison result from the comparator 12. The apparatus also has a display 14 connected to the CPU 13 for displaying the calculated thickness of the thin film 1. This apparatus is capable of measuring not only the beam pass current but also the secondary electron current.

When the electron beam is irradiated on a surface of a substance, the electrons are isolated into secondary electrons and beam pass current which have an inter-relation given by the above equation (1). A ratio of the secondary electrons and beam pass current depends upon the secondary electron emission rate and the thickness of the substance, wherein the secondary electron emission rate also depends on the material of the substance. If the calibration curves for the secondary electron emission and the beam pass current are used to determine measuring parameters of the secondary electron emission and the beam pass current, whereby an accuracy in measurement in thickness of the substance may be improved.

Further, if the secondary electron emission rate of the substance has previously been known, it is possible to analyze the material of the sample.

The above thickness measuring apparatus in accordance with the present invention, for example, as shown in FIGS. 19 and 34 are capable of measuring a thickness of an extremely thin film in the nanometer order, and also capable of measuring a thickness of a film on a bottom of a hole having an extremely high aspect ratio of not less than 5.

The above thickness measuring apparatus are also capable of measuring a thickness of a top film on a multi-layered structure. The above thickness measuring apparatus are also capable of measuring a film made of various materials, for example, silicon, silicon oxide, aluminum, W, Mo, Pt, Au, Cu, Ti, silicide, nitride ferromagnetic, polyimide, resist, fluoro-carbon, carbon, protein, DNA.

It is preferable that the acceleration voltage of the electron beam is so selected that a ratio in secondary electron emission rate of the top film and an underlying film underling the top film is largest.

Figure 35:
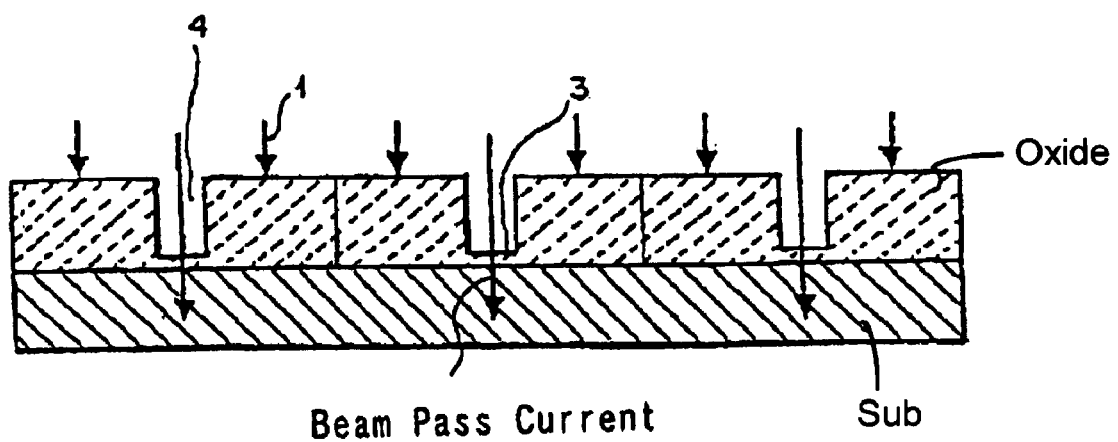
FIG. 35 is a fragmentary cross sectional elevation view illustrative of a first method of measuring the thickness of the film or the residual film on the bottom of the contact hole by measuring the secondary electron current in a twenty second embodiment in accordance with the present invention.
Figure 36:
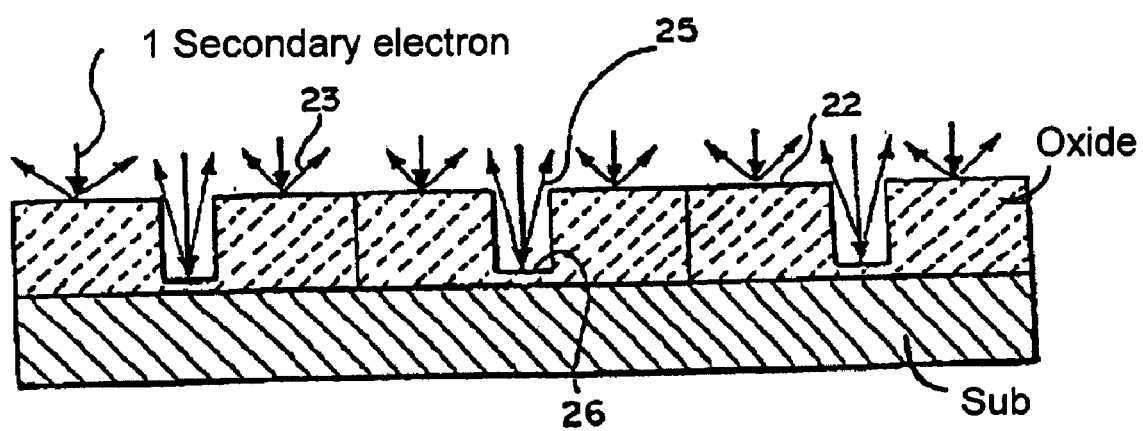
FIG. 36 is a fragmentary cross sectional elevation view illustrative of a first method of measuring the thickness of the film or the residual film on the bottom of the contact hole by measuring the beam pass current in a twenty second embodiment in accordance with the present invention.

Twenty Second Embodiment:

A twenty second embodiment according to the present invention will be described in detail with reference to the drawings. In this embodiment, a novel method of checking whether or not a large number of contact holes on a semiconductor wafer are defective. If any residual film resides on a bottom of the contact hole, then this contact hole is defective. Namely, the method of checking the contact hole is to measure the thickness of the residual film on the bottom of the contact hole. As described above, there are two available methods of measuring the thickness of the film or the residual film on the bottom of the contact hole. The first one is to measure the secondary electron current emitted from a surface of the residual film upon irradiation of an electron beam thereon. The second one is to measure the beam pass current. FIG. 35 is a fragmentary cross sectional elevation view illustrative of a first method of measuring the thickness of the film or the residual film on the bottom of the contact hole by measuring the secondary electron current. FIG. 36 is a fragmentary cross sectional elevation view illustrative of a first method of measuring the thickness of the film or the residual film on the bottom of the contact hole by measuring the beam pass current. In this embodiment, the first method is selected as shown in FIG. 35.

A probability of defective contact hole is extremely low. The measurement of all the contact holes are time consuming and non-efficient procedures. In accordance with the present invention, the semiconductor wafer having a large number of contact holes are divided into a plurality of blocks, so that the electron beam is irradiated onto each of the blocks, thereby estimating defective blocks which have defective contact holes. The beam pass current passed through the block measured and then compared with a threshold value to detect a difference between them. If no defective contact hole exists in the block namely all of the contact holes in the block are perfect, then the beam pass current is maximum Imax. If any of the contact holes in the block are defective, then the beam pass current is lower than the maximum Imax. If the actually measured current value is given by lines and the number of the contact holes in the block is "N", then the estimated number of the defective contact holes is given by N(Imax-Imes)/Imax.

Figure 37:
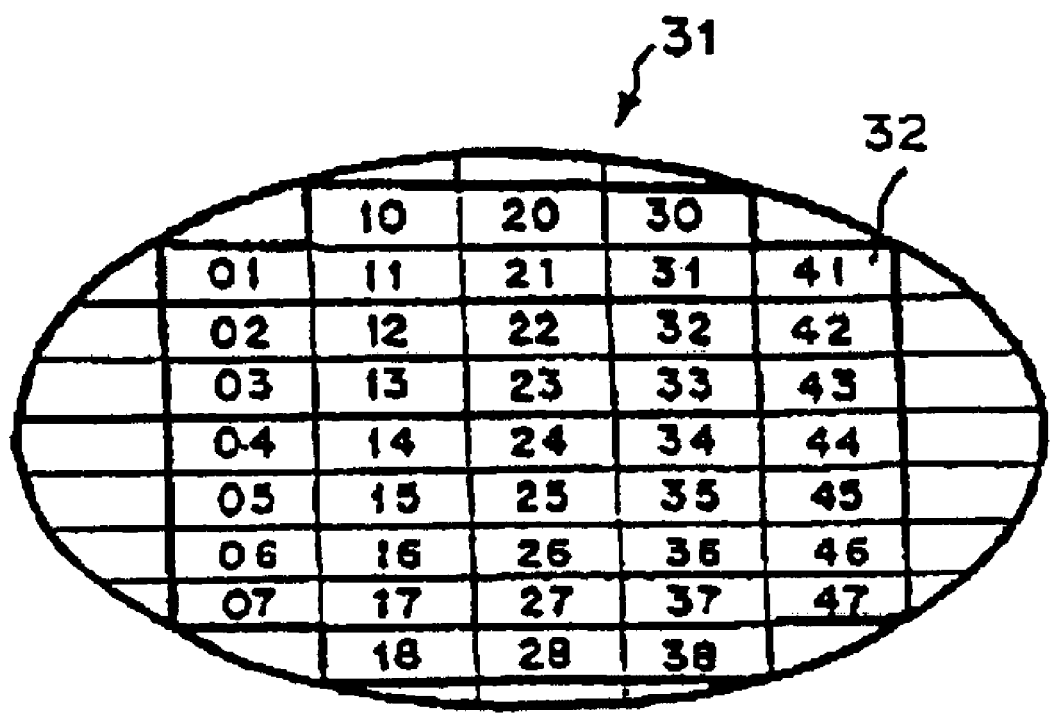
FIG. 37 is a plane view illustrative of a semiconductor wafer which is divided into blocks which are allocated with sequential identification numbers in a twenty second embodiment in accordance with the present invention.
Figure 38:
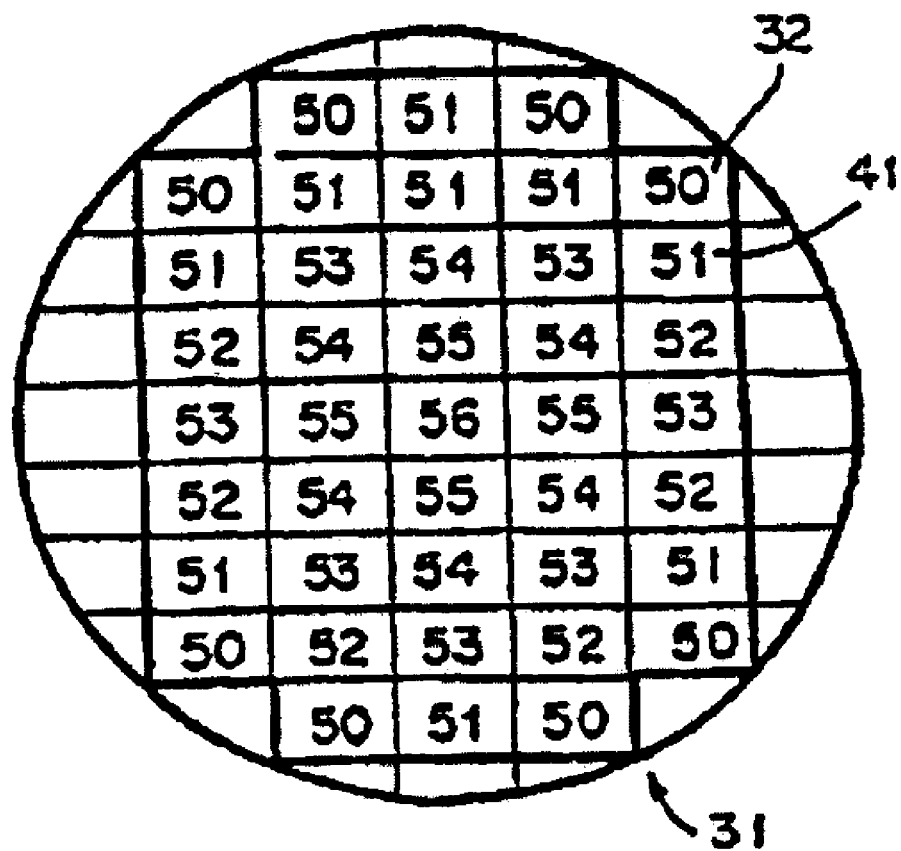
FIG. 38 is a plane view illustrative of a semiconductor wafer divided into blocks on which measured beam pass current values are displayed on the basis of FIG. 37 in a twenty second embodiment in accordance with the present invention.

FIG. 37 is a plane view illustrative of a semiconductor wafer which is divided into blocks which are allocated with sequential identification numbers. The semiconductor wafer 31 is divided into blocks 32 which have the same size as chips or function blocks. Individual blocks 32 are allocated with sequential identification numbers. The electron beams are irradiated onto the individual blocks 32 to measure the individual beam pass currents. FIG. 38 is a plane view illustrative of a semiconductor wafer divided into blocks on which measured beam pass current values are displayed on the basis of FIG. 37. The measured beam pass current values 41 are displayed on corresponding positions to the individual blocks 32 so that a bit map showing defective contact hole distribution can be obtained. FIG. 39 is a table on which the measured beam pass current values and the identification numbers allocated to the corresponding blocks in order of magnitude of the measured beam pass current value on the basis of FIG. 38.

Figure 40:
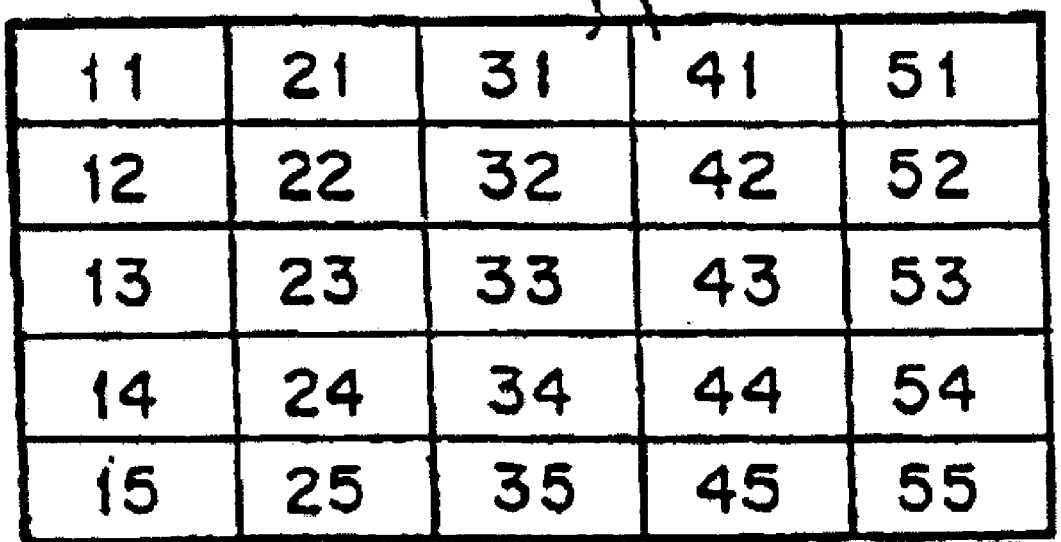
FIG. 40 is a plane view illustrative of one block in FIG. 37 which is further divided into plural sub-blocks which are allocated with identification numbers in a twenty second embodiment in accordance with the present invention.
Figure 41:
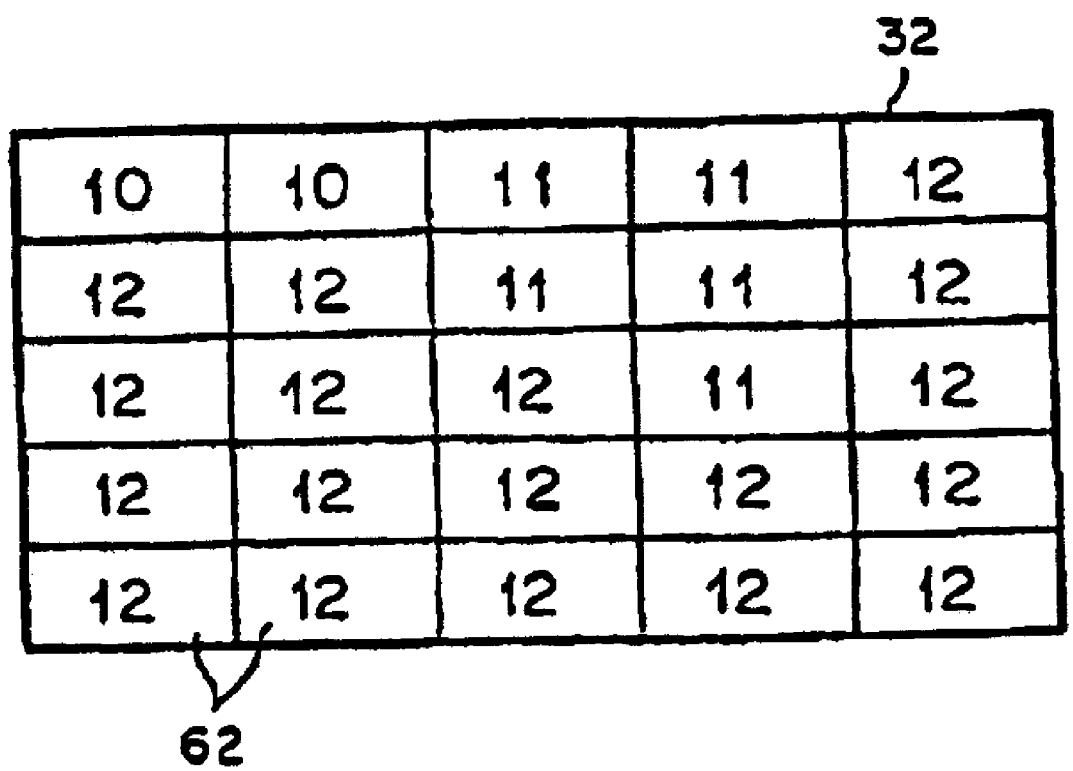
FIG. 41 is a plane view illustrative of the block divided into sub-blocks on which measured beam pass current values are displayed on the basis of FIG. 40 in a twenty second embodiment in accordance with the present invention.

If the measured beam pass current is smaller, then the number of the defective contact hole is larger. The checking to the individual contact holes are carried out from the block which measured beam pass current is smallest. Each of the blocks 32 is further divided into sub-blocks 62 which have a size of not larger than 100 micrometars square. FIG. 40 is a plane view illustrative of one block in FIG. 37 which is further divided into plural sub-blocks which are allocated with identification numbers. The individual sub-blocks are allocated with identification numbers. If the measured beam pass current of the sub-block is smaller, then the number of the defective contact hole in the sub-block is larger. FIG. 41 is a plane view illustrative of the block divided into sub-blocks on which measured beam pass current values are displayed on the basis of FIG. 40. The measured beam pass current values of the sub-blocks 62 in the block 32 are displayed on corresponding positions to the individual sub-blocks 32 so that a bit map showing defective contact hole distribution can be obtained. The bit map is subjected to a statistical calculation to obtain an average value and a standard deviation of the beam pass currents. If any of the sub-blocks 62 has a lower beam pass current then the threshold value, then individual contact holes are checked by irradiating an electron beam onto a bottom of the contact hole to measure the thickness of the residual film on the contact hole bottom. The individual sub-blocks are ordered in order of the measured beam pass current. FIG. 42 is a table on which the measured beam pass current values and the identification numbers allocated to the corresponding sub-blocks in order of magnitude of the measured beam pass current value on the basis of FIG. 41.

In accordance with the present invention, only the contact holes are finally checked which are formed in the suspected sub-block which shows the smaller beam pass current than the threshold value, whereby other contact holes formed in the unsuspected blocks and in the unsuspected sub-blocks in the suspected blocks are not checked. This hierarchical checking processes are capable of shortening the necessary time for defecting all of the defective contact holes.

A statistical analysis to the defective contact holes over position is made, so that a probability distribution of appearance of the defective contact holes over position can be confirmed. The checking is first made to the position where the probability of appearance of the defective contact holes is high.

Under the mass-production, if the number of the detected defective contact holes is beyond the predetermined threshold number, then this wafer is removed from the manufacturing line. Therefore, the block being lower than the standard value in the number of the defective contact holes is allowed to go on the manufacturing line. The block being higher than the standard value in the number of the defective contact holes is removed from the manufacturing line.

Figure 43:
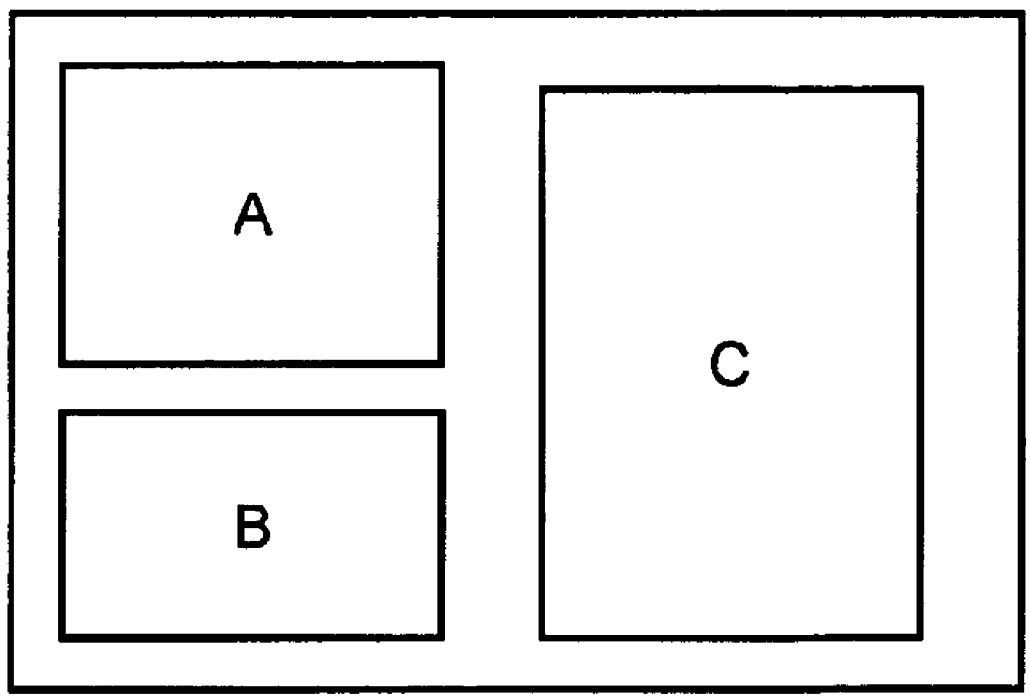
FIG. 43 is a plane view illustrative of a semiconductor wafer divided into function blocks A, B and C in a twenty third embodiment in accordance with the present invention.

Twenty Third Embodiment:

A twenty third embodiment according to the present invention will be described in detail with reference to the drawings. In this embodiment, a semiconductor wafer is divided into blocks which correspond to function blocks. FIG. 43 is a plane view illustrative of a semiconductor wafer divided into function blocks A, B and C. Usually, the contact hole sizes are different between the individual function blocks, whereby the difficulty in formation of the contact holes are different among the function blocks A, B, C. The function block having a highest difficulty has a highest probability of appearance of the defective contact holes. This function block is first checked. This function block may include a plurality of the above blocks which have the same size as in the previous twenty second embodiment. If one function block has a high difficulty in formation of the contact holes and the checking time is too limited to check the all function blocks, then it is possible to check only the function block having the high difficulty.

Figure 44:
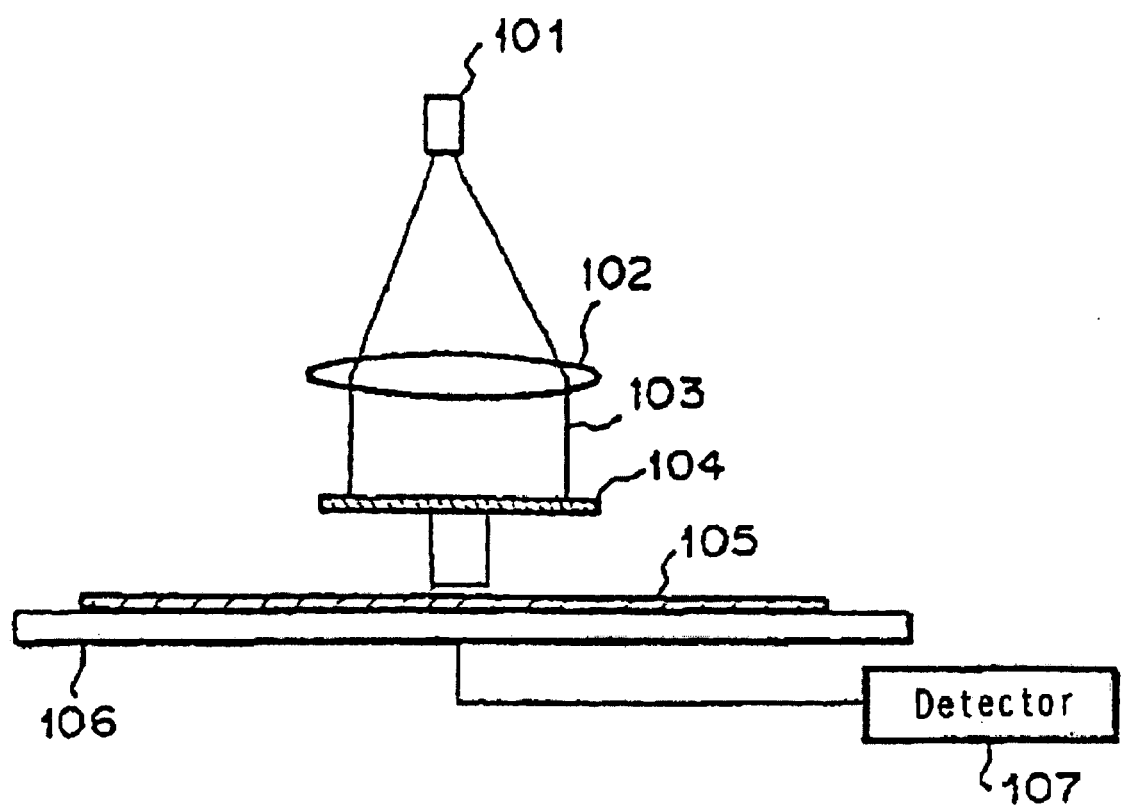
FIG. 44 is a schematic view illustrative of a novel electron beam irradiation system in a twenty fourth embodiment in accordance with the present invention, which is usable for conducting the above novel methods described in the twenty second and twenty third embodiments.

Twenty Fourth Embodiment:

A twenty fourth embodiment according to the present invention will be described in detail with reference to the drawings. In this embodiment, an electron beam irradiation system is provided which is usable for conducting the above novel methods described in the twenty second and twenty third embodiments. FIG. 44 is a schematic view illustrative of a novel electron beam irradiation system in a twenty fourth embodiment, which is usable for conducting the above novel methods described in the twenty second and twenty third embodiments. The system has an electron gun 101, a lens 102, a variable aperture 104, an electrode 106 and a beam pass current detector 107. A semiconductor wafer 105 is provided on the electrode 106. An electron beam 103 with a spread passes through the lens 102 whereby the electron beam 103 is made into a parallel electron beam 103. This parallel electron beam 103 is transmitted through the variable aperture 104 and irradiated onto the wafer 105, whereby the irradiation of the parallel electron beam 103 keeps the vertical incident angle to the surface of the wafer 105. The irradiation of the parallel electron beam 103 onto the wafer 105 causes the beam pass current which reaches the electrode 106 whereby the beam pass current is detected by the beam pass current detector 107.

Figure 45:
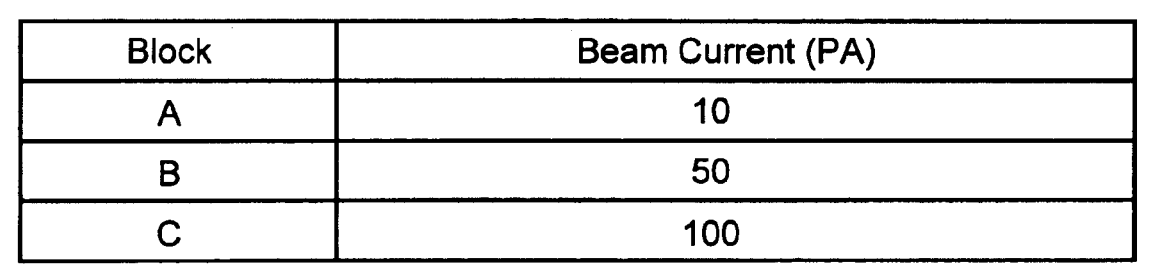

FIG. 45 is a table on which the blocks and irradiation electron beam current values of the individual blocks are shown when the electron beam irradiator system of FIG. 44 is used in this twenty fourth embodiment. The individual function blocks are different in area, for which reason in order to keep good signal-to-noise ratio, the electron beam current is adjusted so that the electron beam current injected into the individual contact holes is uniform. The density of the contact holes is independent from the areas of the individual blocks. The electron beam 103 is adjusted so that even the contact hole density varies, the beam pass current penetrating the contact holes are measured at the necessary high accuracy. Further, not only the increase in the electron beam but also the reduction in input conversion noise of the beam pass current detector 107 allows increasing a maximum area on which the measurement at one time is possible.

Figure 46:
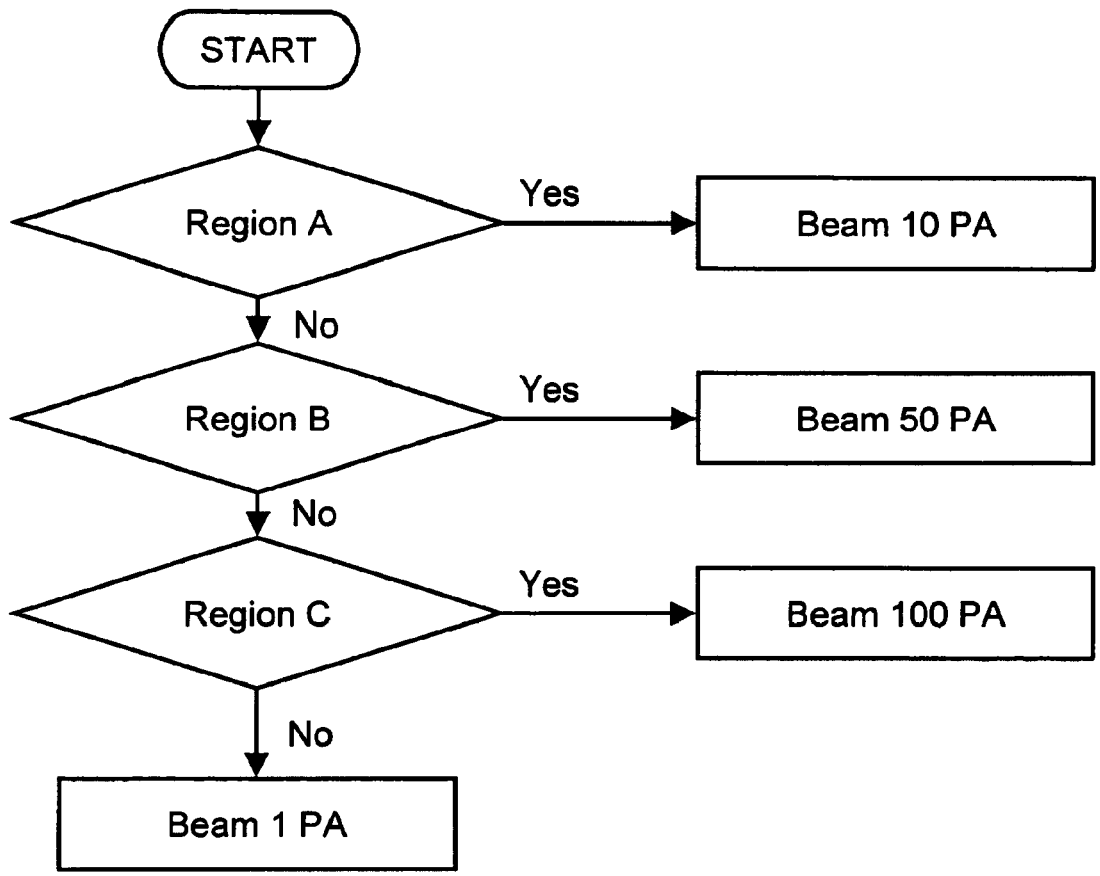
FIG. 46 is a flow chart illustrative of process for irradiation of electron beam onto individual blocks of the wafer under control of the electron beam as shown in FIG. 45 by use of the electron beam irradiator system of FIG. 44.

The above irradiation process is carried out as follows. FIG. 46 is a flow chart illustrative of process for irradiation of electron beam onto individual blocks of the wafer under control of the electron beam as shown in FIG. 45 by use of the electron beam irradiator system of FIG. 44. The wafer and the electrode are mounted on a two-dimensional X-Y stage. The position of the wafer is first confirmed to determine which block is about to receive the irradiation of the electron beam. The intensity of the electron beam is decided in accordance with the table of FIG. 45. Onto the block "A", the electron beam of 10 pA is irradiated as a first irradiation step. Onto the block "B", the electron beam of 50 pA is irradiated as a second irradiation step. Onto the block "C", the electron beam of 100 pA is irradiated as a third irradiation step.

Figure 47:
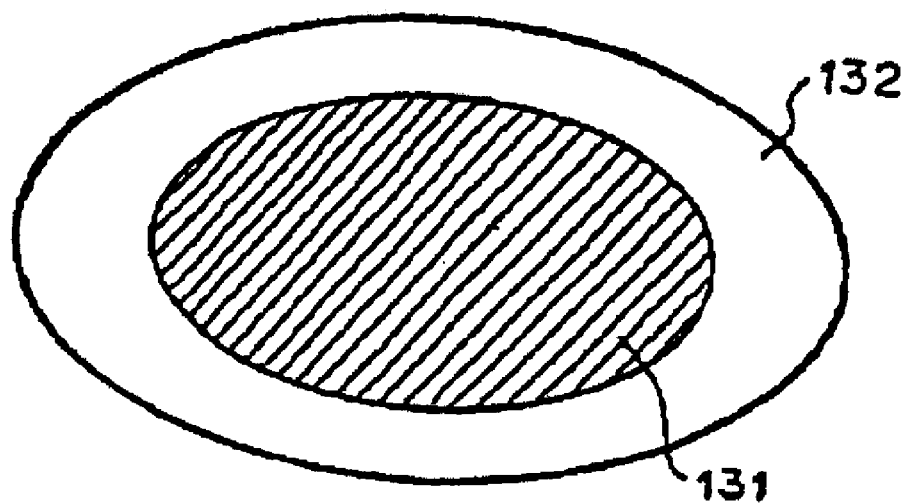
FIG. 47 is a plane view illustrative of a wafer isolated into a center region and a peripheral region with different weights in probability of appearance of the defective contact holes in a twenty fifth embodiment in accordance with the present invention.

Twenty Fifth Embodiment:

A twenty fifth embodiment according to the present invention will be described in detail with reference to the drawings. In this embodiment, a defective contact hole distribution property is considered due to etching system to give the weight to the probability of appearance of the defective contact holes over positions of the wafer. FIG. 47 is a plane view illustrative of a wafer isolated into a center region and a peripheral region with different weights in probability of appearance of the defective contact holes. The wafer is isolated into a center region 131 having a low probability of appearance of the defective contact holes and a peripheral region 132 having a high probability of appearance of the defective contact holes. If the contact holes are formed by plasma etching, then an abnormal plasma may be caused in the peripheral region, for which reason the probability of appearance of the defective contact holes in the peripheral region 132 is higher than the center region 131. The checking to the peripheral region 132 may be made before that to the center region 131. If the contact holes are formed by different processes and the probability of appearance of the defective contact holes in the center region 131 is higher than the peripheral region 132, then the center region 131 having a high probability of appearance of the defective contact holes is first tested before the peripheral region 132 having a high probability of appearance of the defective contact holes.

Figure 48:
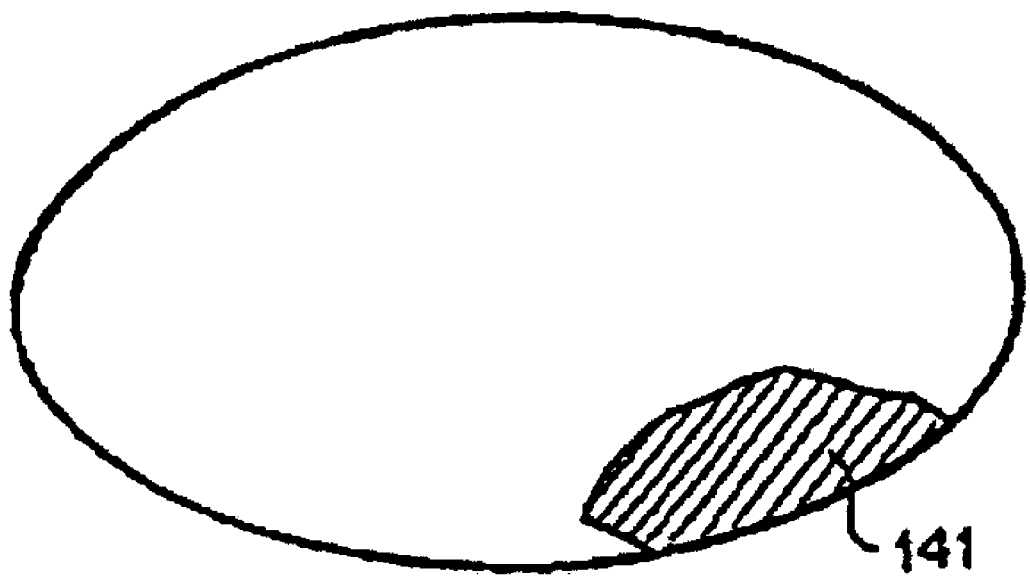
FIG. 48 is a plane view illustrative of a wafer having a contact region having a higher probability of appearance of the defective contact holes in a twenty sixth embodiment in accordance with the present invention.

Twenty Sixth Embodiment:

A twenty sixth embodiment according to the present invention will be described in detail with reference to the drawings. In this embodiment, a defective contact hole distribution property is considered due to etching system to give the weight to the probability of appearance of the defective contact holes over positions of the wafer. FIG. 48 is a plane view illustrative of a wafer having a contact region having a higher probability of appearance of the defective contact holes.

When the wafers are carried by a wafer carrier, it is possible that a contact region 141 of the wafer is made into contact with an inner wall of the wafer carrier. This contact region 141 has a higher probability of appearance of the defective contact holes than other regions. For this reason, the checking to the contact region 141 is first conducted before that to the other region.

Figure 49:
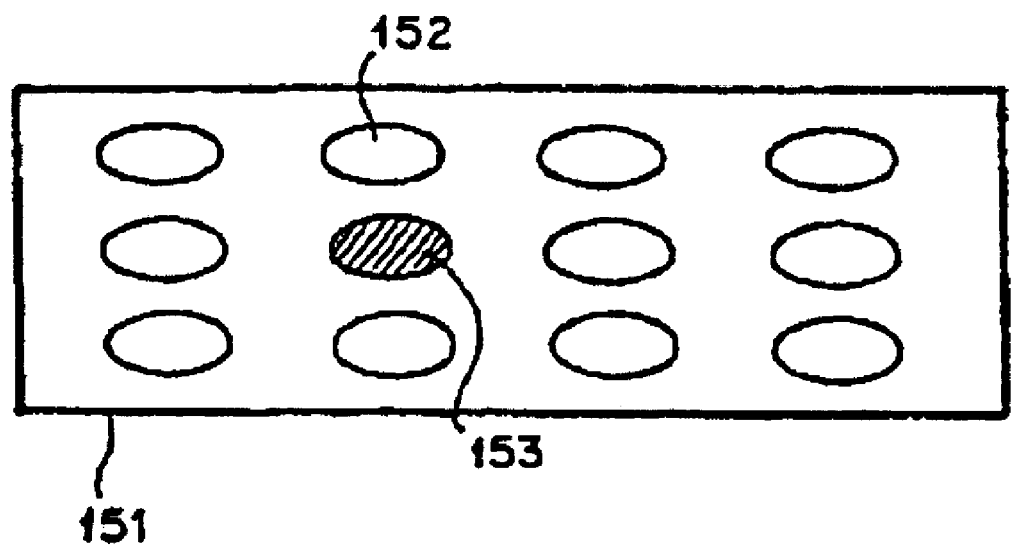
FIG. 49 is a view illustrative of a sub-block having a single defective contact hole and effective contact holes in a twenty seventh embodiment in accordance with the present invention.

Twenty Seventh Embodiment:

A twenty seventh embodiment according to the present invention will be described in detail with reference to the drawings. FIG. 49 is a view illustrative of a sub-block having a single defective contact hole and effective contact holes. The sub-block 151 has a single defective contact hole 153 and effective contact holes 152. The electron beam is irradiated onto the sub-block 151. If no defective contact hole exists in the block namely all of the contact holes in the block are perfect, then the beam pass current is maximum Imax. If, however, as shown in FIG. 49, the single contact hole 153 in the block is defective, then the beam pass current is lower than the maximum Imax. If the actually measured current value is given by Imes and the number of the contact holes in the block is "N", then the estimated number of the defective contact holes is given by N(Imax−Imes)/Imax.

Figure 50:
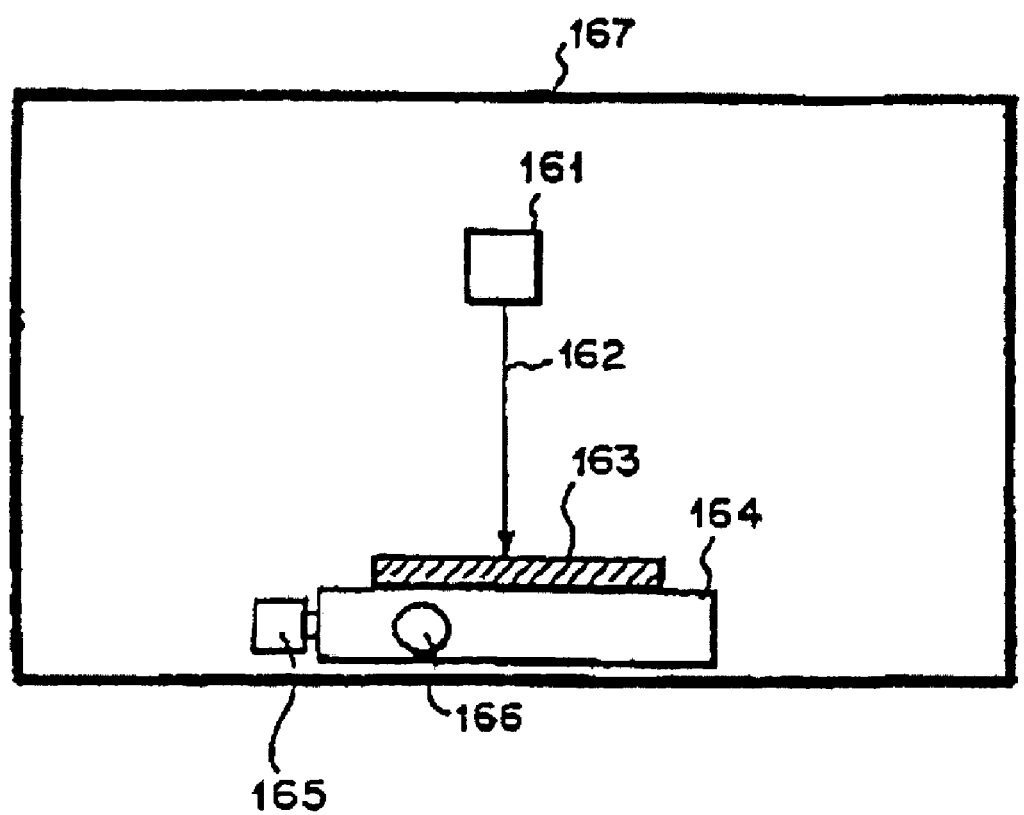
FIG. 50 is a schematic view illustrative of a novel electron beam irradiation system in a twenty eighth embodiment, which is usable for conducting the above novel methods described above.

Twenty Eighth Embodiment:

A twenty eighth embodiment according to the present invention will be described in detail with reference to the drawings. In this embodiment, an electron beam irradiation system is provided which is usable for conducting the above novel methods described above. FIG. 50 is a schematic view illustrative of a novel electron beam irradiation system in a twenty eighth embodiment, which is usable for conducting the above novel methods described above. The system has a vacuum chamber 167, an electron gun 161, an X-Y stage 164 with an X-axis stepping motor 165 and a Y-axis stepping motor 166. A semiconductor wafer 163 is provided on the X-Y stage 164. An electron beam 162 is irradiated from the electron gun 161 onto the surface of the wafer 163 with a two-dimensional scanning in co-operation with the two-dimensional movement of the X-Y stage 164, so that the beam spot is moved onto every blocks or sub-blocks. The necessary accuracy in alignment of the beam spot to the block or sub-block is much lower than when the beam spot is just aligned onto the contact hole. The necessary time for alignment of the electron beam to the block or sub-block is much shorter than when the beam spot is just aligned onto the contact hole.

Figure 51:
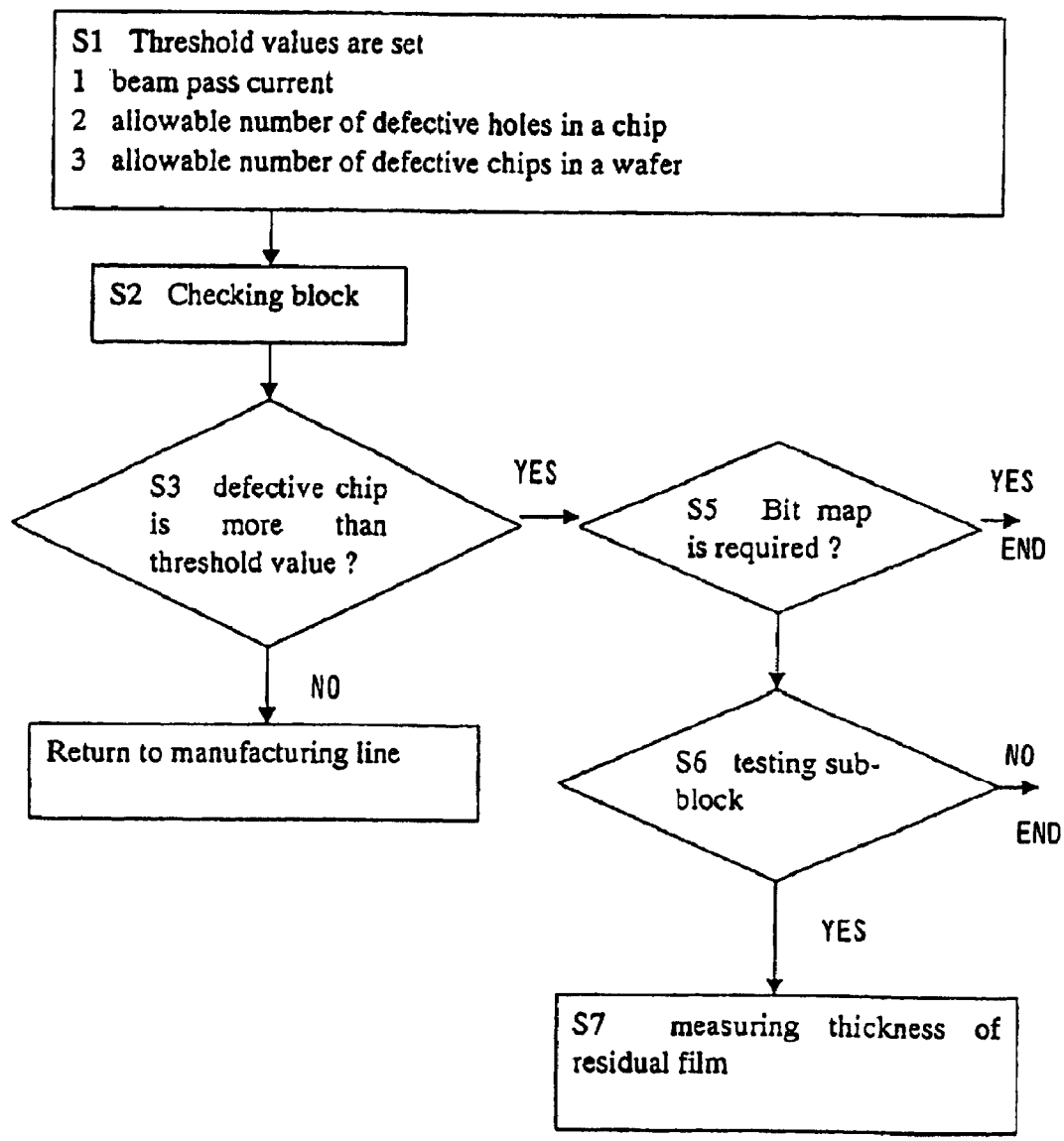
FIG. 51 is a flow chart illustrative of a novel process of testing wafers in a twenty ninth embodiment in accordance with the present invention.

Twenty Ninth Embodiment:

A twenty ninth embodiment according to the present invention will be described in detail with reference to the drawings. FIG. 51 is a flow chart illustrative of a novel process of testing wafers in a twenty ninth embodiment in accordance with the present invention. In a first step S1, threshold values are determined of a beam pass current, an allowable number of the defective contact holes in a chip and an allowable number of the defective chips in a wafer. In a second step S2, a checking process is made for every blocks, wherein an electron beam is irradiated onto the individual blocks so as to measure the beam pass current values of the individual blocks. If the measured beam pass current is lower than the beam pass current threshold value, then this block is considered to be defective. If the measured beam pass current is lower than the allowable number of the defective contact holes in the chip, then the block corresponding to the chip is considered to be non-defective. If the measured beam pass current is higher than the allowable number of the defective contact holes in the chip, then the block corresponding to the chip is considered to be defective.

In a third step S3, the number of the defective blocks or defective chips is counted. If the number of the defective blocks or defective chips is lower than the allowable number of the defective chips in the wafer, then the wafer is returned to the manufacturing line. If the number of the defective blocks or defective chips is higher than the allowable number of the defective chips in the wafer, then the wafer is removed from the manufacturing line.

In a fourth step S5, if the number of the defective blocks or defective chips is higher than the allowable number of the defective chips in the wafer, it is confirmed whether or not a bit map is required In a fifth step S6, if the bit map is required, the defective block is divided into sub-blocks for further testing the same. If the sub-block is higher in beam pass current than the threshold value, then the sub-block is considered to be non-defective. If the sub-block is lower in beam pass current than the threshold value, then the sub-block is considered to be defective.

In a sixth step S7, the measurement to the thickness of the residual film on the contact hole bottom is made to determine whether the individual contact holes are defective or non-defective.

Whereas modifications of the present invention will be apparent to a person having ordinary skill in the art, to which the invention pertains, it is to be understood that embodiments as shown and described by way of illustrations are by no means intended to be considered in a limiting sense. Accordingly, it is to be intended to cover by claims all modifications which fall within the spirit and scope of the present invention.

What is claimed is:

1. A system for detecting a residual film in one or more contact holes on a semiconductor wafer, the system comprising:

an electron gun to irradiate an electron beam on the one or more contact holes;

a detector, to measure a current at a back surface of the wafer, wherein the current is generated in response to the electron beam irradiated on the one or more contact holes; and a comparator, coupled to the detector, to determine the presence of the residual film in the one or more contact holes using the amount of current measured by the detector.

2. The system of claim 1 wherein the detector includes an electrode, to support the wafer and, to capture the current.

3. The system of claim 2 wherein the detector further includes a current amplifier, coupled to the electrode, to amplify the current and output an amplified current.

4. The system of claim 3 wherein the detector further includes a differential amplifier, coupled to the current amplifier, to remove offset currents from the amplified current and output an amplified current value.

5. The system of claim 3 wherein the detector further includes an analog-to-digital converter, coupled to the differential amplifier, to generate a digital representation of the amplified current value.

6. The system of claim 5 wherein the comparator is coupled to the analog-to-digital converter and uses the digital representation of the amplified current value to determine the presence of the residual film in the one or more contact holes.

7. The system of claim 1 further including a processor, coupled to the comparator, to determine a thickness of the residual film in the one or more contact holes.

8. The system of claim 1 wherein the electron gun irradiates the electron beam on the one or more contact holes at a plurality of electron beam accelerations.

9. The system of claim 1 wherein the electron gun irradiates the electron beam along a beam axis and wherein the beam axis is constant relative to the surface of the wafer.

10. The system of claim 1 wherein the electron gun irradiates the electron beam along a beam axis and wherein the system further includes a variable aperture, disposed in the beam path between the electron gun and the wafer, to control the vertical incident angle of the electron beam relative to the surface of the wafer.

11. The system of claim 1 further including an X-Y stage which is adapted to move the wafer, relative to the electron beam, in two directions.

12. The system of claim 11 wherein the X-Y stage, in response to control signals, aligns the one or more contact holes on the wafer so that the electron beam irradiates the one or more contact holes.

13. The system of claim 11 wherein:

the X-Y stage moves the wafer relative to the electron beam; and the detector measures a plurality of currents at a back surface of the wafer, wherein each current is generated in response to the electron beam irradiated on a different portion of the wafer.

14. The system of claim 1 wherein the electron gun irradiates the wafer with the electron beam in a scanning manner.

15. The system of claim 1 wherein the comparator determines the presence of the residual film in the one or more contact holes using the current and a reference value.

16. The system of claim 15 wherein the reference value is determined using a test region having a pattern of one or more contact holes that are the same as the pattern of the one or more contact holes.

17. A method for detecting a residual film in one or more contact holes on a semiconductor wafer, the method comprising:

irradiating the one or more contact holes with an electron beam;

measuring a current at a back surface of the wafer wherein the current is generated in response to the irradiating the one or more contact holes with the electron beam;

detecting a residual film in the one or more contact holes using the amount of the measured current.

18. The method of claim 17 further including comparing the current with a reference current wherein the reference current is generated in response to the irradiating a reference region, having one or more contact holes, with an electron beam.

19. The method of claim 18 wherein the reference region is a portion of a reference wafer.

20. The method of claim 17 wherein irradiating the one or more contact holes with an electron beam includes irradiating the one or more contact holes with the electron beam at a constant beam angle relative to the surface of the wafer.

21. The method of claim 17 wherein irradiating the one or more contact holes with an electron beam includes irradiating the one or more contact holes with the electron beam having a plurality of electron beam accelerations.

22. The method of claim 17 wherein irradiating the one or more contact holes with an electron beam includes irradiating the one or more contact holes with an electron beam having a variable electron beam acceleration.

23. The method of claim 17 wherein irradiating the one or more contact holes with an electron beam includes irradiating the one or more contact holes with an electron beam having a constant electron beam acceleration.

24. The method of claim 17 further including scanning the electron beam relative to the wafer to irradiate the one or more contact holes.

25. The method of claim 17 further including moving the wafer in one or more directions relative to the electron beam while irradiating the one or more contact holes with an electron beam.

26. A system for inspecting a contact hole on a semiconductor wafer, the system comprising:

an electron gun to irradiate an electron beam onto the hole;

a current detector to detect a current passing from a bottom of the hole through a residual film residing on a bottom of the contact hole wherein the current is generated in response to the electron beam; and a comparator, coupled to the current detector, to determine the presence of the residual film using the amount of current detected by the current detector.

27. The system of claim 26 including a processing unit, coupled to the current detector, to determine the thickness of the residual film using the amount of current generated in response to the electron beam.

28. The system of claim 27 wherein the processing unit calculates the thickness of the residual film using a reference value.

29. The system of claim 26 wherein the current detector includes an electrode, which is to support the semiconductor wafer and, to capture the current passing from a bottom of the hole through a residual film disposed on the bottom of the contact hole.

30. The system of claim 26 wherein the electron gun irradiates the electron beam along a beam axis and wherein the beam axes is constant relative to the surface of the wafer.

31. The system of claim 26 wherein the electron gun irradiates the electron beam along a beam axis and wherein the system further includes a variable aperture, disposed in the beam path between the electron gun and the wafer, to control the vertical incident angle of the electron beam relative to the surface of the wafer.

32. The system of claim 26 further including an X-Y stage which is adapted to move the wafer, relative to the electron beam, in a plurality of directions.

33. The system of claim 32 wherein the X-Y stage aligns the contact hole on the wafer with the electron beam so that the electron beam irradiates the contact hole.

34. The system of claim 32 wherein:

the X-Y stage moves the wafer relative to the electron beam; and the current detector measures a plurality of currents at back surface of the wafer, wherein each current is generated in response to the electron beam irradiated on a different portion of the wafer.

35. The system of claim 26 wherein the comparator determines the presence of the residual film in the contact hole using the detected current and a reference value.

36. The system of claim 35 wherein the reference value is determined using a contact hole on a test region.

* * * * *